(12) United States Patent
Tamraz et al.

(10) Patent No.: US 12,399,101 B2
(45) Date of Patent: Aug. 26, 2025

(54) SYSTEM AND METHODS FOR TRACKING AND IDENTIFYING AIRBORNE PARTICLES

(71) Applicant: WLAB LTD, London (GB)

(72) Inventors: Eve Tamraz, London (GB); Cyrille Najjar, London (GB)

(73) Assignee: WLAB LTD, London (GB)

( * ) Notice: Subject to any disclaimer, the term of this patent is extended or adjusted under 35 U.S.C. 154(b) by 862 days.

(21) Appl. No.: 17/486,541

(22) Filed: Sep. 27, 2021

(65) Prior Publication Data

US 2022/0026334 A1  Jan. 27, 2022

Related U.S. Application Data

(63) Continuation-in-part of application No. PCT/US2020/024763, filed on Mar. 25, 2020.
(Continued)

(51) Int. Cl.
*G01N 15/06* (2024.01)
*G01N 1/22* (2006.01)
(Continued)

(52) U.S. Cl.
CPC ....... *G01N 15/0606* (2013.01); *G01N 1/2273* (2013.01); *G01N 15/0227* (2013.01);
(Continued)

(58) Field of Classification Search
CPC ............ G01N 1/2273; G01N 15/0227; G01N 15/0612; G01N 15/0606;
(Continued)

(56) References Cited

U.S. PATENT DOCUMENTS 4,222,755 A * 9/1980 Grotto .................... B01D 46/26
  55/498
5,001,463 A    3/1991 Hamburger
(Continued)

FOREIGN PATENT DOCUMENTS

EP    1158292 A2    11/2001
JP    2002045415 A *  2/2002
(Continued)

OTHER PUBLICATIONS

International Search Report and Written Opinion of the ISA/EP in PCT/IB2018/000362, dated Jul. 7, 2018, 10pgs.
(Continued)

*Primary Examiner* — John E Breene
*Assistant Examiner* — Truong D Phan
(74) *Attorney, Agent, or Firm* — Perilla Knox & Hildebrandt LLP; Jason M. Perilla

(57) ABSTRACT

A system and methods of tracking and identifying airborne particles using sensing devices that may include a fan and a collection plate. The fan forces air through the sensing device and airborne particles onto the collection plate. An imaging device captures images of the particles on the collection plate for analysis and identification. An image processing device determines pre-identified particles in the images. The images of other particles are processed and identified by a neural network processing device. Recommendations based on particle counts are provided to a user device. The user device may automatically control one or more devices in response to the recommendations.

15 Claims, 37 Drawing Sheets

Related U.S. Application Data

(60) Provisional application No. 62/823,289, filed on Mar. 25, 2019.

(51) Int. Cl.
    *G01N 1/24*          (2006.01)
    *G01N 15/0227*    (2024.01)
    *G01N 35/00*      (2006.01)

(52) U.S. Cl.
    CPC . *G01N 35/00871* (2013.01); *G01N 2001/245* (2013.01); *G01N 2035/00881* (2013.01)

(58) Field of Classification Search
    CPC ..... G01N 2001/2223; G01N 2001/245; G01N 2015/1486; G01N 2015/1497; G01N 2015/1493; G01N 2015/0294; G01N 2015/0046; G01N 1/2208
    See application file for complete search history.

(56) References Cited

U.S. PATENT DOCUMENTS

| | | | |
|---|---|---|---|
| 6,594,001 B1 | 7/2003 | Yabusaki | |
| 8,828,737 B2 | 9/2014 | Gabriel | |
| 9,551,600 B2 | 1/2017 | Howes et al. | |
| 2001/0008720 A1* | 7/2001 | Pedicini | H01M 8/04753 429/83 |
| 2003/0159498 A1 | 8/2003 | Small | |
| 2005/0250095 A1 | 11/2005 | Gabriel | |
| 2005/0261841 A1 | 11/2005 | Shepard et al. | |
| 2010/0075317 A1* | 3/2010 | Schneider | H01J 37/20 435/6.12 |
| 2011/0212512 A1 | 9/2011 | Wang et al. | |
| 2012/0131986 A1* | 5/2012 | Varanasi | A01N 25/18 73/23.35 |
| 2013/0291332 A1* | 11/2013 | Nakao | B08B 5/02 15/347 |
| 2015/0075301 A1 | 3/2015 | Scialo et al. | |
| 2015/0253247 A1 | 9/2015 | Nitta | |
| 2016/0041074 A1* | 2/2016 | Pliskin | G01N 15/0625 422/3 |
| 2016/0202222 A1 | 7/2016 | Roberts et al. | |
| 2016/0256097 A1 | 9/2016 | Manautou et al. | |
| 2016/0290912 A1 | 10/2016 | Kent et al. | |
| 2016/0320306 A1 | 11/2016 | Huffman et al. | |
| 2018/0191938 A1* | 7/2018 | Pena De Sousa Santos | G06T 7/571 |
| 2018/0266933 A1 | 9/2018 | Tamraz et al. | |
| 2019/0017917 A1 | 1/2019 | Mauro | |
| 2019/0029486 A1 | 1/2019 | Suvarna et al. | |
| 2020/0256806 A1* | 8/2020 | Nahler | G01S 7/4802 |
| 2022/0142283 A1* | 5/2022 | Hashimoto | A61B 5/4266 |

FOREIGN PATENT DOCUMENTS

| | | | |
|---|---|---|---|
| WO | 2014127379 A1 | 8/2014 | |
| WO | 2014207629 A1 | 12/2014 | |
| WO | WO-2016144823 A1 * | 9/2016 | ............... A61B 5/11 |
| WO | 2018118934 A1 | 6/2018 | |

OTHER PUBLICATIONS

International Search Report and Written Opinion of the ISA/US in PCT/US2020/024763, dated Aug. 12, 2020, 11pgs.

Search Report of the Great Britain Patent Office dated Jan. 23, 2018 in GB Application No. 1704078.3; 1pg.

Extended European Search Report for European Application No. 20776718.7 mailed Nov. 9, 2022.

Examination Report in IN Application No. 202117048460, mailed on Aug. 11, 2023.

* cited by examiner

Health and Environment Recommendations 1240

| Particle and Count | Pollution Sensor | Symptom | Severity | Health Advice | Environment Recommendation |
|---|---|---|---|---|---|
| Birch Pollen | None | Sneezing | Low | Rinse Face | Close Windows, Air Purifier |
| | | | Medium | | Close Windows, Air Purifier, |
| | | | High | Take Medication | Close Windows, Air Purifier, Change Air Filter, Lower Temperature |
| | | Sneezing & Red Eyes | Low | Rinse Face&Eyes | Close Windows, Air Purifier |
| | | | Medium | | Close Windows, Air Purifier, |
| | | | High | Take Medication | Close Windows, Air Purifier, Change Air Filter, Lower Temperature |

Recommendation Database 1230

*Fig. 12B*

Symptom Table 2950

| Environment Sensor | Pollution Sensor | Symptom | Severity | Advice |
|---|---|---|---|---|
| Birch Pollen | None | Sneezing | Low | Close Windows |
| | | | Medium | Close Windows & Rinse Face |
| | | | High | Close Windows, Rinse Face & Take Medication |
| | | Sneezing & Coughing | Low | Close Windows |
| | | | Medium | Close Windows, Sit down & Rinse face |
| | | | High | Close Windows, Sit down, Rinse Face & Take Medication |

⋮

Database 2420

*Fig. 27B*

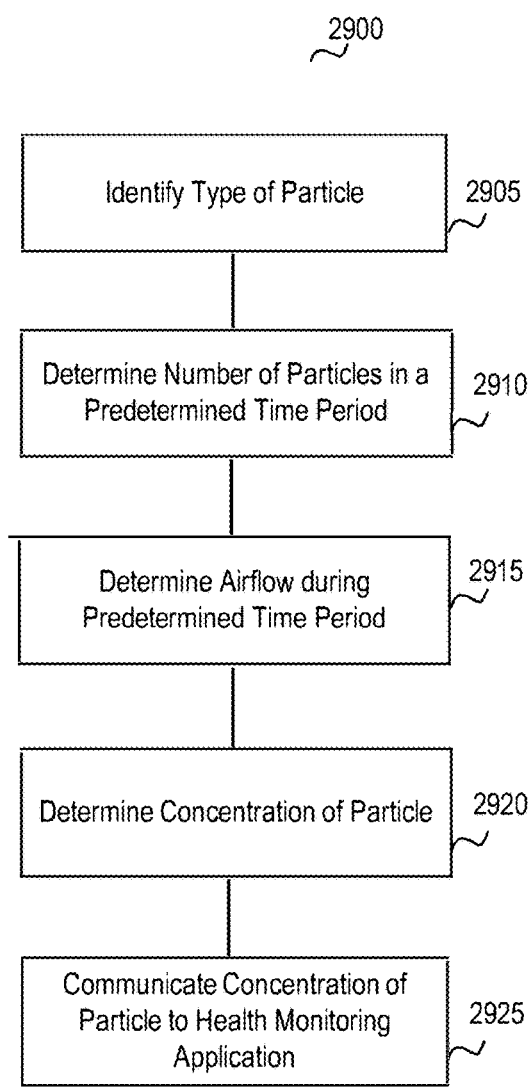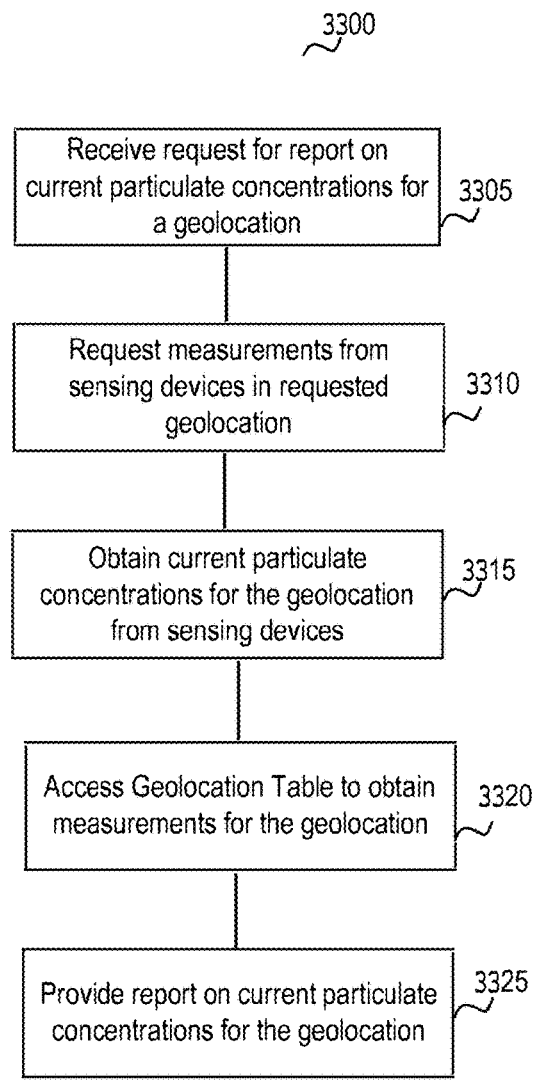
*Fig. 31*
*Fig. 32*

SYSTEM AND METHODS FOR TRACKING AND IDENTIFYING AIRBORNE PARTICLES

CROSS REFERENCE TO RELATED APPLICATIONS

This application is a continuation-in-part under 35 U.S.C. 111(a) of International Application PCT/US2020/024763 filed Mar. 25, 2020, which claims priority to U.S. Provisional Application No. 62/823,289 filed Mar. 25, 2019, each of which are hereby expressly incorporated by reference in their entirety.

FIELD OF INVENTION

This application relates to systems and methods for monitoring and identification of types of airborne particles and provision of health advice in response thereto.

BACKGROUND

Allergic reactions to particles are debilitating and, in some instances, can be fatal. In order to monitor these particles, techniques exist whereby sticky tape is used to capture, in particular, airborne particles. This tape is sent to a laboratory for analysis by a technician. The technician reviews the sticky tape under a microscope and identifies the types of particles. The user then receives the results of the analysis by the technician.

This current technique has several drawbacks. First, due to the large amount of human analysis, the cost for the technique is high. The results derived from this technique can be quite poor. Second, there is the risk of contamination during the capture and transportation for analysis which may lead to false results. Third, the analysis of the sticky tape may take days, so the results only indicate the airborne particles from several days ago. This delay means that the particle information is not current and may not be used for immediate determination of a cause of allergic symptoms. In addition, allergen levels are often only analyzed and provided for a large geographical area, such as an entire city or region and is not representative of the immediate environment of the user. It would be desirable, therefore, to provide a substantially real-time and automated mechanism to detect allergens.

In addition, there is no known mechanism to prevent or warn of particulates especially indoors. Typically, an individual only becomes aware of the presence of allergensor other airborne particles after the individual begins suffering symptoms. For example, the user may start sneezing or having breathing difficulties. The user will then need to medicate. It would be desirable, therefore, to be able to provide real time warnings of any increase in airborne particulates so that a user may take preventative action.

As such, there is a need for an air monitoring system, methods, and devices that timely detect and identify airborne particles in a personal space of a user and provides health advice and environment recommendations based on the identified types of airborne particles. Furthermore, there is a need for a system and methods that provide alerts to the user including a potential cause of symptoms and warns the user to take preventative actions. The present disclosure satisfies these needs.

SUMMARY OF THE INVENTION

According to one embodiment, a sensing device includes a collection plate; a fan configured to generate air flow through a receptacle of the sensing device and force the particles in the air flow towards the collection plate; an imaging device configured to capture images of particles situated on the collection plate; and a control device configured to control a speed of the fan to generate the air flow, wherein the speed of fan is determined using a location of the sensing device of the sensing device.

According to another embodiment, a central device includes a network interface circuit configured to communicate over a network to a sensing device and at least one processing device configured to obtain a current image of a plurality of particles from the sensing device. The at least one processing device is further configured to determine a location of a first particle using the current image; compare the location of the first particle to locations of other particles in prior images from the sensing device; determine the location of the first particle is substantially same as a location of one of the other particles in prior images from the sensing device from the sensing device; discard a portion of the current image including the first particle; locate at least a second particle in the current image; and obtain a particle identification of the second particle in the current image.

According to another embodiment, user equipment (UE) includes a transceiver configured to communicate over a network to central device and at least one processing device configured to generate a GUI including a particle count of an allergen for a user location; receive an environment recommendation from the central device to lower the particle count of the allergen from the user location, wherein the environment recommendation includes adjusting a setting of one or more devices at the user location; and generate a command to adjust the setting of the one or more devices at the user location based on the environment recommendation.

According to another embodiment, a sample identification device comprises a database storing characteristics of a reference sample in association with advice for a user corresponding to a health issue associated with the sample, and control circuitry configured to compare the characteristics of a sample under test with the stored characteristics; determine the identity of the sample in accordance with the comparison and return the associated advice to the user, wherein the database associates the advice with symptoms experienced by a user and, the control circuitry is further configured to return the advice associated with the identified sample and the symptoms.

In another embodiment, a sample identification device further comprising communication circuitry configured to be connected to a network and to receive the characteristics of the sample under test.

In another embodiment, a sample identification method comprises storing characteristics of a reference sample in association with advice for a user corresponding to a health issue associated with the sample, comparing the characteristics of a sample under test with the stored characteristics; determining the identity of the sample in accordance with the comparison and return the associated advice to the user and associating the advice with symptoms experienced by a user and returning the advice associated with the identified sample and the symptoms.

In another embodiment, a sample identification device comprising a database storing characteristics of a plurality of reference samples comprising airborne particles, in association with advice for a user corresponding to a health issue associated with the reference samples, and control circuitry configured to compare the characteristics of a sample under test with the stored characteristics; determine the identity of the airborne particles in the reference samples in accordance with the comparison and return an identification of the airborne particle in the samples, a level of airborne particles in the samples, and the associated advice to the user, wherein the database associates the advice with symptoms experienced by a user and, the control circuitry is further configured to return the advice associated with the identified sample and the symptoms.

In another embodiment, a sample identification method comprises storing, in a database, characteristics of a reference sample in association with advice for a user corresponding to a health issue associated with the sample; comparing the characteristics of a sample under test with the stored characteristics of the reference sample; and determining the identity of the sample in accordance with the comparison and returning the associated advice to the user; and associating the advice with symptoms experienced by a user and returning each of the advice associated with the identified sample and the symptoms to the user.

In another embodiment, a sample identification device comprises a database storing characteristics of a plurality of reference samples, each of the plurality of references samples comprising an airborne particle; a control circuitry or a cloud based network configured to compare the characteristics of a sample under test with the stored characteristics and determine an identity of the sample under test in accordance with the comparison, and return the associated identification of the airborne particle in the sample under test and an amount of the airborne particle in the sample under test to the user, wherein the database associates the identification and the amount with symptoms experienced by a user and, the control circuitry or the cloud based network is further configured to return a symptom diagnostic to the user based on the identification and the amount of the airborne particles detected and symptoms log.

In still another embodiment, a sample identification method comprises storing, in a database, characteristics of a plurality of reference samples, each of the plurality of reference samples comprising an airborne particle, each of the plurality of reference samples in association with advice for a user corresponding to a health issue associated with each of the plurality of reference samples; using control circuitry or a cloud-based network configured to compare the characteristics of a sample under test with the stored characteristics of the reference sample; and determining the identity of the airborne particles in the sample according to the comparison and returning to the user the identity of the airborne particle in the sample under test and an amount of the airborne particle in the sample under test; and returning to the user a symptom diagnostic based on the identification and the amount of the airborne particles detected and symptoms log.

In yet another embodiment, a computer program comprises computer readable instructions which, when loaded onto a computer, configure the computer to perform a method comprising storing characteristics of a reference sample in association with advice for a user corresponding to a health issue associated with the sample, comparing the characteristics of a sample under test with the stored characteristics; determining the identity of the sample in accordance with the comparison and return the associated advice to the user and associating the advice with symptoms experienced by a user and returning the advice associated with the identified sample and the symptoms.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 12B illustrates a schematic block diagram of an embodiment of a recommendation database;

FIG. 27B illustrates schematic block diagrams of an embodiment of a database;

FIG. 31 illustrates a logical flow diagram of an embodiment of a method to determine a concentration of a particle under test; and FIG. 32 illustrates a logical flow diagram of an embodiment of a method of reporting a concentration of a particle under test.

DETAILED DESCRIPTION

Definitions

Figure 1:
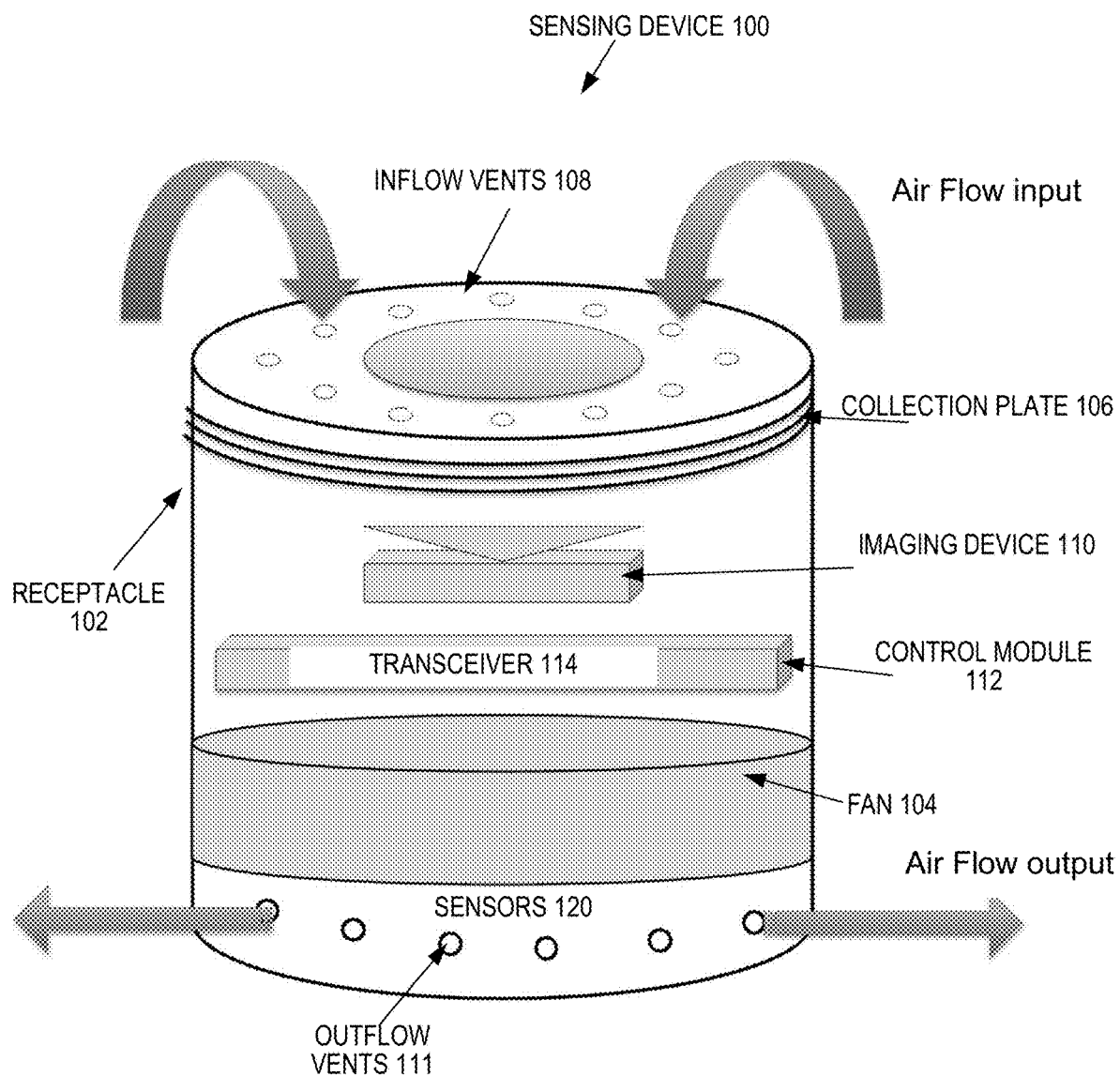
FIG. 1 illustrates a schematic block diagram of an embodiment of a sensing device.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated hereinby reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

Embodiments of the Disclosure

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

FIG. 1 illustrates a schematic block diagram of an embodiment of a sensing device 100 that automates the capture and imaging of microscopic particles in the ambient air for continuous monitoring of allergen levels. The sensing device 100 includes a receptacle 102 having a fan 104 and a collection plate 106. The fan 104 is configured to generate an air flow through the receptacle 102 and force the particles in the air flow towards the collection plate 106. For example, the air flow carries airborne particles through one or more inflow vents 108 into the receptacle 102 and onto the collection plate 106. The collection plate 106 is made of a transparent material and may be covered with an electrostatic coating configured to attract the airborne particles. The air flow then exits one or more outflow vents 111 in the receptacle 102.

Airborne particles may land naturally over time on the collection plate 106, or the airborne particles may be directed to the collection plate 106. For example, the airborne particles may be directed to the collection plate 106 using the fan 104 to push or pull air flow to the collection plate 106. In an embodiment, the collection plate 106 may have a positive charge to attract particles.

In one embodiment, the fan 104 may generate a fixed air flow mimicking lung capacity of human breathing, e.g., at approximately 8 liters per min. The speed of the fan 104 is set to generate an air flow to the collection plate 106 of approximately 8 liters/min. The air flow thus provides an estimate of the air inhaled by a user and the actual particle inhalation of a user.

In another embodiment, the air flow generated by the fan 104 may be faster (e.g., for faster air quality assessment) or slower depending on the use and environment of the sensing device 100. For example, for a workplace or factory environment, the speed of the fan 104 may be controlled to a faster speed. In an outdoor environment with heavy particle concentration, the fan 104 may be slower.

The sensing device 100 includes an imaging device 110 configured to capture images of the airborne particles on the collection plate 106. The imaging device 100 may illuminate the collection plate 106 with light from one or more spectrums including, e.g., visible, ultraviolet (UV), near infrared or infrared light. The imaging device 110 is configured with an auto-focus or manual focus of one or more lenses for magnification and capturing images of various sized particles on the collection plate 106, as described in more detail herein. A brush, high impaction fan or other means may be implemented to periodically clean the collection plate 106 of airborne particles. In another embodiment, sticky tape or other surface may be implemented for collecting the airborne particles.

A control module 112 includes one or more processing circuits and memory devices. The processing circuit includes one or more processing devices, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The one or more memory devices may include a read-only memory, random access memory, volatile memory, non-volatile memory, static memory, dynamic memory, flash memory, cache memory, and/or any non-transitory memory device that stores digital information. The storage device stores one or more instructions or programs which when performed by the one or more processing circuits, instructs the sensing device 100 to perform one or more functions described herein.

The control module 112 may further include a wireless and/or wireline transceiver 114 configured to communicate over a WLAN, Bluetooth, cellular network or other WAN or short-range network. The transceiver 114 may communicate data to and from a central server over a WAN and download remote software updates or commands from the central server.

The sensing device 100 may also include other sensors 120, such as pollution detectors, temperature sensors, humidity detector, barometric pressure, etc.

Figure 2:
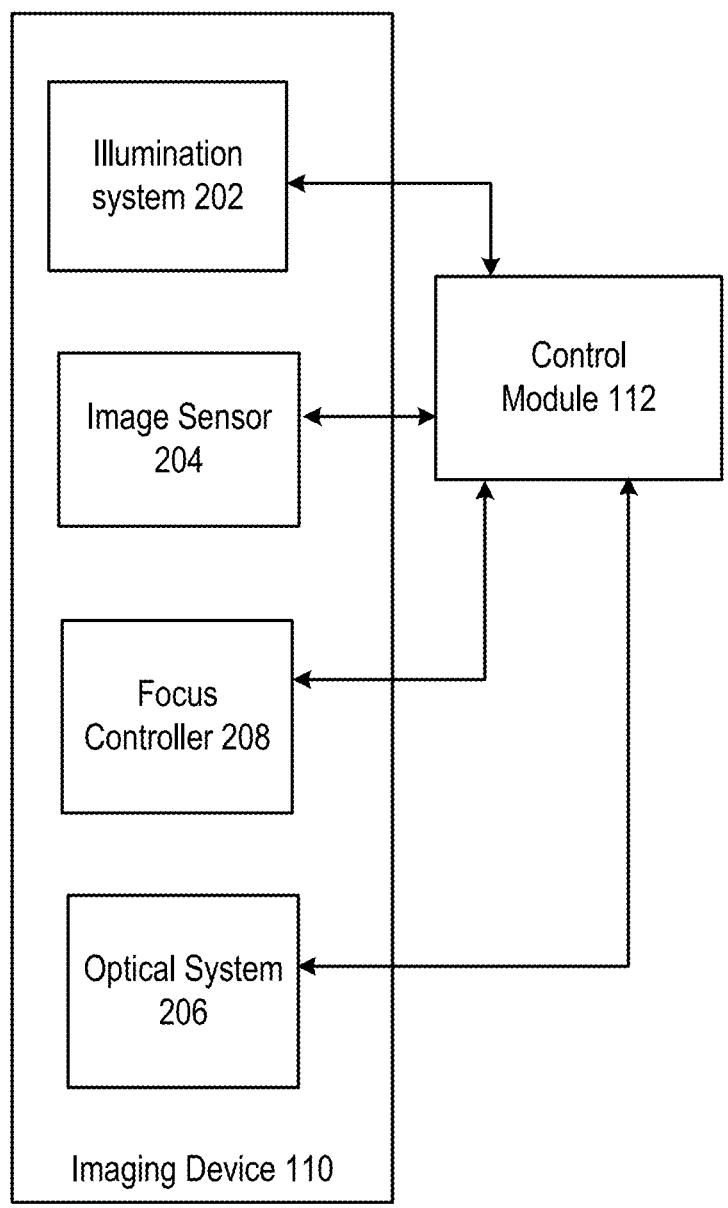
FIG. 2 illustrates a schematic block diagram of an embodiment of the imaging device in more detail.

FIG. 2 illustrates a schematic block diagram of an embodiment of the imaging device 110 in more detail. The imaging device 110 includes an image sensor 204, such as CMOS, and an illumination system 202. The illumination system 202 includes one or more light sources (such as LEDs) configured to emit light in one or more spectrums, e.g., one or more of visible, ultraviolet (UV), near infrared or infrared light.

The optical system 206 includes one or more lenses for magnification of the particles on the collection plate 106. The focus controller 208 includes mechanical and/or electronic mechanisms to adjust a focus of the lenses. The control module 112 or the focus controller 208 or a combination thereof may control the focus of the optical system 206 as described herein. The focus controller 208 may include a combination of auto-focus or manual focus of the optical system.

In an embodiment, the focus controller 208 may automatically detect a focus for imaging a variety of different sized particles on the collection plate 106. For example, the imaging device 110 may capture images with different focal planes. The optical system 206 includes various lenses for magnification of the particles. The distances of the lenses are changed to adjust the focal plane. The various focal points may vary between, e.g., 2-100 microns. A series of images of the collection plate 106 are obtained at different focal points.

By combining images with various focal planes, the different sized particles may be imaged on the collection plate 106. An image processing device may use image layering techniques to achieve a wider focus plane.

An illumination system 202 may include an array of LEDs in one or more different spectrums. The LEDs may include white LEDs, NIR/IR LEDs, and/or UV LEDs. Using different light combinations, the contours of particles may be further differentiated. An image sensor 204 includes a CMOS camera. In another embodiment, the image sensor 204 and illumination system 202 may include fluorescence or spectroscopy techniques.

Figure 3:
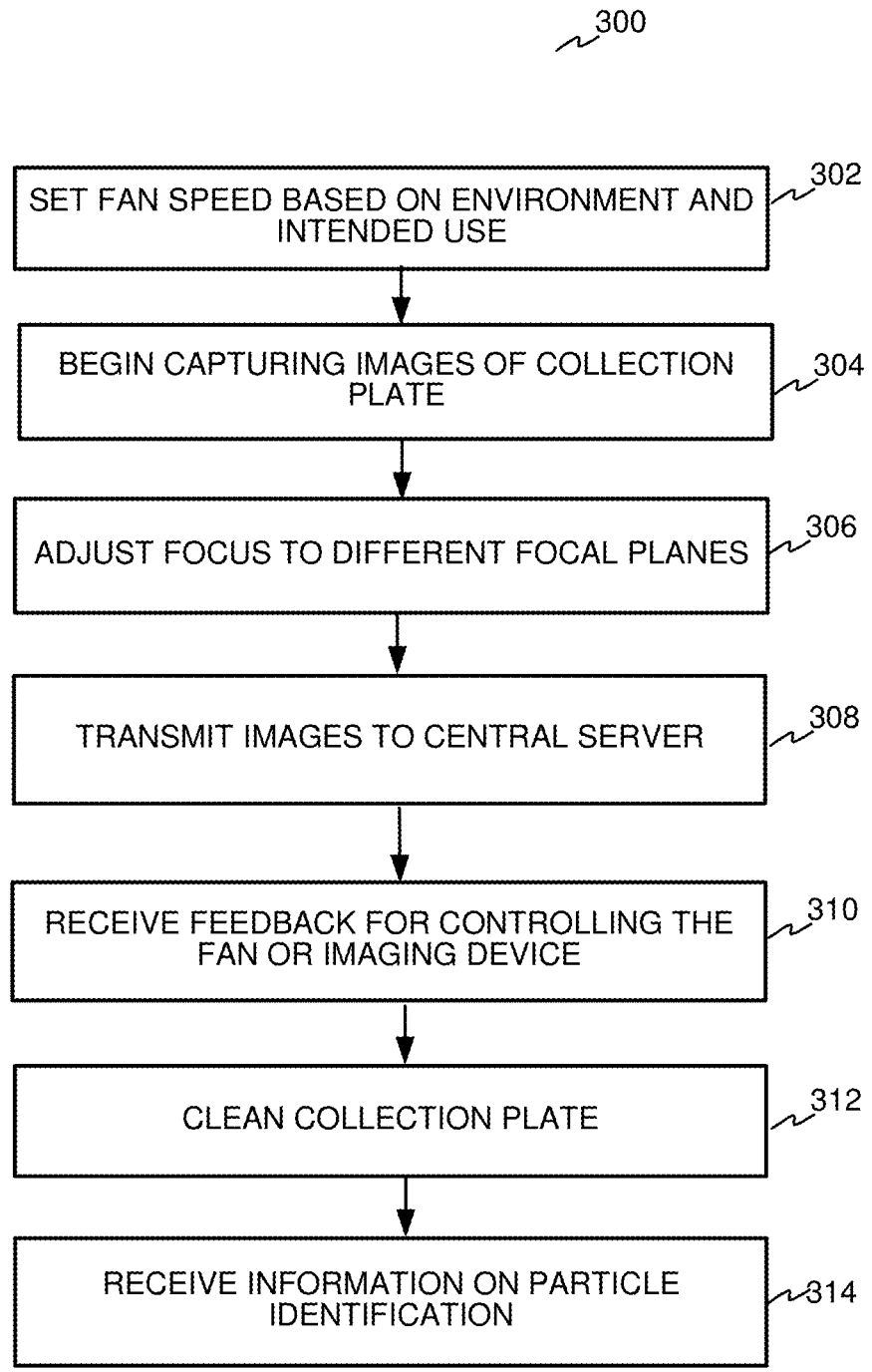
FIG. 3 illustrates a schematic block diagram of a method of operation of the sensing device.

FIG. 3 illustrates a schematic block diagram of a method of operation 300 of the sensing device 100. The speed of the fan 104 is determined and set by the control module 112 based on the location or environment and intended use at 302. For example, for personal use in a residence, the fan 104 may be set to constant air flow mimicking lung capacity of human breathing, e.g. at approximately 7-9 liters per min. The air flow thus provides an estimate of actual particle inhalation of a user, and the sampling of the airborne particles is a good representation of particle intake by a person. The threshold of particle intake that triggers symptoms in a user may also be determined more accurately.

In an industrial location, the air flow generated by the fan 104 may be set at higher speeds, e.g., for faster air quality assessment. For example, in a hospital, manufacturing plant, office building or other industrial setting, it may be more important to obtain a faster determination of airborne particles. The fan 104 may thus be set at a speed to generate air flow greater than 9 liters/min. through the receptacle 102 of the sensing device 100. In external or outside environments, the fan 104 may set to slower speeds, e.g., lower than 7 liters/min. The airborne particles in outdoors settings may not change as quickly and so a slower capture and identification of particles may be acceptable. In addition, due to a higher density of airborne particles in outdoor settings, the particles on the collection plate 106 may become obstructed at higher fan speeds.

The fan setting may thus be determined and set based on a location of the sensing device 100, e.g., industrial setting or residential setting or an outdoor environment. The control module 112 may receive user input of the location of the sensing device 100 and determine a fan speed based on the user input.

In addition, the fan speed may be adjusted in response to a change of particle density on the collection plate 106. For example, when the particle density on the collection plate 106 increases rapidly, the fan speed may be decreased from its current setting for better imaging and identification of the particles. Alternatively, if particle density is changing slowly, the fan speed may be increased from its current setting to obtain further specimens more quickly. The air flow may be changed in increments of 1 liter/min until an acceptable change in density of particles on the collection plate is obtained over time.

The imaging device 110 captures images of particles on the collection plate 106 at 304. The imaging device 110 using auto-focus obtains images with different focal planes at 306. The various focal points may vary between, e.g., 2-100 microns. A series of images of the collection plate 106 are thus obtained at different focal points.

The sensing device 100 transmits the images to a central server for image processing and identification of the particles at 308. The sensing device 100 may receive feedback from the central server for controlling the fan 104 or imaging device 110 at 310. For example, the feedback may include instructions to increase or decrease the fan speed or to change the focus or illumination of the collection plate.

The sensing device 100 cleans the collection plate 106 at 312 using a brush, a burst of high-speed air flow from the fan 104 or other means. The cleaning may be performed periodically, e.g., every 3-12 hours or after one or more days. In an embodiment, the sensing device 100 may receive feedback from the central server to clean the collection plate 106. For example, the central server determines from the images that too many clusters of particles are present on the collection plate 106 or particle density reaches a predetermined threshold that particle differentiation is difficult. Thus, the central server may trigger cleaning when clustering or density of the particles on the collection plate 106 reaches predetermined thresholds that inhibit particle differentiation in the captured images.

Information on particle identification may be received from the central server for display on the sensing device 100 or transmitted to a user device for display at 314.

Figure 4:
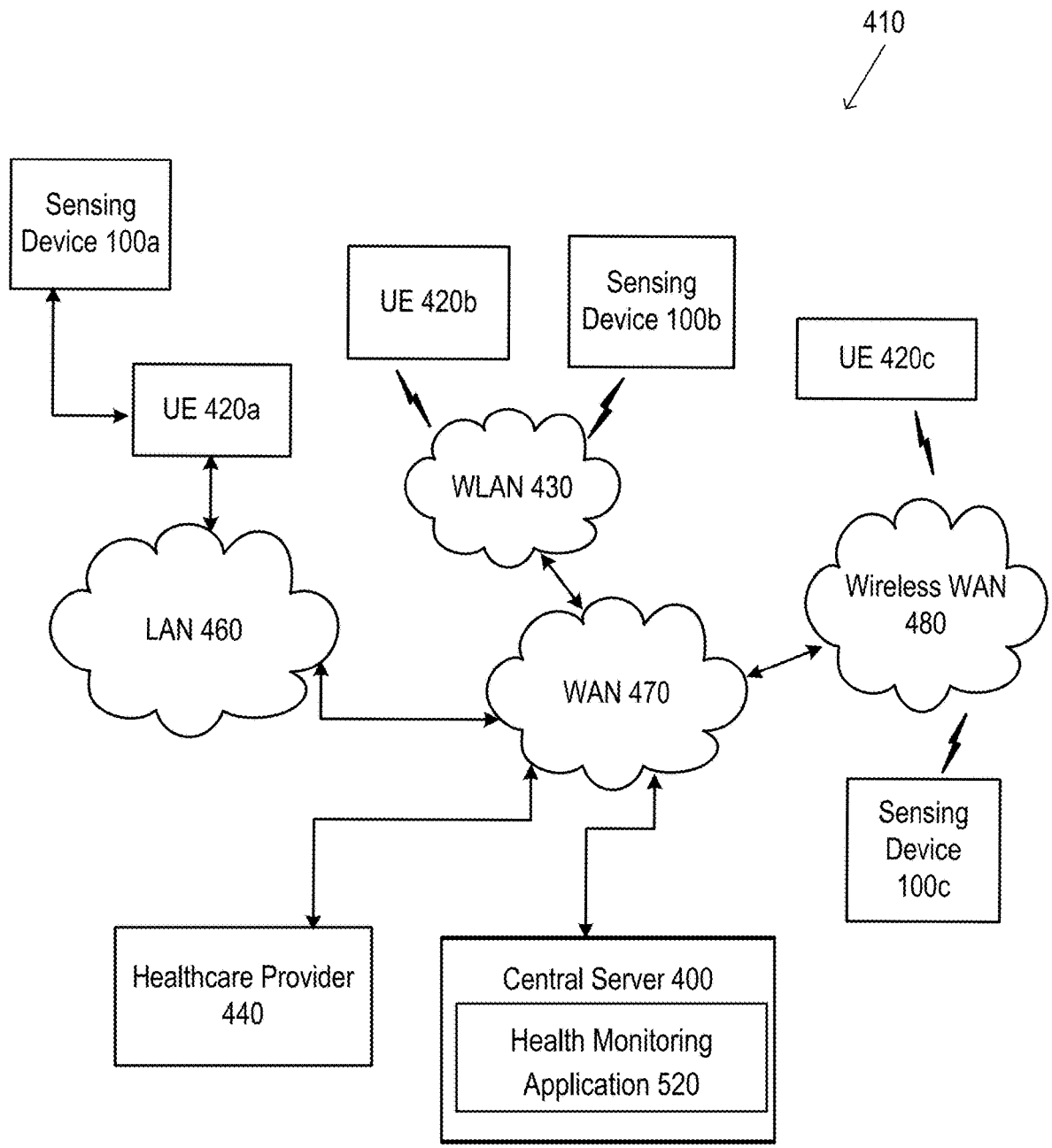
FIG. 4 illustrates a schematic block diagram of an embodiment of an exemplary network.

FIG. 4 illustrates a schematic block diagram of an embodiment of an exemplary network 410. The exemplary network 410 includes one or more networks that are communicatively coupled, e.g., such as a wide area network (WAN) 470, a wired local area network (LAN) 460, a wireless local area network (WLAN) 430, and/or a wireless wide area network (WAN) 480. The LAN 460 and the WLAN 430 may operate inside a residence or in an enterprise environment, such as an office building, manufacturing plant, hospital, retail store, hotel, restaurant, clinic or other facility. The wireless WAN 480 may include, for example, a cellular network, a WIMAX network, an EDGE network, a GERAN network, etc. or a satellite network or a combination thereof. The WAN 470 includes the Internet, service provider network, other type of WAN, or a combination of one or more thereof.

The user equipment (UE) 420*a*, 420*b*, 420*c* may communicate over the network 410 to one or more sensing devices 100*a*, 100*b*, 100*c*, to a central server 400, to a healthcare provider 440, to other UEs 420*a-c*, etc. The UE 420 may include a smart phone, laptop, desktop, smart tablet, smart watch, or any other electronic device.

Each of the sensing devices 100 are communicatively coupled to one or more of the UEs 420 directly or through one or more of the exemplary networks. The sensing devices 100 may be located in a residence or in an enterprise environment, such as a hospital, manufacturing plant, office, hotel, clinic, stadium or other facility. The sensing devices 100 may also be located outside in parks, streets, highways, tops of buildings, etc. In addition, a sensing device 100 may be located on trains, cars, planes or other modes of transportation. The sensing devices 100 are configured to capture and image airborne particles and transmit the images to the central server 400 over the network 410. Though a single central server 400 is illustrated, the central server 400 may include a plurality of servers or other computing devices in one or more locations.

The sensing devices 100 and central server 400 may thus be used to detect levels of allergen and pollutants. For example, the sensing devices 100 may provide images for identification of particles to the central server 400. The central server 400 determines levels of allergen and pollutants found locally outside, such as around a building, street, or one or more parts of a city. The central server 400 may also provide identification and levels of allergen and pollutants found inside within a residence, workplace, retail center, factory, stadium, or other indoor area. Using the network 410, the identification and levels of allergen and pollutants found in other cities, states, countries or internationally may also be provided to the UE 420. The one or more sensing devices 100 may communicate with the central server 400 to perform one or more functions herein.

The network of sensing devices 100a-c also allows the users to compare levels of allergen and pollutants between an indoor area and outdoor area. Users with asthma, COPD, or other health conditions may determine to limit outdoor activity when outdoor levels of allergen and pollutants are higher based on such comparison. The identified airborne particles may include typical allergens such as pollen, ragweed, grass, rye, pet dander, birch, mold, *Artemisia*, etc. The identified airborne particles may also include pollutants, such as ozone, NOx, CO, Sox, etc. These listed types of particles are examples only and other types of particles may also be identified and monitored by the sensing devices 100 and central server 400.

Figure 5:
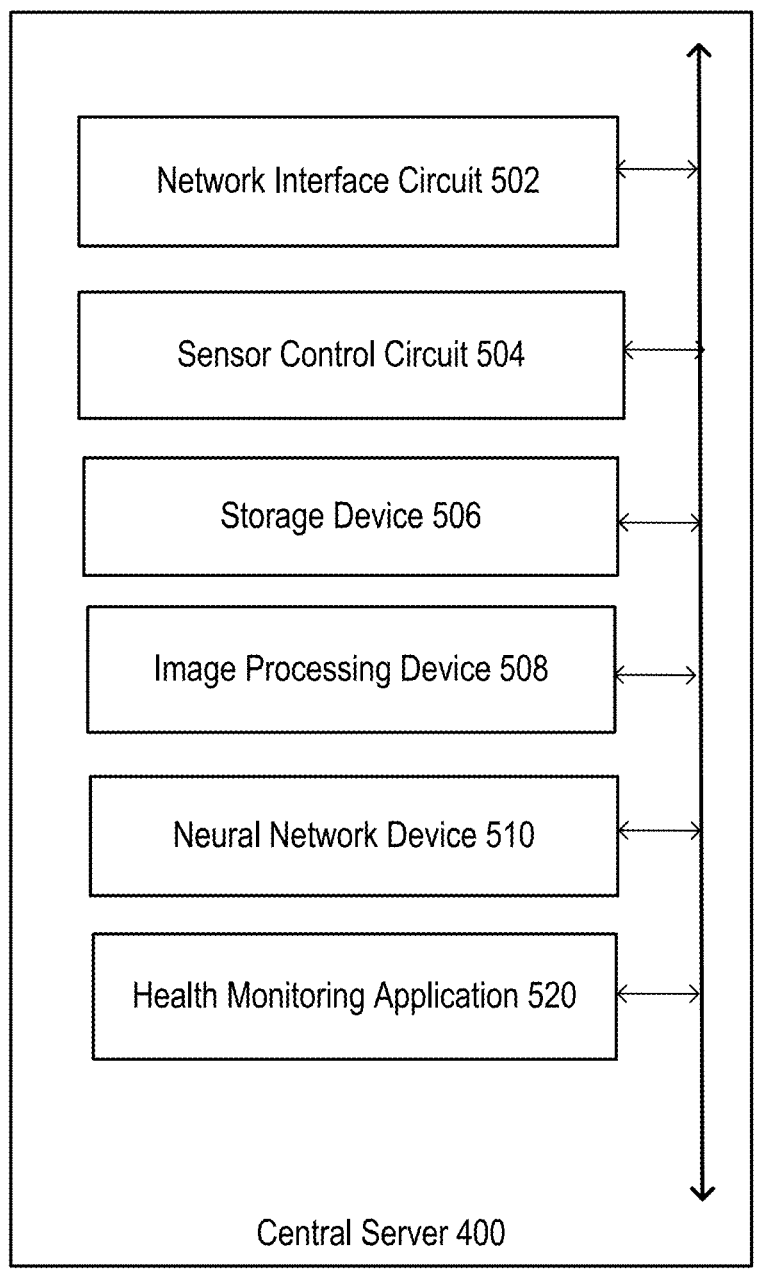
FIG. 5 illustrates a schematic block diagram of the central server in more detail.

FIG. 5 illustrates a schematic block diagram of the central server 400 in more detail. The central server 400 includes a network interface circuit 502 that includes an interface for wireless and/or wired network communications with one or more of the exemplary networks in the network 410. The network interface circuit 410 may also include authentication capability that provides authentication prior to allowing access to some or all of the resources of the central server 400. The network interface circuit 502 may also include firewall, gateway, and proxy server functions.

The sensor control circuit 504 is configured to control the one or more sensing devices 504. The sensor control circuit 504 may communicate software updates to the sensing devices 100 and provide feedback and commands to control operations of the sensing devices 100.

The central server 400 includes a health monitoring application 520. The health monitoring application 520 may be installed on or operable to communicate with the UEs 420 and sensing devices 100. The health monitoring application 520 may be a web-based application supported by the central server 400. For example, the central server 400 may include a web server that provides the health monitoring application 520 via a website. The UE 420 may access the functions and data of the health monitoring application 520 using a browser that accesses the central server 400. In another embodiment, the health monitoring application 520 is a stand-alone application that is downloaded to the UE 420 and is operable on the UE 420 without access to the central server 400 or accesses the health monitoring application 520 on the central server 400 for additional information or data. The sensing devices 100 may also include the health monitoring application 520 or be operable to communicate with the central server 400 to perform one or more functions described herein. Alternatively, the health monitoring application 520 and associated databases may be downloaded to a sensing device 100 such that the sensing device may be operable to perform one or more functions herein without communicating to the central server 400 over the network 410.

Additionally, the central server 400 may include an internal or external storage device 506. The storage device 506 may include a particle database and/or user database. The user database includes user specific profiles stored for each user of the health monitoring application 520. The particle database includes various particle data and images, including allergens such as pollen, pet dander, mold, and dust mites. Other types of particles may also include minerals, wood residue, pollutants, or other types of airborne particles. The neural network device 510 identifies the type of particle using the images in the particle database as described in more detail herein.

The image processing device 508 receives the images from the one or more sensing devices 100. Prior to identification by the neural network device 510, the image processing device 508 processes the images to improve data analysis and identification and also to reduce the server load. The image processing device 508 may employ various techniques to enhance images obtained under various illumination conditions. In addition, the image processing device 508 may combine images with various focal planes using image layering techniques to achieve a wider focus plane.

Figure 6:
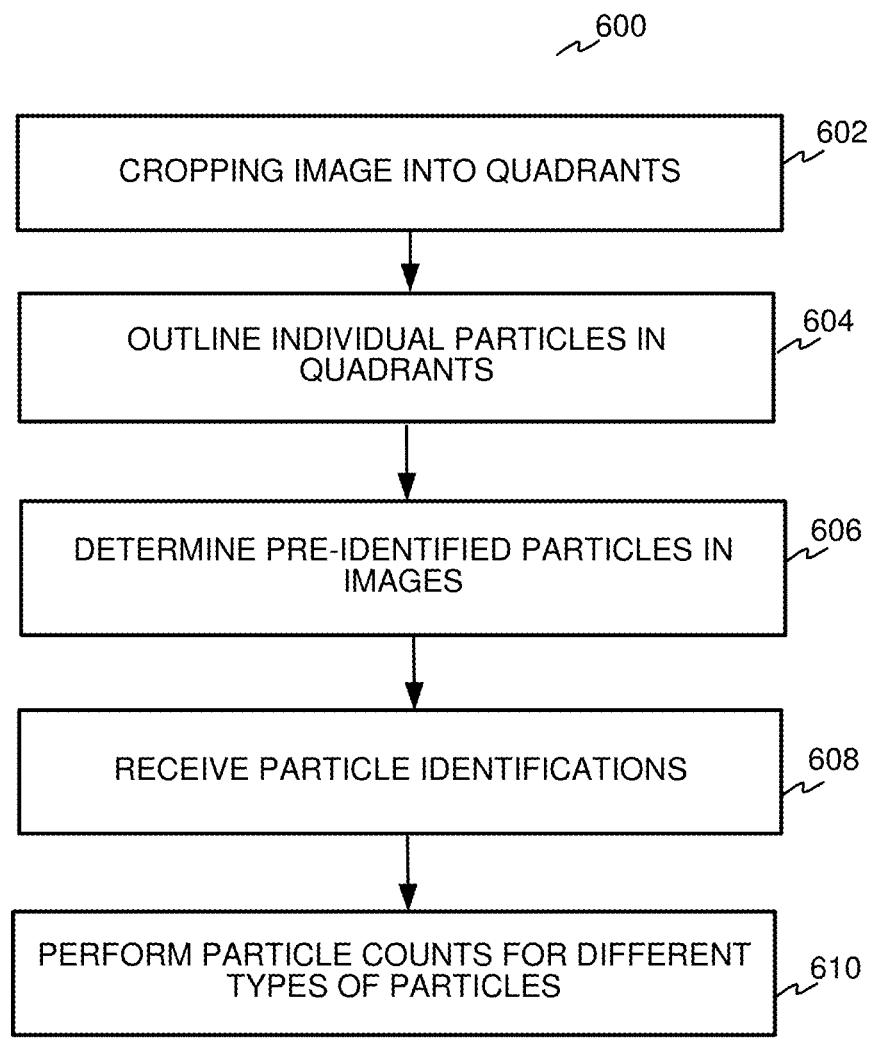
FIG. 6 illustrates a schematic block diagram of a method for processing the images of particles in more detail.

FIG. 6 illustrates a schematic block diagram of a method 600 for processing the images of the particles in more detail. The image processing device 508 crops or divides an image into quadrants at 602 and then performs an outline or cropping of individual particles in a quadrant at 604. This processing helps to locate individual particles in the image and separate particles in a cluster.

In an embodiment, prior to processing a located particle for identification, the image processing device 508 determines whether the particle was previously located and identified at 606. For example, the images taken of the collection plate over time may include particles previously imaged and identified. The image processing device 508 compares the position of a particle in a current image to the positions of previously identified particles in prior images. When a location of the particle in the current image is approximately the same to a previously identified particle in a prior image, the image processing device 508 determines that the particles are the same. The size of the particles as well as the position of the particles may also be compared in this determination. The portions of the current image including the particle is then discarded and not identified again. This saves time and server load. In addition, the same particles are not counted twice. The locations of the particles may be coordinates in relation to the collection plate or other reference point.

In addition, after a cleaning of the collection plate, pre-identified particles are compared to newly acquired images to determine if any particles remain. The images of any pre-identified particles are discarded and not identified again or included twice in the particle count. Thus, pre-identified particles in images acquired over time or that remain on the collection plate after cleaning are determined by the image processing device 508.

For particles not previously identified, the outline or cropped image of the individual particle is then processed for identification. The image processing device 508 receives particle identifications at 608 and may also perform particle counts for the different types of particles at 610. For example, the image processing device 508 may determine the particle counts using reading time, speed of air flow and identification of particles. The image processing device 508 determines a number of readings of an allergen per hour and an airflow within the sensing device 100. From this information, the sensing device 100 may obtain a concentration for different types of particles (such as parts per million PPM) with more accuracy.

Figure 7:
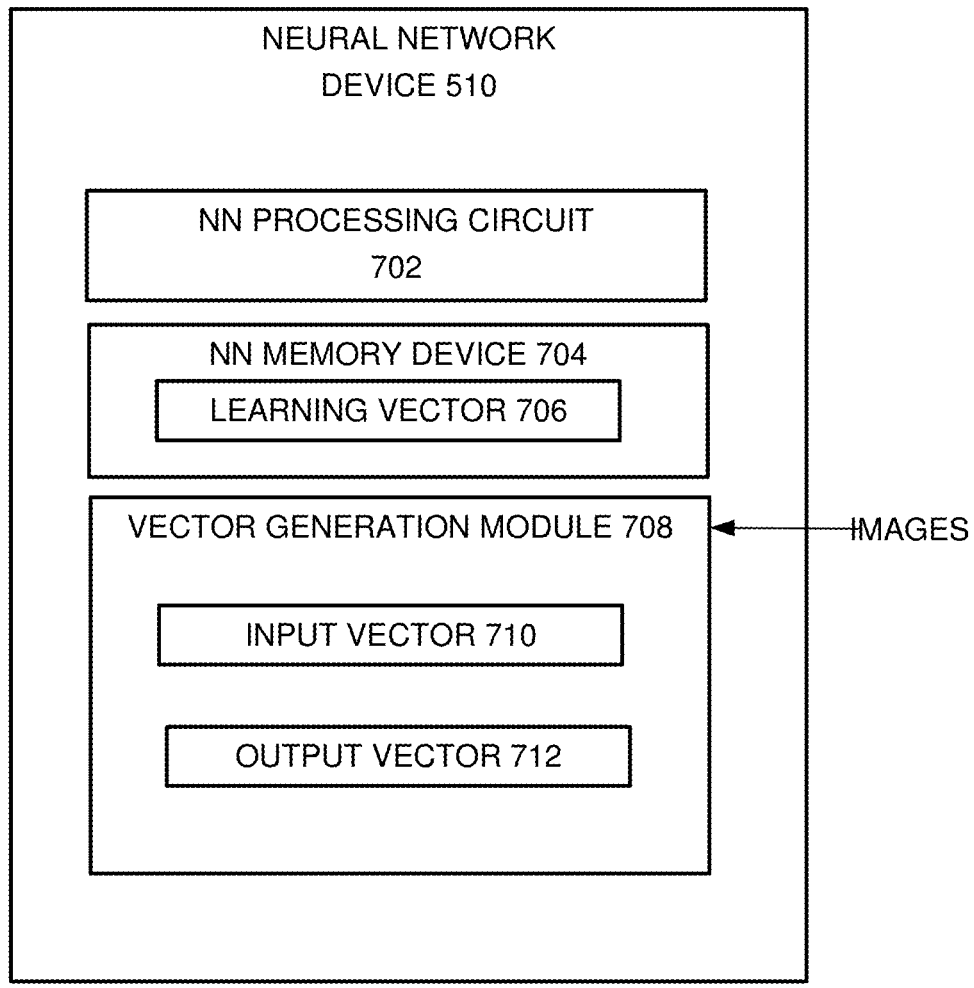
FIG. 7 illustrates a schematic block diagram of the neural network device in more detail.

FIG. 7 illustrates a schematic block diagram of the neural network device 510 in more detail. The neural network device 510 includes a neural network (NN) processing circuit 702 and NN memory device 704. The NN memory device 704 stores a learning vector 706 and updates thereto. An input vector generation module 708 is configured to generate the input vector 710 from the outline or cropped image of a particle. The input vector 710 may include texture, size, color, shape or other information determined using the image of the particle. The NN processing circuit 702 generates an output vector 712 that includes an identification of the particle from the particle image.

The NN processing circuit 702 is configured to implement a machine learning or artificial intelligence (AI) algorithm configured with the learning vector 706. During a learning stage, the neural network device 510 adjusts parameters, weights and thresholds of the learning vector iteratively to yield a known output vector from an input vector. The training is performed using defined set of rules also known as the learning algorithm. For example, a gradient descent training algorithm is used in case of supervised training model. In case, when the actual output is different from a target output, the difference or error is determined. The gradient descent algorithm changes the weights of the network in such a manner to minimize this error. Other learning algorithms include back propagation, least mean square (LMS) algorithm, a "random forest", deep belief network trained using restricted Boltzmann machines, or support vector machine. The analysis may use any known regression analysis technique, such as, for example and without limitation, random forests, support vector machines, or a deep belief network trained using restricted Boltzmann machines. Neural networks are also known as artificial neural networks, deep neural networks, artificial intelligence devices, etc.

The training set for the determining the learning vector may be obtained from clinical images of known particles. For example, a known allergen identified in a lab may be deposited on the collection plate 106, and its image captured by a sensing device 100. These images are then used as a training set for the neural network device 510. The training set and learning algorithm may be updated as particles are identified in the environment or new particle identifications are obtained. For example, when an identification of a particle is unknown, the image of the particle may be examined manually by a scientist and its identity determined. The image of the particle and its identity are then added to the training set and the learning algorithm updated.

Figure 8:
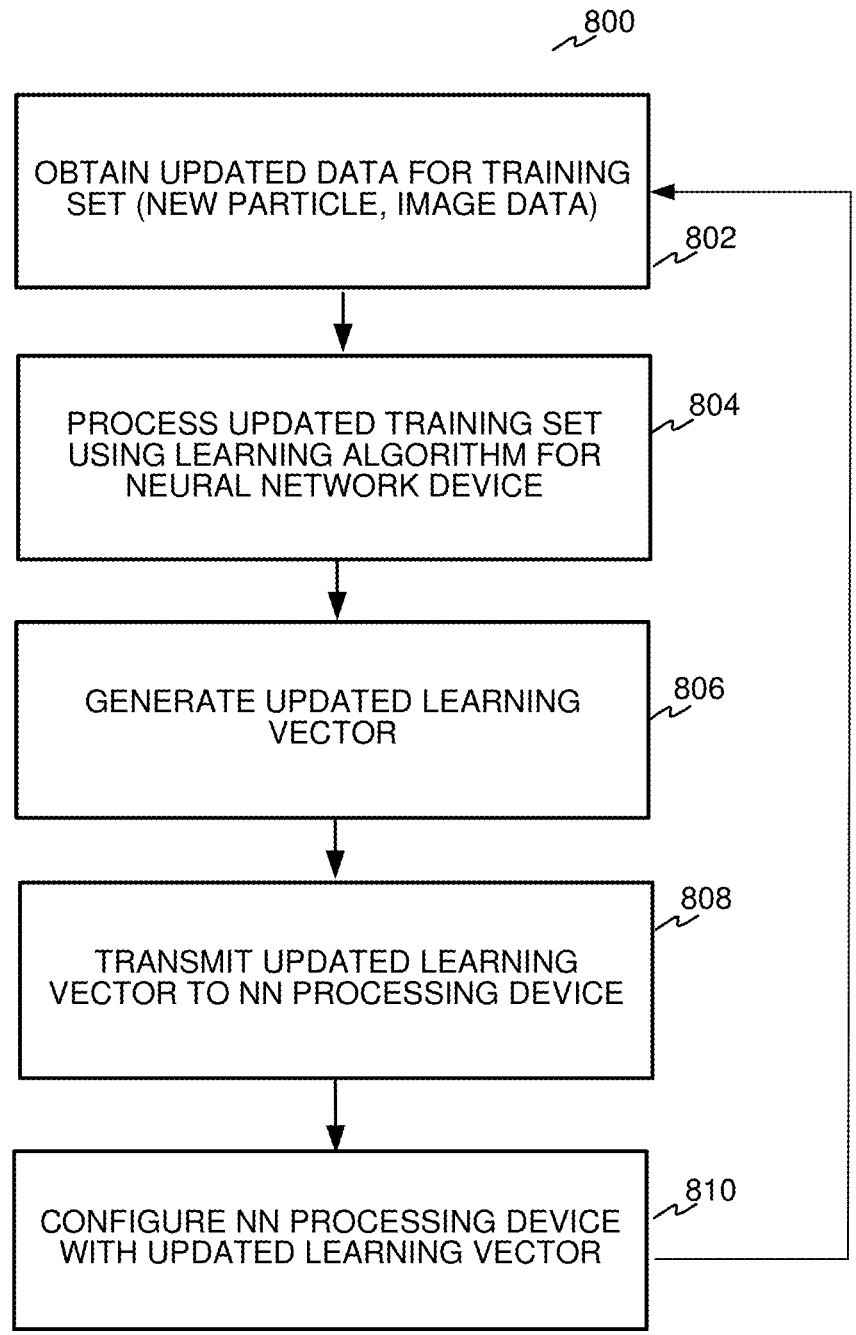
FIG. 8 illustrates a schematic block diagram of a method for updating a learning vector in the neural network device.

FIG. 8 illustrates a schematic block diagram of a method for updating a learning vector in the neural network device 510. The central server 400 may continually update the training set as it receives additional data and images of particles. The updated data may include images of known particles or images of newly identified particles. For example, updated images of particles or images of new particles may be obtained for the training set from clinical studies, laboratories, the sensing devices 100, or other sources at 802.

The updated training set is processed using a learning algorithm for the neural network device 510 at 804. An updated learning vector 706 is generated at 806 including processing parameters for the NN processing device 702. The updated learning vector 706 is transmitted to a central server 510 including the NN processing device 702 at 808. The NN processing device 702 is configured using the updated learning vector/processing parameters at 810. This process of updating the training set and learning vector may continue with periodic updates of the learning vector generated hourly, daily, weekly or monthly.

Figure 9:
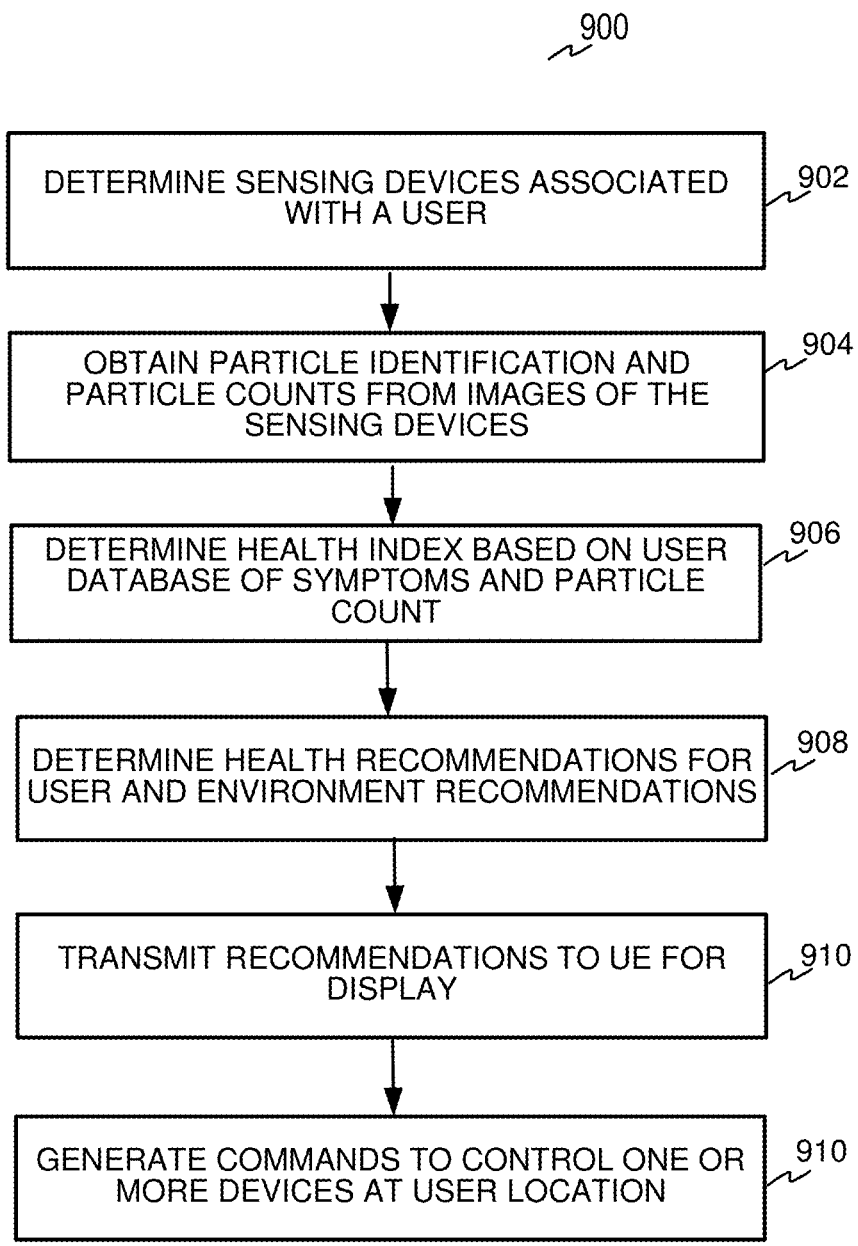
FIG. 9 illustrates a schematic block diagram of a method for providing allergen information and advice.

FIG. 9 illustrates a schematic block diagram of a method 900 for providing allergen information and advice. The central server 400 determines one or more sensing devices 100 associated with a user or UE 420 at 902. A sensing device 100 may be associated with multiple users/UE, e.g., at a same residence or office. In addition, multiple sensing devices at a home or office may be associated with a same user/UE of the user. The central server 400 obtains the particle identification and the particle count for identified particles at 904 from images obtained from the one or more sensing devices 100 associated with the user. Using the health monitoring application 520, the central server 400 determines a health index based on the user database of symptoms and the particle counts at 906. Health recommendations or advice may also be determined for the user at 908. For example, the central server 400 may use a database of health recommendations based on the particle type identified and their count and/or a database of health recommendations based on the user's sensitivity. These health recommendations may include taking an allergy medication, eye drops, using a mask, etc. Using a database of allergen count thresholds that trigger symptoms in the user, the central server 400 may provide a diagnostic of a user's allergies and the particle count that triggers a reaction in a user.

In an embodiment, environment recommendations may be determined at 908 as well. For example, the temperature, humidity, light, air flow through a location may affect the allergen levels affecting a user. The central server 400 may access a database of actions/recommendations to lower allergen levels in an environment based on the type of allergen and particle count. For example, for a high mold count, the central server 400 may generate a recommendation to turn on a dehumidifier or turn up a temperature on a thermostat. In response to dust mites, a recommendation to change humidity and lower temperatures may be generated. In response to an allergen, e.g., pollen/pet dander, a recommendation to control a device, such as an air purifier or close outside air vents may be issued. Other environment recommendations may include to control settings of a thermoset, humidifier, dehumidifier, heaters, lighting, outside vents, windows, heating, ventilation, air conditioning (HVAC) systems, automated vacuums (rumbas), fans, etc. Other recommendations may include removing allergenic plants, change filters, perform maintenance, limit outside activity, etc. The environment recommendations may also be based on current weather conditions or forecast. For example, on a hot, humid day with a high mold count, the environment recommendations may include activating a dehumidifier and decreasing temperature settings.

The health recommendations and environment recommendations are transmitted to the UE 420 associated with the user at 910. The user may determine to manually change settings of one or more devices in response to the environment recommendations. In another embodiment, the UE 420 may be integrated with home or office systems and automatically control one or more devices in the facility in response to the home automation recommendations. For example, the UE 420 may be integrated with or configured to control the HVAC to automatically control the temperature or humidity of a location in response to the environment recommendations. In another example, the UE 420 may automatically control settings in a vehicle, such as open windows, increase fan speed, temperature, etc. In some embodiments, the UE 420 may automatically control one or more devices at the user location include one or more of: a thermoset, humidifier, dehumidifier, lighting, vent, window, ventilation system, automated vacuum, fan, heating system, air conditioning system, or home automation system.

In an embodiment, the health recommendation and environment recommendations may have a plurality of tiers depending on the severity of the user's symptoms, particle counts and/or types of allergens. A first tier of recommendations is provided to the user at a first time interval upon reports of mild user symptoms, usual type of allergens and average to lower particle counts. The first tier may include an over-the-counter medication and controlling existing at home equipment, such as HVAC settings. If the user reports continued symptoms at a second time interval, e.g., that are similar or heightened, or the particle count increases of a certain type of allergen, a second tier of recommendations may be provided to the user. For example, the second tier may be a recommendation for increase or change of allergy medication, obtaining an air filter or other new equipment, wearing a mask, limiting outside activity, contacting a medical professional, etc. A third tier of recommendations may include contacting emergency response (911 call) or immediately travel to an emergency room. The second or third tier of recommendations may be provided first to a user depending on the severity of the user's symptoms, particle counts or types of allergens. For example, for high pollution days, a second-tier recommendation maybe provided or if a user reports trouble breathing, a third-tier recommendation may be provided.

Figure 10:
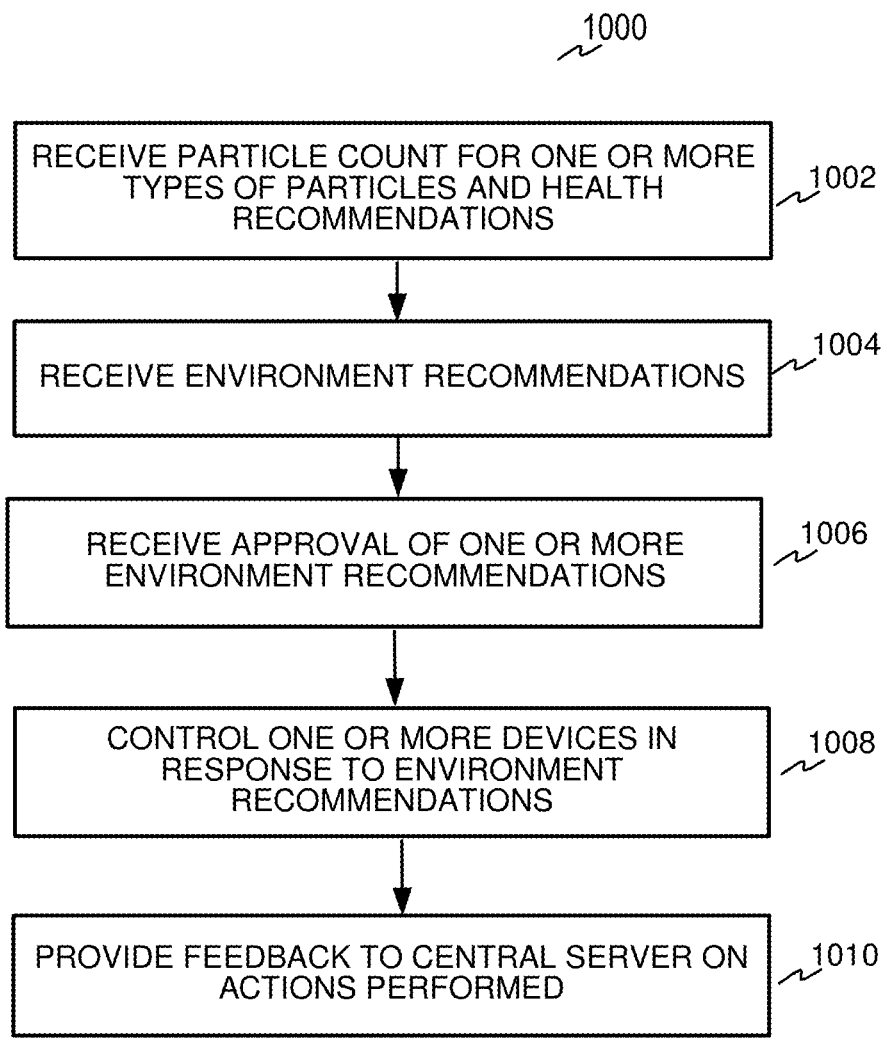
FIG. 10 illustrates a schematic block diagram of a method for controlling one or more devices at a user location in response to environment recommendations.

FIG. 10 illustrates a schematic block diagram of a method 1000 for controlling one or more devices at a user location in response to environment recommendations. The UE 420 includes a health monitoring application 520 that includes a dashboard or other display of allergens. The UE 420 receives a particle count for one or more types of particles and health recommendations at 1002 and updates the dashboard and may provide an alert to the user. The UE 420 may also receive environment recommendations in response to the type of allergen and particle count at 1004. The UE 420 may request approval of one or more of the environment recommendations at 1006. Upon receiving an indication of approval, the UE 420 may control one or more devices at the user location in response to the environment recommendations at 1008. In another embodiment, the UE 420 may automatically control one or more devices at the user location in response to the environment recommendations without user approval. In another embodiment, the central server 400 may communicate with a central management facility to control devices in an environment. For example, the central server 400 may communicate with a hospital facility system to increase or decrease temperature, humidity, air flow, etc.

In an embodiment, the UE 420 may provide feedback to the central server 400 on actions performed at 1010. For example, the UE 420 may provide feedback that temperature settings were changed but outside windows were not opened (e.g., windows may not be present or opened at the location). The central server 400 may then alter environment recommendations in the future, such as increase fan speeds in an HVAC system rather than open windows. The UE 420 or the central server 400 may thus communicate with one or more devices in a user location in response to environment recommendations.

Figure 11:
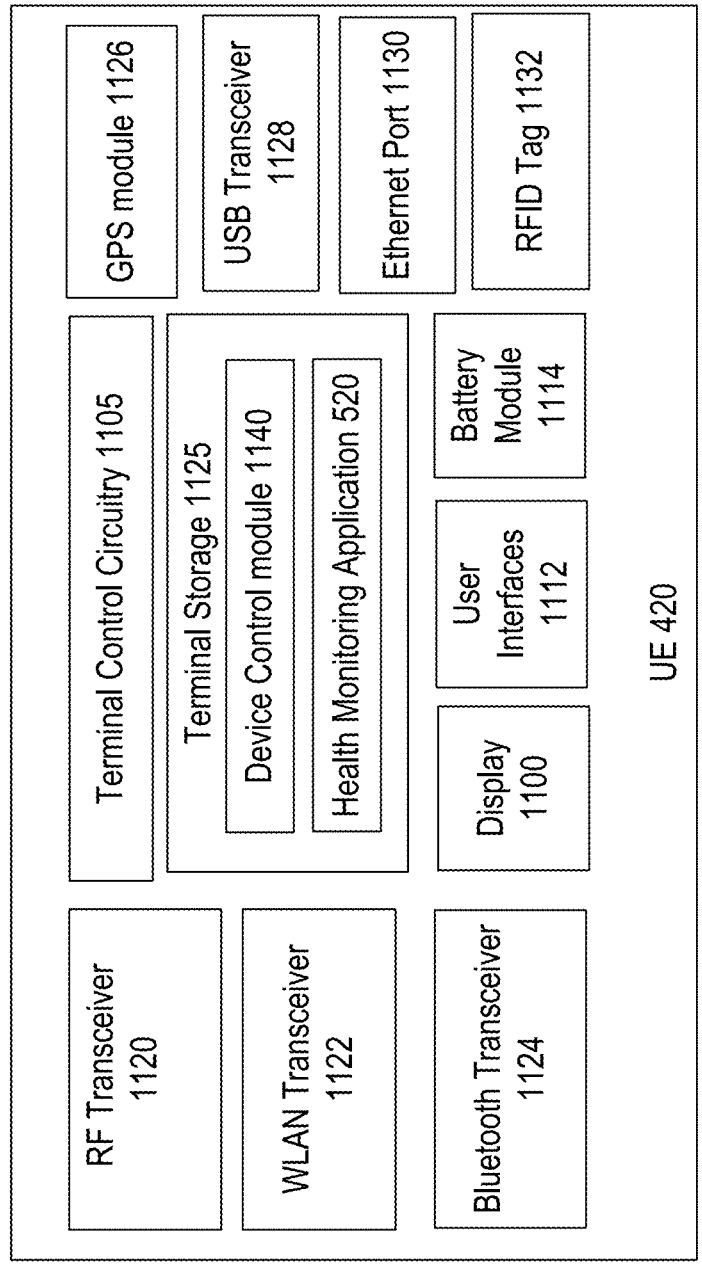
FIG. 11 illustrates a schematic block diagram of an embodiment of user equipment (UE)

FIG. 11 illustrates a schematic block diagram of an embodiment of user equipment (UE) 420. The UE 420 may include a smart phone, smart tablet, laptop, smart watch, desktop, TV, vehicle, or other electronic device. The UE 420 includes terminal control circuitry 1105. The terminal control circuitry 1105 includes a processing circuit having one or more processing devices, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions.

Connected to the terminal control circuitry 1105 is a display 1100. The display 1100 is an example of a user interface which allows the user to interact with the UE 420. The display 1100 may include a touchscreen, LED or other type of display. The display 1100 may be integrated in the UE 420 or may be separate to the UE 420. For example, the display 1120 may be a computer monitor, television screen, or head mounted display. The display 1120 enables a user to view data and graphical user interfaces (GUI) as described herein. The UE 420 may include or be operably coupled to one or more other user interfaces 1112 such as a mouse, keyboard, touchpad, voice recognition, or gesture recognition circuitry.

The UE 420 includes terminal storage 1125 that is connected to the terminal control circuitry 1105. The terminal storage 1125 may include one or more memory devices, such as a read-only memory, random access memory, volatile memory, non-volatile memory, static memory, dynamic memory, flash memory, cache memory, and/or any non-transitory memory device that stores digital information. In addition, the terminal storage 1125 may store one or more instructions or programs which when performed by the terminal control circuitry 1105 may control it to perform one or more functions described herein. The terminal storage 1125 stores a health care monitoring application 520 and device control module 1140. For example, the health care monitoring application 520 may instruct the terminal control circuitry 1105 to execute logic to direct the UE 420 to present one or more graphical user interfaces (GUI). The GUIs present data generated by central server 400 as well as GUIs to input user data and commands. The device control module 1140 is configured to control one or more devices at the user's location, such as an HVAC system or thermostat, humidifier, dehumidifier, automated vacuum, vents, windows, air purifiers, fans, etc.

The UE 420 may further include one or more of a Bluetooth transceiver 1124, a WLAN (IEEE 802.11x compliant) transceiver 1122, or a global positioning satellite (GPS) module 1126. The UE 420 may also include an RF transceiver 1120 compliant with Universal Mobile Telecommunications System (UMTS) Terrestrial Radio Access Network (UTRAN), Long Term Evolution (LTE) Evolved UTRAN (E-UTRAN), LTE-Advanced (LTE-A) or other wireless network protocols. The UE 420 may further include a USB port/transceiver 1128, Ethernet Port 1130 or RFID tag 1132. The UE 420 may also include a battery module 1114. One or more internal communication buses (not shown) may communicatively couple one or more of the components of the UE 420.

Figure 12A:
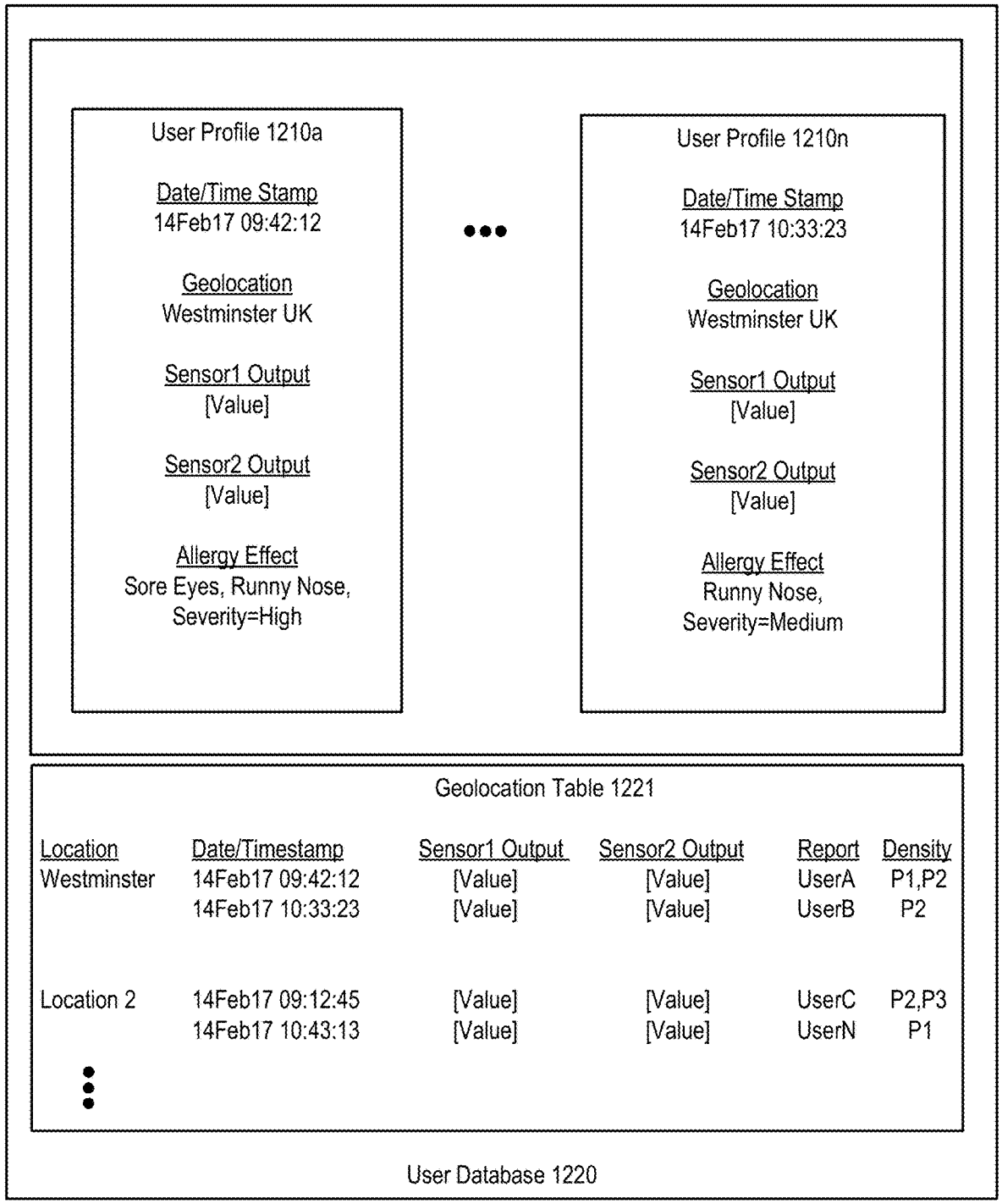
FIG. 12A illustrates a schematic block diagram of an embodiment of a user database.

FIG. 12A illustrates a schematic block diagram of an embodiment of a user database 1200. The user database 1200 includes a plurality of user profiles 1210a-n and a geolocation table 1221 that may be stored internally or externally to the central server 400. The user profiles 1210a-n include information for users registered with the health monitoring application 520 at the central server 400. Typically, this registration occurs when a user registers a UE 420 and/or a sensing device 100 with the health monitoring application 520 in the central server 400. The user typically downloads the health monitoring application 520 to the UE 420 or may access the application via a web server and website. The user profile 1210a-n may include known allergies, age, gender and other relevant medical history associated with that particular user. Additionally, particle counts and associated user symptoms are also stored within the user profile of user database 1200. In particular, the date and time of a particle count is stored along with the location of the sensing device 100. The location may include a borough, a city, a zip code, an address or GPS coordinates of the sensing device 100.

In addition, symptoms logged by the user of the UE 420 are also stored in correspondence with the particle counts. For example, in user profile 1210a, the symptoms logged by the user includes sore eyes and a runny nose. The user input also includes that the severity of these symptoms is a high severity. In other words, when the user is exposed to the particle count, the user suffers these symptoms with a high severity. The symptoms may be due to allergies or asthma or other health conditions.

The sensing device 100 may be configured to perform a measurement in accordance with one or more settings. For example, the sensing device 100 may be configured to capture images of particles periodically (for example every 15 minutes, 30 minutes, hour or the like). The sensing device 100 may be configured to capture images of particles at the same time every day (e.g., at 10 am, 11 am, 1 pm, 3 pm, etc.). The sensing device 100 may also be configured to capture images in response to a user logging symptoms with the UE 420 or upon request by a user of the UE 420.

The central server 400 then identifies the particles in the captured images and determines a particle count. The central server 400 determines a number of readings of a particular allergen per hour and an airflow within the sensing device 100. From this information, the central server 400 may obtain a concentration or count of a particular allergen or pollutant or other particulate with more accuracy. This information may be stored in the geolocation table 1221 as well. For example, a density of particles P1 and P2 is recorded for Westminster associated with a first sensing device 100 for UserA. A density of particles P2 is recorded for Westminster associated with a second sensing device 100 for UserB.

The geolocation table 1221 may thus include a density of one or more types of particles detected at each location (density of particles P1, P2, P3, etc.) during a time period. This record enables trends for particular locations to be monitored and data collated for local authorities and government to monitor allergens, pollutants and other particulates that may have an impact on public health. This is particularly useful where high levels of a pollutant such as fine particulate matter are reported in a particular residential location where the impact on public health may be significant. Further, as this data is collected from the sensing devices 100 which are, in embodiments, located in a dwelling, the local authorities and government will have data from inside dwellings. This kind of data is not normally accessible to public bodies and is actually more representative of the allergens and irritants to which people are exposed on a daily basis.

In addition to this information, an identifier of the sensing device 100 reporting this information is stored in association with the sensor measurement. The plurality of sensing devices 100 in a location allows local authorities to provide allergen counts, from, for example a street or region level of a city. In addition, this allows other user's sensing devices in this particular locality to provide crowd sourced information relating to pollutants and allergens within a user's home and locality. This collective information may be useful for users traveling to different locations or cities.

FIG. 12B illustrates a schematic block diagram of an embodiment of a recommendation database 1230. The recommendation database 1230 includes a plurality of health and environment recommendations 1240 that may be stored internally or externally to the central server 400. The recommendation database 1230 stores recommendations in response to one or more types of particles and particle count. The recommendations are provided to a UE 420 associated with a user and displayed on a terminal display 1100.

A user may input one or more symptoms and a severity of symptoms in a GUI of the health monitoring application 520 using the UE 420. The database lists associated health advice and environment recommendations for the input symptoms, severity of symptoms and type of allergen or other particulates.

The health advice is pre-stored, e.g., based on medical assistance. For example, the health monitoring application 520 obtains an identification of various particles (allergens, pollutants or other types of particles) and stores corresponding symptoms input by a user associated with those pollutants and allergens. Depending upon the severity of symptoms identified by the user, using either the UE 420 or the sensing device 100, appropriate health advice to reduce the impact of the identified particle that is pre-stored in the recommendation database 1230 is returned to the UE 420. In addition, environment recommendations to lower the level of the type of particle is provided. The recommendations may also be based on weather conditions and allergen forecasts as well.

In other instances, contact details for a medical practitioner (who specializes in the particular allergy and who is in the location of the user) are provided in addition to or instead of the advice. This may be appropriate, e.g., if the user is suffering severe allergic symptoms. Indeed, the user history and current symptoms and severity from the user database 1200 may be simultaneously provided to the medical practitioner. This will alert the medical practitioner to the user's allergic reaction and the allergens present in their surroundings. This may assist in the medical treatment given to the user. In really severe cases, the emergency services may be automatically dispatched to the geolocation of the user.

The network of sensing devices also allows the system to compare levels of allergen and pollutants between an indoor area of the user and an outdoor area near a user. For example, the health advice may include a caution to limit outdoor activity when the outdoor levels of allergen and pollutants are higher than indoor levels based on such comparison. Users with asthma, COPD or other health conditions may then determine to limit outdoor activity.

The health advice and environment recommendations may also be based on forecasts of weather conditions and particle counts. For example, birch pollen may rise with temperature while thunderstorms and humidity increase pollen levels. The sensing devices 100 may also include pollution detectors, temperature sensors, humidity detectors, etc. to assist with determining other factors for providing health advice and environment recommendations.

In other embodiments, a sensing device 100 such as, for example, described in FIG. 1, may detect airborne particles, such as allergen levels in the surrounding environment, that may be deposited on a collection plate. The sensing device 100 may send the data to a cloud network 410 for analysis. The data analysis regarding the allergen levels then may be sent to a dashboard or mobile display or application, such as described, for example, in GB 2560542 (Najjar), incorporated herein by reference in its entirety, where the end user may check the data. Upon checking the data on the dashboard, mobile display, mobile application, or the like, the user is provided custom recommendations—based on, at least in part on, the allergen levels and other environmental factors such as temperature, humidity, etc.—to reduce the allergen load and other actions to protect their health. In other embodiments, after receiving the allergen analysis data, the user may log their symptoms into the dashboard or mobile application (e.g., the health monitoring application 520 and display) and an algorithm may link the symptom log with the allergen data to provide a statistical analysis of the cause of the symptoms. In this way, the mobile application or the like may be tailored to each end user by taking into account the allergen other airborne particle, the amount of the allergen or airborne particle in the surrounding environment, and the environmental conditions to generate a specific recommended course of action to reduce the allergen or airborne particle load.

Figure 13A:
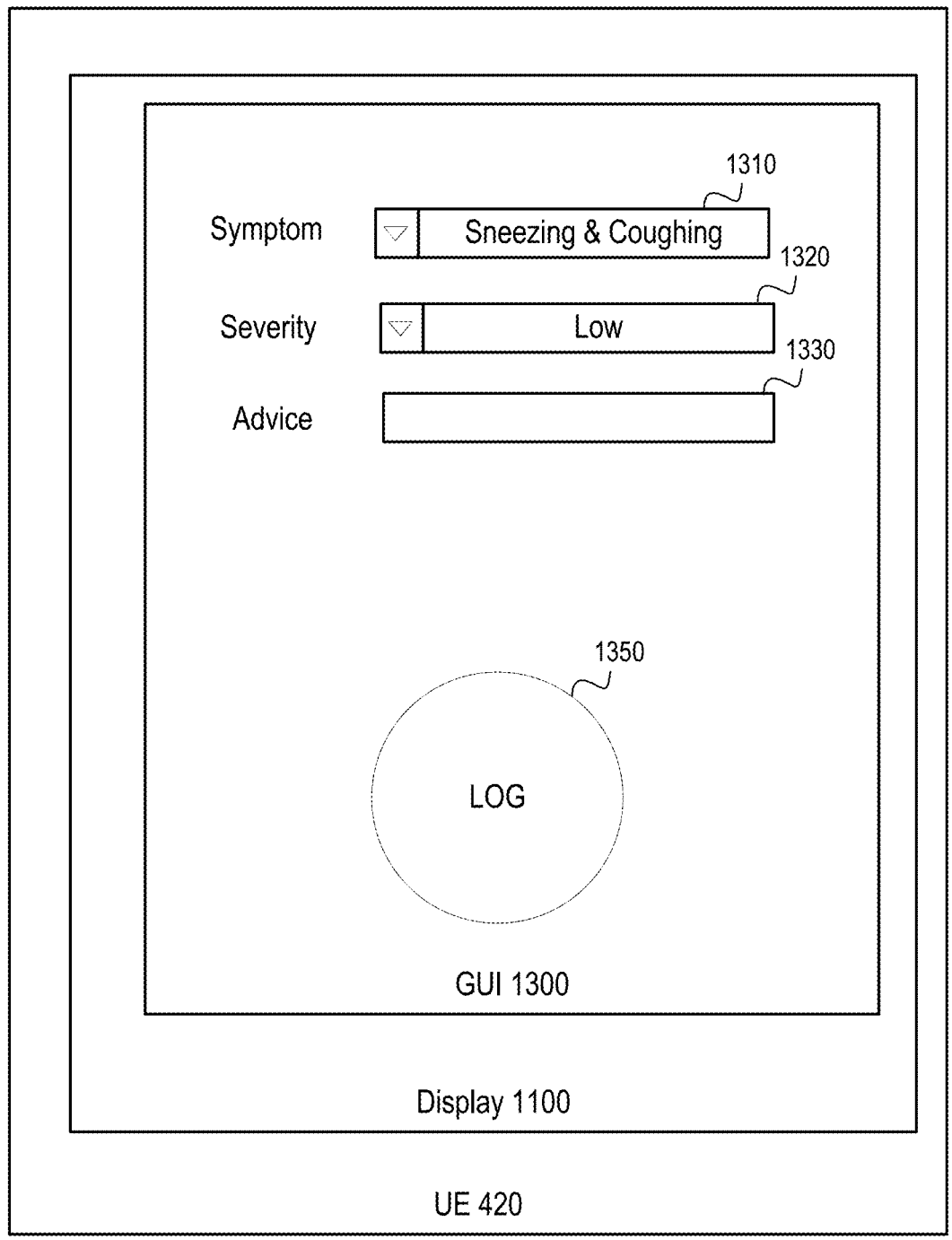
FIG. 13A illustrates a schematic block diagram of an embodiment of a graphical user interface.

FIG. 13A illustrates a schematic block diagram of an embodiment of a graphical user interface 1300. The graphical user interface 1300 may be generated by a UE 420 or central server 400 using the health care monitoring application 520. Referring to FIG. 13A, a UE 420 having a display 1100 with a graphical user interface (GUI) 1300 is shown. Using this GUI 1300, a user may select one or more symptoms.

In this example embodiment, the GUI 1300 includes a dropdown menu highlighting various symptoms though other types of user interface are envisaged such as fields to manually type in symptoms. The GUI 1300 also includes a dropdown menu for selection of a severity of allergic symptoms 1320. In this example, the user has indicated that their symptoms include sneezing and coughing, and the symptoms are of a low severity.

Figure 13B:
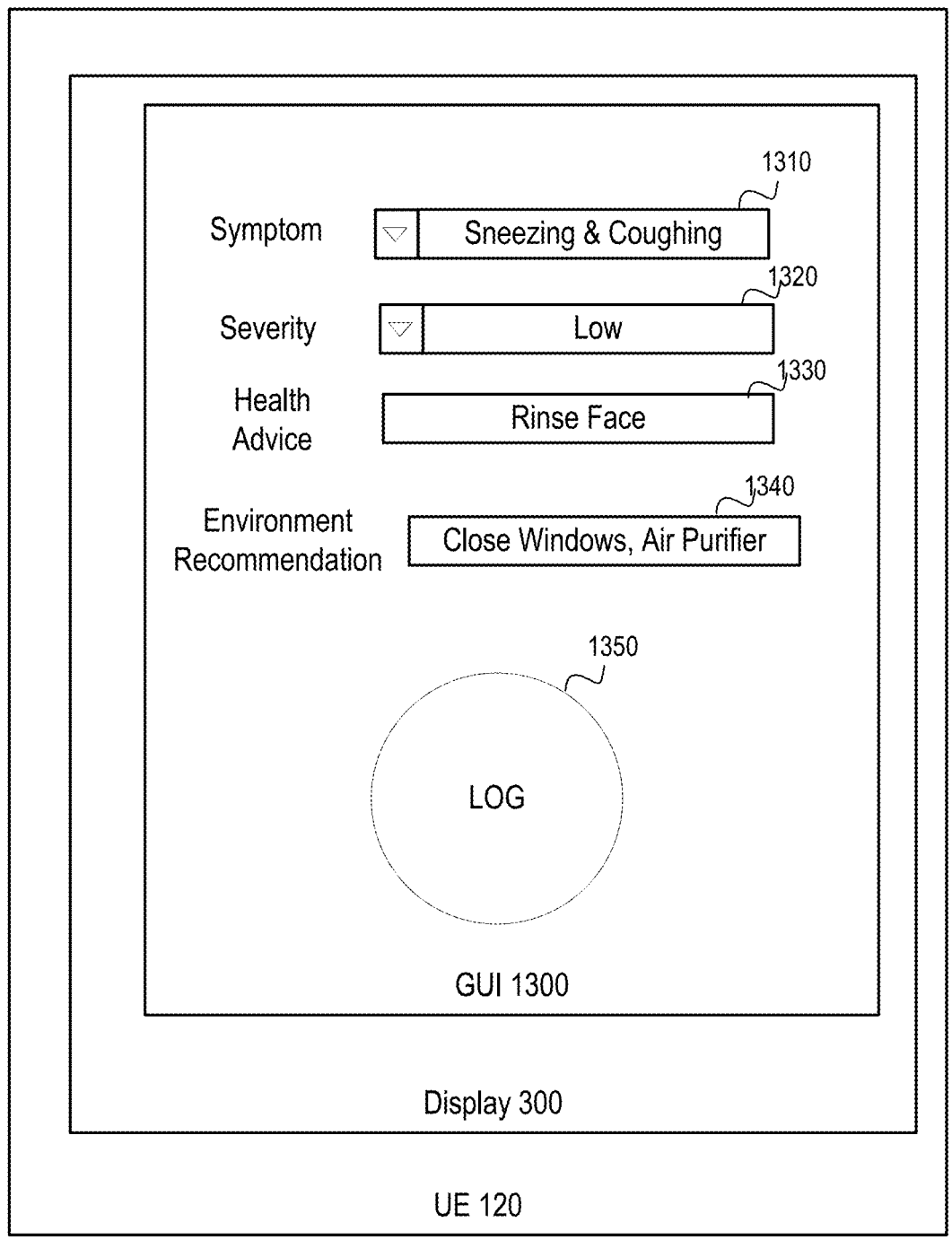
FIG. 13B illustrates a schematic block diagram of another embodiment of the GUI.

FIG. 13B illustrates a schematic block diagram of another embodiment of the graphical user interface 1300. The GUI 1300 further includes an initiate or "log" button 1350. The user database 1200 is accessed and based on the identified one or more particles and the symptoms, recommendations are then returned to the UE 420 by the central server 400. The health advice appears in field 1330, e.g., to rinse face. The environment recommendations are provided in field 1340, e.g., close the windows and activate an air purifier. In an embodiment, the UE 420 may automatically control the air purifier and close windows or wait for user approval.

The user may also provide an input of symptoms and the impact on his or her daily activities. For example, the symptoms may impair sleep, restrict the ability of the user to work or play sport etc. In other words, the severity of the outbreak may be judged. When the user logs this information, the central server 400 determines the levels of one or more of pollution, allergen and environmental factors (such as temperature, humidity, etc.).

This information from one or many users is then analyzed using a statistical tool, such as Principle Component Analysis, to determine one or more particulates that correlate with the logged symptoms. The central server 400 may then determine which one or more particulates (pollution, allergen or other environmental factor) are likely causes of the symptoms. This information allows the user to be aware of the factor or allergen that is causing his or her symptoms. These symptoms may be stored in the user database 1200 in association with the user and the associated one or more particulates. Accordingly, this information allows the user to identify the allergens that cause various symptoms for the user. This information is useful if the user is to attend a medical clinic as the clinician can review the symptoms experienced by the user and identify the allergen or factor present at the time of the symptom appearing and the time of day that the symptom appeared. This health monitoring application 520 may thus be used as an allergy diary. The health monitoring application 520 records the allergen and/or other factors and the symptoms for the user.

In addition, in embodiments, prediction of long-term allergy or asthma symptoms is performed by the health monitoring application 520. Specifically, once the allergen and other factors which trigger a user's symptoms are determined, future symptoms over the next few days, weeks and months can be predicted. In order to achieve this, long term weather and pollution forecasts are used, in conjunction with historical data, to predict the fluctuation in levels of pollution and allergen for a given geolocation. This information is used to indicate to a user (based at a geolocation) whether they will suffer allergic symptoms over the next few days, weeks or months. Additionally, advice may be provided to the user in order to reduce the severity of the symptoms or even avoid the outbreak altogether by improving the air quality. In summary, the health monitoring application 520 may notify or warn the user of a possible long-term allergen issue in advance. This warning allows preventative advice to be provided to the user.

In addition, during a periodic check of the environment, when a particular allergen or the amount of the particular allergen is above a certain level, the central server 400 can push a warning to the user. The warning may include health advice about how to reduce the impact of the allergen or may include advice describing how to reduce the amount of the allergen in the user's environment. This warning, therefore, allows the user to take preventative measures to avoid the symptoms associated with the allergen before those symptoms are exhibited.

The central server 400 may also generate a personal report on how the severity of symptoms of a user rank vs. other users in the same or other cities. The report may also provide an accuracy level of forecasts. The personal report may provide an indication of the impact of allergens on quality of life of the user.

Although the above describes the provision symptoms and severity level by the user, the health advice may not require this information in order to return health advice to a UE 420. The central server 400 may provide general health advice and environment recommendations based on particle counts and reactions of a generic population to such particles. Although the foregoing describes advice related to allergies and asthma, any kind of advice, warnings or data may be implemented.

Figure 14:
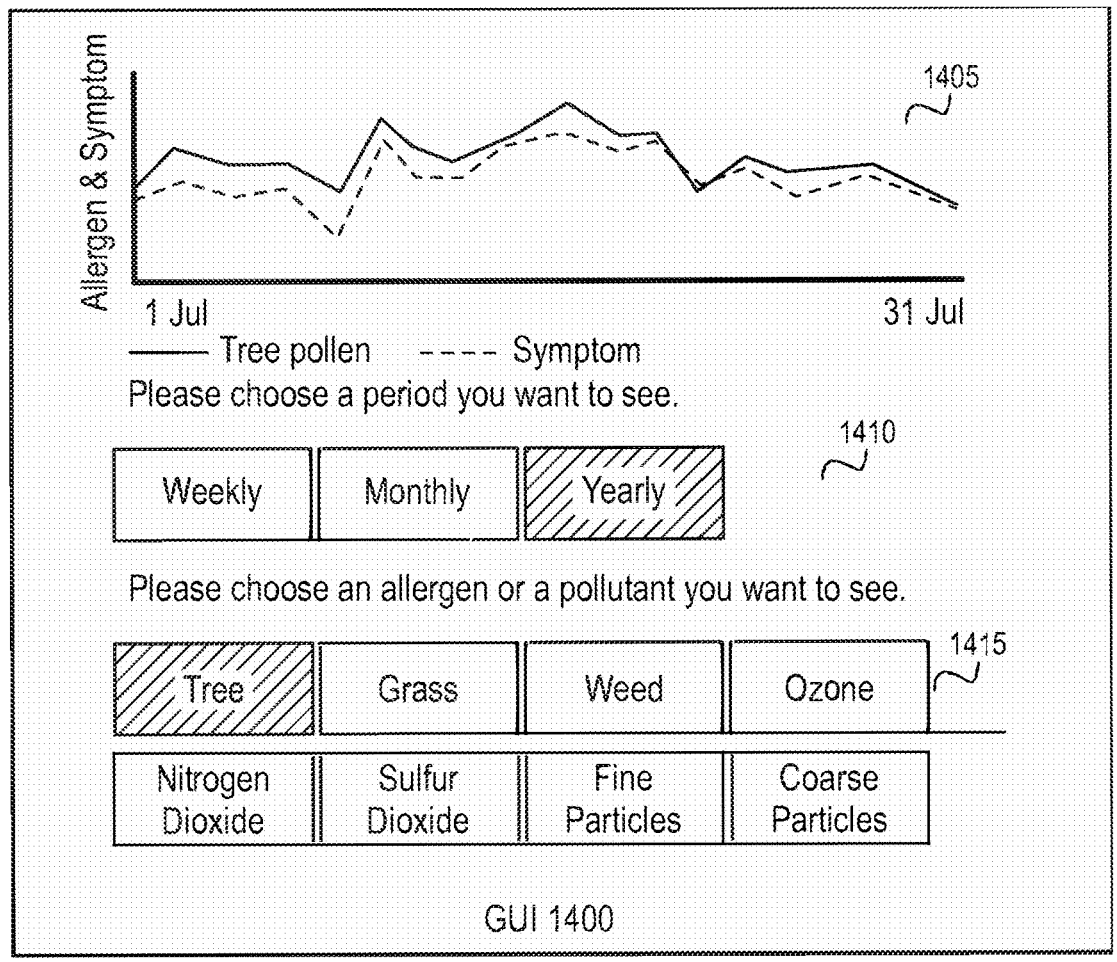
FIG. 14 illustrates a schematic block diagram of an example of another GUI that may be generated using the health monitoring application 520.

FIG. 14 illustrates a schematic block diagram of an example of another GUI 1400 that may be generated using the health monitoring application 520. In this example, the health monitoring application 520 at the UE 420 and/or central server 400 may provide data for and direct a UE 420 to display a graph 1405 including a presence/severity of symptoms and a concentration of a particulate. In this example graph 1405, the density of tree pollen over a period of one month is displayed. The severity or presence of symptoms logged by a selected user of the UE 420 is displayed. The graph 1405 may thus illustrate a correlation between density of a particulate and the presence and/or severity of symptoms of the selected user. The GUI 1400 may include a user selection for input of a time period for display, e.g., such as a weekly graph, a monthly graph or yearly graph. The GUI may also include a user selection for input of one or more allergens or pollutants or other particulates to be displayed in the graph 1405.

Figure 15:
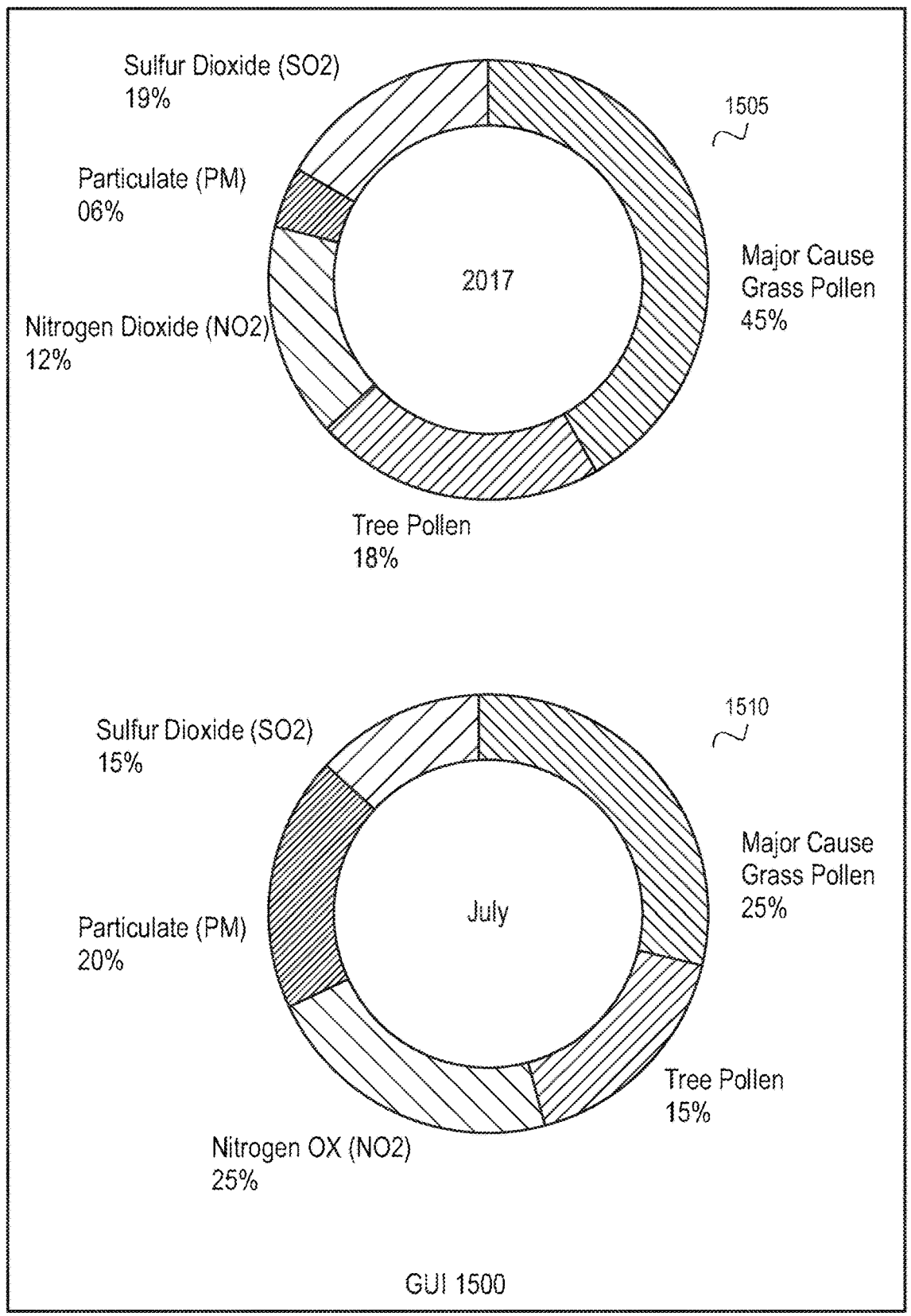
FIG. 15 illustrates a schematic block diagram of an example of another GUI that may be generated using the health monitoring application 520.

FIG. 15 illustrates a schematic block diagram of an example of another GUI 1500 that may be generated using the health monitoring application 520. The health monitoring application 520 on the UE 420 and/or central server 400 correlates logged symptoms and severity of symptoms of a user with identified particulates. For example, the health monitoring application 520 may provide data for and direct a UE 420 to display a graph 1505 including concentration of particulates detected at times that a user logged having symptoms during a year. In the graph 1505, the density of particulates detected during symptomatic conditions during 2017 is displayed. The severity or presence of symptoms of a selected user of the UE 420 is correlated with the density of particulates detected over the year and a percentage of the particulates identified that may be causes of the symptoms over the period.

For example, the graph 1505 shows that a major cause of symptoms during 2017 may be grass pollen at 45% and then sulfur dioxide at 19% and tree pollen at 18%. The graph 1505 shows that a major cause of symptoms during a monthly period of July may be grass pollen at 25% and nitrogen dioxide at 25% and then other particulates at 20%. The health monitoring application 520 520 may thus determine and display data showing the correlation between various particulates and the presence and/or severity of symptoms logged by a user over a period of time. Again, the GUI 1400 may include a user selection for input of a time period for the display, e.g., such as a daily graph, weekly graph, a monthly graph or yearly graph.

Figure 16:
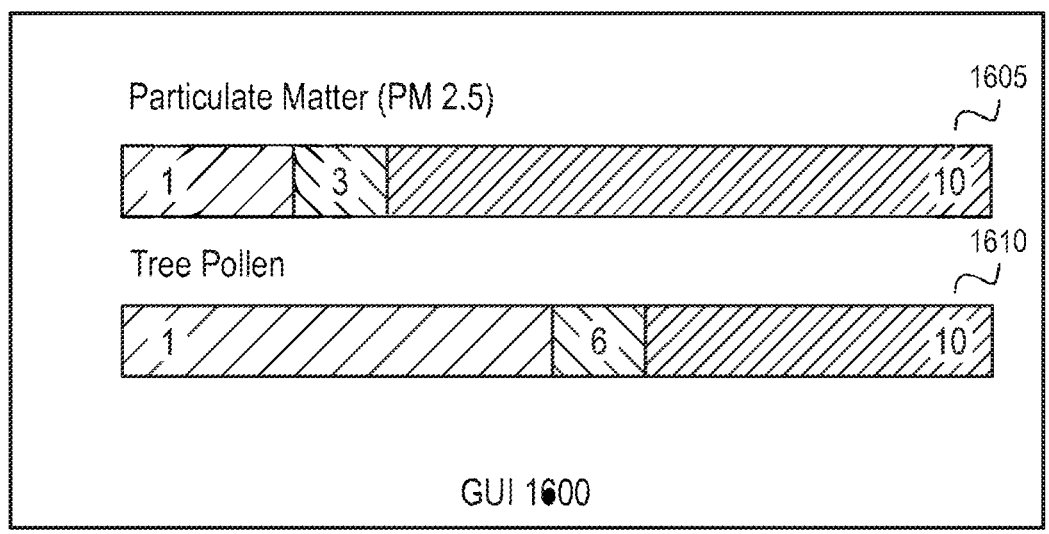
FIG. 16 illustrates a schematic block diagram of an example of another GUI that may be generated using the health monitoring application 520.

FIG. 16 illustrates a schematic block diagram of an example of another GUI 1600 that may be generated using the health monitoring application 520. The health monitoring application 520 on the UE 420 and/or central server 400 correlates logged symptoms and a minimal level of one or more types of particulates present when the symptoms are logged by a user. The symptoms of the user are thus correlated with a minimum concentration of identified particulates in which the logged symptoms were reported. The health monitoring application 520 may then provide data for and direct a UE 420 to display a GUI 1600 including a minimum concentration of a type of particulate detected when a user inputs having symptoms over a requested time period, such as a week, month or year.

For example, the graph 1605 includes a minimum concentration of a type of particulate matter (e.g., 3 PPM) detected when a user inputs having symptoms. The graph 1610 includes a minimum concentration of tree pollen (e.g., 6 PPM) detected when a user inputs or logs having symptoms. The graph 1605 and graph 1610 may thus help predict a minimal level of a particulate that may trigger symptoms in the future.

Figure 17:
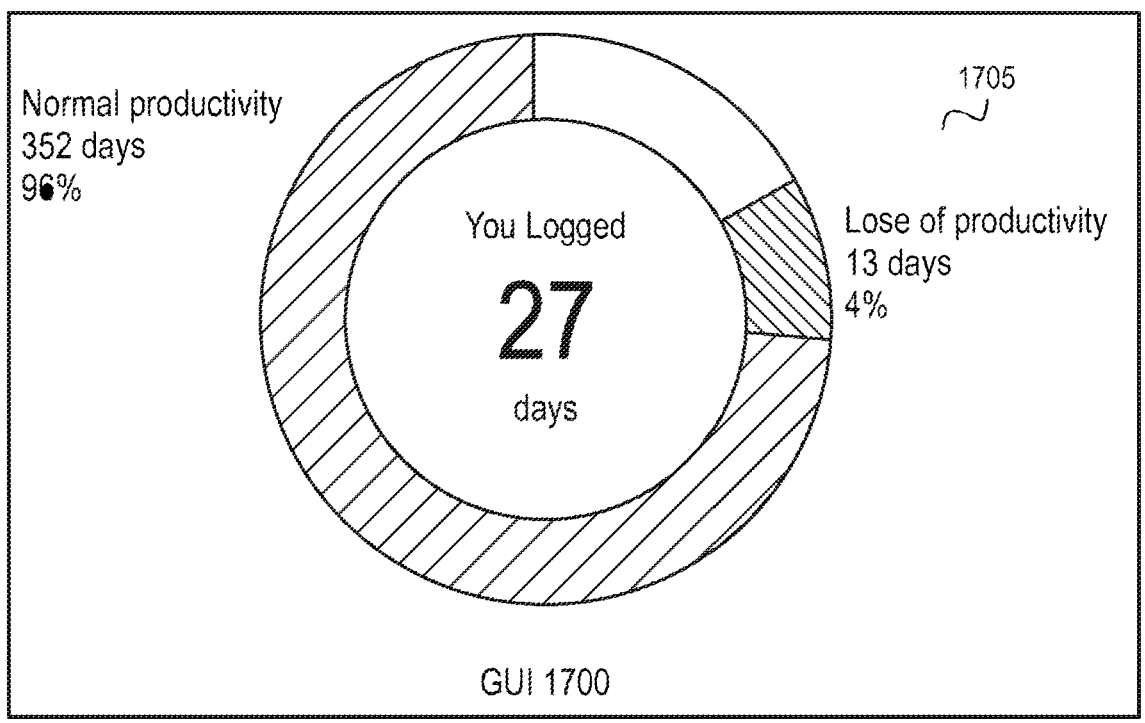
FIG. 17 illustrates a schematic block diagram of an example of another GUI that may be generated using the health monitoring application 520.

FIG. 17 illustrates a schematic block diagram of an example of another GUI 1700 that may be generated using the health monitoring application 520. The health monitoring application 520 on the UE 420 and/or central server 400 correlates logged symptoms and resulting loss of productivity over a time period. The symptoms of a user are correlated with a typical loss of productivity due to such symptoms. Alternatively, or in addition thereto, a user may input loss of productivity due to symptoms. For example, the health monitoring application 520 may provide data for and direct a UE 420 to display a graph 1705 including loss of productivity over a period of time.

Figure 18:
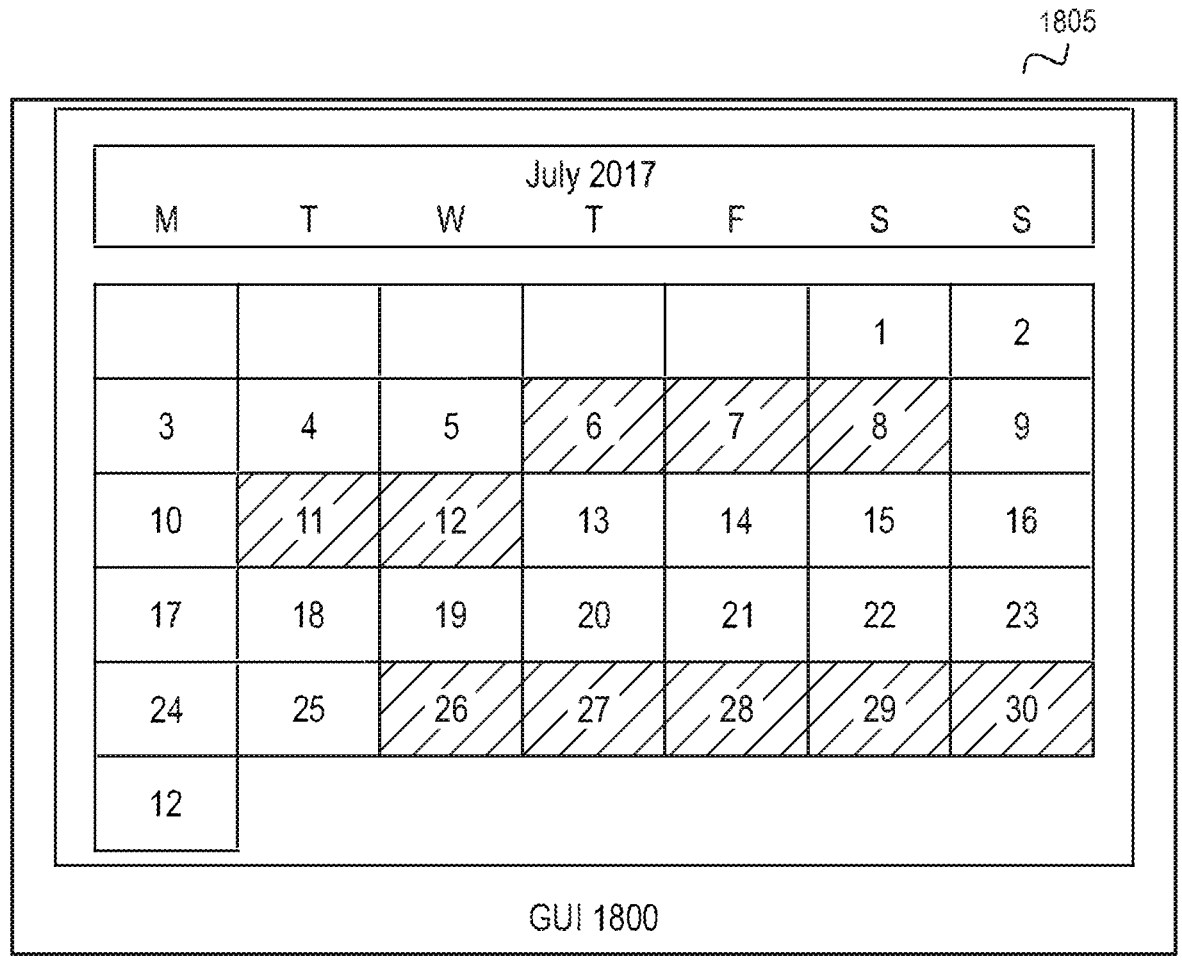
FIG. 18 illustrates a schematic block diagram of an example of another GUI that may be generated using the health monitoring application 520.

FIG. 18 illustrates a schematic block diagram of an example of another GUI 1800 that may be generated using the health monitoring application 520. The health monitoring application 520 on the UE 420 and/or central server 400 stores and tracks a number of times a user logs intaking medication. The health monitoring application 520 may display a calendar 1805 correlated with a typical loss of productivity due to such symptoms. The user may input medication taken due to symptoms. For example, the health monitoring application 520 may provide data for and direct a UE 420 to display a calendar 1805 indicating days in which medication was logged as taken by a user. The calendar 1805 may thus help predict days in a month or year in symptoms are triggered in the future.

The health monitoring application 520 from the UE 420 or central server 400 may transmit data to a healthcare provider 195. For example, one or more of the reports or data described herein may be transmitted to a healthcare provider 195. The healthcare provider 195 may provide health advice or medication using such data.

Figure 19:
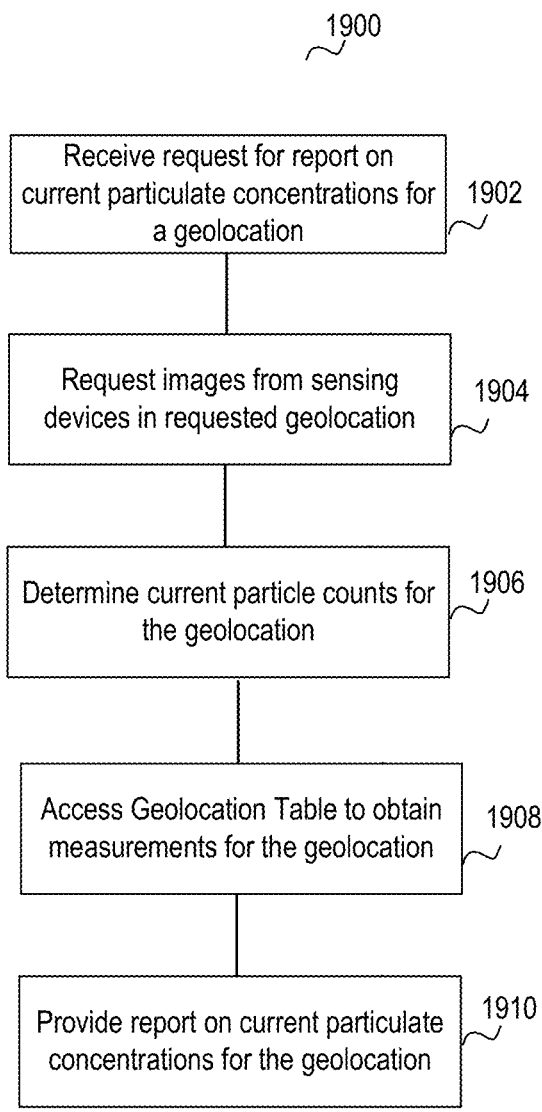
FIG. 19 illustrates a logical flow diagram of an embodiment of a method for providing a concentration of particles in the air at a geolocation.

FIG. 19 illustrates a logical flow diagram of an embodiment of a method 1900 for providing a concentration of particles in the air at a geolocation. For example, a user who is traveling to a different city or country may request a current update on concentrations of any potential allergens in the city or country. The user may thus prepare with medications or other remedies for any known allergens. The user inputs the request using the health monitoring application 520 on a UE 420 for a report on current or forecasted particle concentrations or counts for a geolocation. The request may be for one type of particle (e.g., pollen, ragweed, or mold) or a general report on the types of particulates identified in the geolocation. The UE 420 transmits the request to the central server 400. The central server 400 receives the request at 1902 and obtains a current report for the geolocation, e.g. based on images from one or more sensing devices 100 in the geolocation over the past minutes, hours, or 24 hours. In one embodiment, the central server 400 requests current images from sensing devices in the requested geolocation at 1904. The sensing devices 100 may capture images upon receiving the request and provide the images to the central server 400. The central server 400 may then process the images and determine current particle counts for the geolocation at 1906.

Additionally, or alternatively, the central server 400 may access the geolocation table 1221 to obtain stored measurements for the geolocation at 1908. For example, the central server 400 may determine from time stamp that particle counts have been determined in the geolocation within a predetermined time period (e.g., within one minute or one hour). Since the measurements are current within an acceptable predetermined time period, the central server 400 may then provide a report based on the stored particle counts from the user database 1200. The central server 400 may use a combination of both methods. For example, the central server 400 may determine that certain sensing devices 100 in the geolocation have current measurements (e.g., within the hour) but that other sensing devices 100 in the geolocation have not provided current images. The server 100 may request current images only from these sensing devices 100.

The central server 400 thus obtains current particle counts in the geolocation and provides a report on current particle counts in the geolocation at 1910. The central server 400 may average or mean the measurements using the images from each of the sensing devices 100 to provide the report or provide a range of the particulate concentrations based on the measurements in the geolocation to the requesting UE 420.

In addition, the central server 400 may provide a report on current particulate concentrations for different locations within a same city or country. For example, the central server 400 may provide a map illustrating different concentration levels of a particulate outside a building, street, in different regions of a city or a country.

Figure 20:
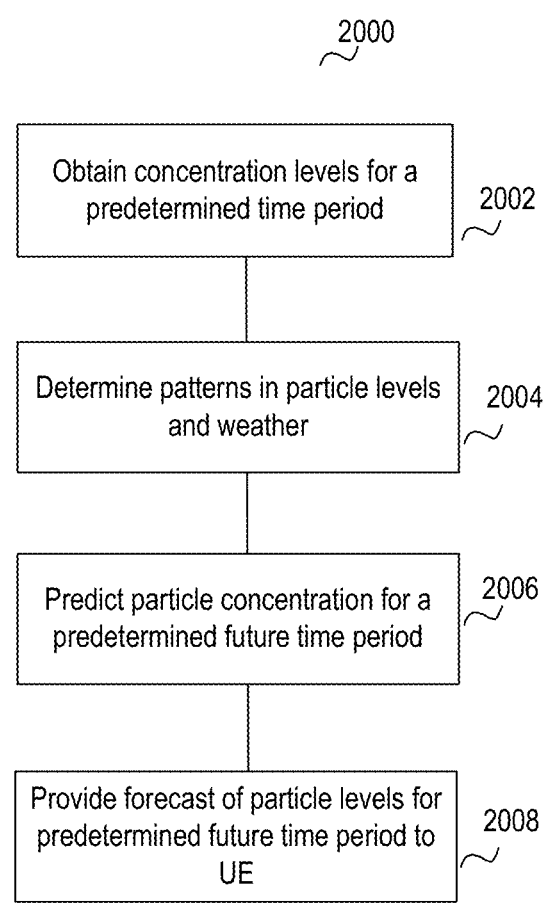
FIG. 20 illustrates a logical flow diagram of an embodiment of a method for providing a forecast of particle levels in the air at a geolocation.

FIG. 20 illustrates a logical flow diagram of an embodiment of a method 2000 for providing a forecast of particle levels in the air at a geolocation. A forecast may be provided for a specific site of a sensing device 100, e.g., inside a dwelling or business or for an outside location of a sensing device 100. In another embodiment, a forecast may be provided for a geolocation over a location of a plurality of sensing devices 100. The forecast may be determined by the central server 400 using the sensor outputs of one or more of the plurality of sensing devices 100 and using weather forecasts. The forecast predicts the particle concentration levels for a predetermined future time period. The particle concentration levels may include pollutant levels or allergen levels, such as pollen levels, ozone levels, etc. The future time period may include, e.g., a one-day forecast, two-day forecast or three-day forecast.

To determine the forecast, concentration levels for a predetermined time period are obtained at 2002. For example, the current and past particle concentration levels for one or more days or weeks are obtained for the geolocation. The past concentration levels for the same days or weeks in one or more past years may also be obtained. The concentration levels are graphed versus time and versus weather, and particle levels generated for the predetermined time periods and weather conditions.

Patterns in the particle level signals are obtained at 2004. For example, trends, noise or periodicity of the particle level signals are determined based on time of year and weather. Based on past patterns, particle levels for a predetermined future time period are predicted at 2006. Forecasts for one to three days are generally more accurate than forecasts for longer time periods. An accuracy level for the forecast may also be determined.

The forecast of one or more particle levels for the predetermined future time period are provided to a user at 2008. The health monitoring application 520 may display the forecasts on GUI of the UE 420 upon request or may push automatically for display on UE 420.

Numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed, the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provide an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Statement of the Certain Embodiments of the Invention

1. In a first embodiment, a sensing device, comprises: a collection plate; a fan configured to generate air flow through a receptacle of the sensing device; a collection plate, wherein the air flow guides particles in the air flow towards the collection plate; an imaging device configured to capture images of the particles situated on the collection plate; and a control device configured to control a speed of the fan to generate the air flow, wherein the speed of fan is determined using a location of the sensing device.

2. The sensing device of embodiment 1, further comprises a transceiver configured to: communicate over one or more networks to a central server; and process a command from the central server to control the speed of the fan, wherein the speed of the fan is determined and set by the central server using the location of the sensing device.

3. The sensing device of embodiment 1, wherein the speed of the fan is set to generate the air flow to approximate particle inhalation of a user in response to a residential location of the sensing device.

4. The sensing device of embodiment 1, wherein the speed of the fan is set to generate the air flow at approximately 7-9 liters per minute in response to a residential location of the sensing device.

5. The sensing device of embodiment 1, wherein the speed of the fan is set to generate the air flow at greater than 9 liters per minute in response to an industrial location of the sensing device.

6. The sensing device of embodiment 1, wherein the speed of the fan is set to generate the air flow at less than 7 liters per minute in response to an outside location of the sensing device.

7. The sensing device of embodiment 1, wherein the speed of the fan is lowered from its current speed setting in response to a rapid increase of particle density on the collection plate.

8. The sensing device of embodiment 1, wherein the speed of the fan is increased from its current setting in response to a slow increase of particle density on the collection plate.

9. In another embodiment, a central device, comprises: a network interface circuit configured to communicate over one or more networks to a sensing device; at least one processing device configured to: obtain a current image of a plurality of particles from the sensing device; determine a location of a first particle using the current image; compare the location of the first particle to locations of other particles in prior images from the sensing device; determine the location of the first particle is substantially same as a location of one of the other particles in prior images from the sensing device; discard a portion of the current image including the first particle; locate at least a second particle in the current image; and obtain a particle identification of the second particle in the current image.

10. The central device of embodiment 9, comprising: a health monitoring module configured to: receive logged symptoms of a user; and access a database to obtain health advice and environment recommendations associated with the logged symptoms of the user and the particle identification.

11. The central device of embodiment 10, wherein the environment recommendations include recommendations for controlling one or more devices at a user location to help lower a particle level.

12. The central device of embodiment 11, wherein the at least one processing device is further configured to communicate the health advice and environment recommendations to a user device.

13. The central device of embodiment 11, wherein the at least one processing device is further configured to automatically control one or more devices at a user location based on the environment recommendations.

14. The central device of embodiment 11, wherein the one or more devices at the user location include one or more of: a thermoset, humidifier, dehumidifier, lighting, vent, window, ventilation system, automated vacuum, fan, heating system, air conditioning system, or home automation system.

15. The central device of embodiment 15 wherein the one or more devices are activated or deactivated based on detection of an allergen and a concentration of the allergen.

16. The central device of embodiment 14 wherein the central device is integrated into the one or more devices.

17. The central device of embodiment 14 wherein the central device is located remotely from the one or more devices.

18. The central device of embodiment 9, wherein the identified second particle includes at least one of: an allergen, pollutant, or other type of airborne particulate.

19. In another embodiment, user equipment (UE), comprises: a transceiver configured to communicate over one or more networks to a central device; at least one processing device configured to: generate a GUI including a particle count of an allergen for a user location; receive a health recommendation and/or an environment recommendation from the central device to lower the particle count of the allergen from the user location, wherein the environment recommendation includes one or more of activating, deactivating, or adjusting a setting of one or more devices at the user location; and generate a command to activate, deactivate, or adjust the setting of the one or more devices at the user location based on the environment recommendation.

20. The UE of embodiment 17, wherein the one or more devices at the user location include one or more of: a thermoset, humidifier, dehumidifier, lighting, vent, window, ventilation system, automated vacuum, fan, heating system, air conditioning system, or home automation system.

System and Methods for Air Monitoring Using Sensor Devices

The disclosure also provides for a system and methods for air monitoring. As discussed above, FIG. 4 illustrates a schematic block diagram of an embodiment of an exemplary network 410. The exemplary network 450 includes one or more networks that are communicatively coupled, e.g., such as a wide area network (WAN) 470, a wired local area network (LAN) 460, a wireless local area network (WLAN) 430, and/or a wireless wide area network (WAN) 480. The LAN 460 and the WLAN 430 may operate inside a residence or in an enterprise environment, such as an office building, retail store, hotel, restaurant, clinic or other facility. The wireless WAN 480 may include, for example, a 3G or 4G cellular network, a GSM network, a WIMAX network, an EDGE network, a GERAN network, etc. or a satellite network or a combination thereof. The WAN 470 includes the Internet, service provider network, other type of WAN, or a combination of one or more thereof.

User equipment (UE) 420a, 420c may communicate over the network 410, e.g., to one or more other UE 420a, 420b, 420c or to one or more sensing devices 100a, 100b, 100c, to a server 400, to a healthcare provider 440, etc. The UE 420a, 420b, 420c may include a smart phone, laptop, desktop, smart tablet, smart watch, or any other electronic device.

Each of the sensing devices 100a, 100b, 100c are communicatively coupled to one or more of the UE 420a, 420b, 420c directly or through one or more of the exemplary networks. The sensing devices 100 are configured to identify and monitor various types of airborne particles in air samples from a location outside or inside. A sensing device 100a, 100b, 100c, may be in a residence or in an enterprise environment, such as a store, office, hotel, clinic, stadium, or other facility. The sensing devices 100a, 100b, 100c may also be located outside in parks, streets, highways, tops of buildings, etc. In addition, a sensing device 100a, 100b, 100c may be located on trains, cars, planes, or other modes of transportation. The sensing devices 100a, 100b, 100c are configured to monitor air samples and identify one or more types of airborne particles.

The sensing devices 100a, 100b, 100c may thus be used to detect levels of allergen and pollutants. For example, the sensing devices 100a, 100b, 100c may provide identification and levels of allergen and pollutants found locally outside, such as around a building, street, or one or more parts of a city. The sensing devices 100a, 100b, 100c may also provide identification and levels of allergen and pollutants found inside within a residence, workplace, retail center, factory, stadium, or other indoor area. Using the network, the identification and levels of allergen and pollutants found in other cities, states, countries or internationally may also be provided to users. The network of sensing devices also allows the users to compare levels of allergen and pollutants between an indoor area and outdoor area. Users with asthma, COPD or other health conditions may determine to limit outdoor activity when outdoor levels of allergen and pollutants are higher based on such comparison.

The identified airborne particles may include typical allergens such as pollen, ragweed, grass, rye, pet dander, birch, mold, *Artemisia*, etc. The identified airborne particles may also include pollutants, such as ozone, NOx, CO, Sox, etc. These listed types of particles are examples only and other types of particles may also be identified and monitored by the sensing devices 100a, 100b, 100c.

The server 400 includes a health monitoring application 520 health monitoring application 520 that may be installed on or operable to communicate with the UE 420a, 420b, 420c and sensing devices 100a, 100b, 100c. The health monitoring application 520 may be a web-based application supported by the server 400. For example, the server 400 may be a web server and support the health monitoring application 520 via a website. The UE 420a, 420b, 420c may access the functions and data of the health monitoring application 520 using a browser that accesses the server 400. In another embodiment, the health monitoring application 520 is a stand-alone application that is downloaded to the UE 420a, 420b, 420c and is operable on the UE 420a, 420b, 420c without access to the server 400 or accesses the health monitoring application 520 on the server 400 for additional information or data. The sensing devices 100a, 100b, 100c may also include the health monitoring application 520 or be operable to communicate with the server 400 to perform one or more functions described herein.

The one or more sensing devices 100a, 100b, 100c may communicate with the server 400 to perform one or more functions herein. Alternatively, the health monitoring application 520 and associated databases may be downloaded to a sensing device 100a, 100b, 100c such that the sensing device may be operable to perform one or more functions herein without communicating over the network 410.

Figure 21:
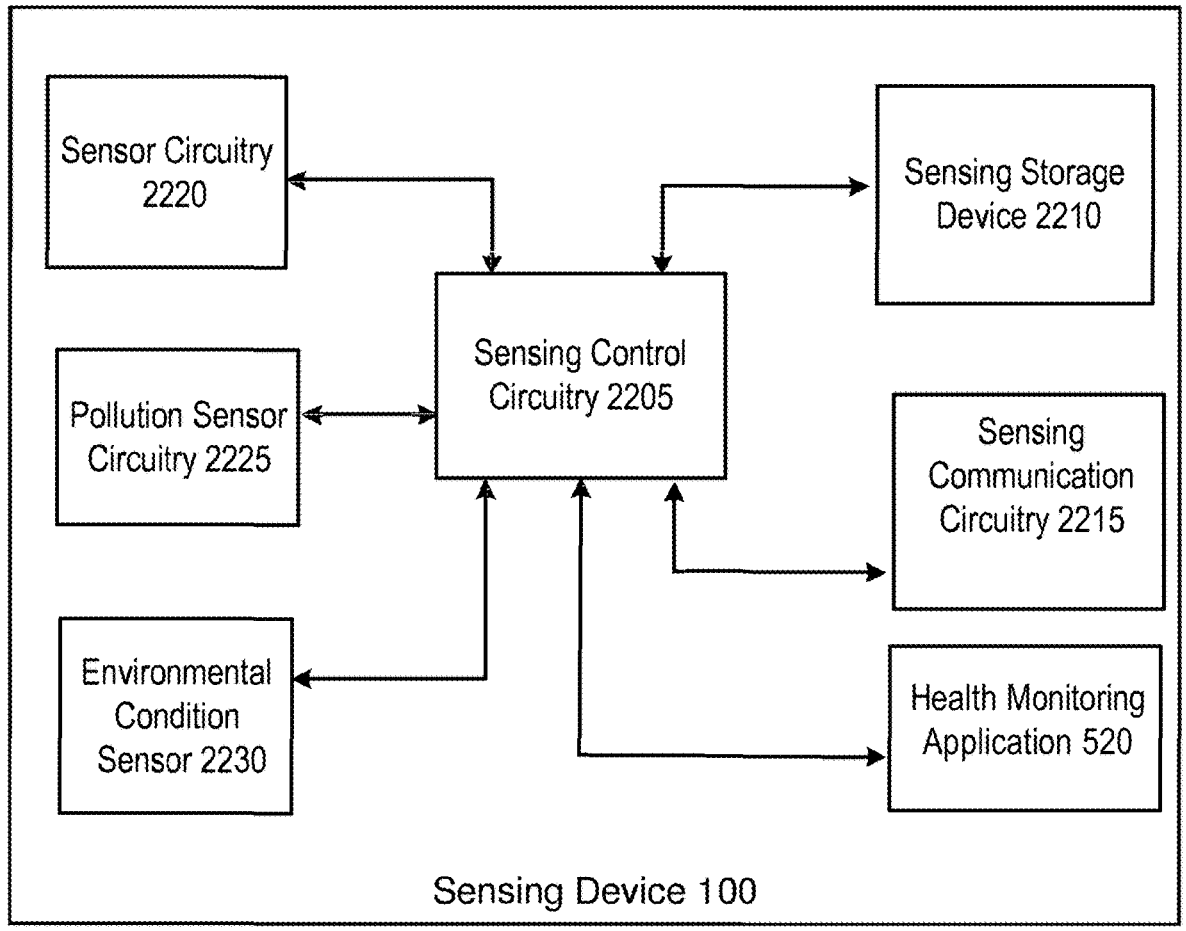
FIG. 21 illustrates 2 illustrates a schematic block diagram of an embodiment of exemplary sensing device.

FIG. 21 illustrates a schematic block diagram of an embodiment of a sensing device 2100. The sensing device 100 comprises sensing control circuitry 2105. The sensing control circuitry 2105 includes a processing circuit having one or more processing devices, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions.

The sensing device 100 further includes a sensing storage device 2110 that includes one or more memory devices, such as a read-only memory, random access memory, volatile memory, non-volatile memory, static memory, dynamic memory, flash memory, cache memory, and/or any non-transitory memory device that stores digital information. The sensing storage device 2110 stores one or more instructions or programs which when performed by the sensing control circuitry 2105, instructs the sensing control circuitry 2105 to control the sensing device 100 to perform one or more functions described herein.

The sensing storage device 2110 is connected to the sensing control circuitry 2105. The sensing storage device 2110 stores, e.g., the health monitoring application 520 and a database including user profile information and as will be explained further herein, particle signatures, associated symptoms and health advice. Information and data from this database may be provided to one or more of the UEs 420 to provide health information based on the detection and monitoring of types of particles by the sensing device 100.

Additionally connected to the sensing control circuitry 2105 is sensing communication circuitry 215. The sensing communication circuitry is configured to communicate with UE 420 or to the server 400 over one or more of the exemplary networks in the network 410. For example, the sensing communication circuitry 2115 may include a wired or wireless transceiver to communicate over a WLAN, WAN, or cellular network.

Further connected to the sensing control circuitry 2105 is sensor circuitry 2120. The sensor circuitry 2120 is configured to capture and analyze particles in air samples. In particular, the sensor circuitry 2120 may identify airborne particles that can trigger an allergic reaction. For example, the sensor circuitry 2120 is used to capture particles such as pollen or animal dander. These particles are captured by the sensing device in air samples from the habitat in which the sensing device 100a, 100b, 100c is located.

Additionally provided and connected to the sensing control circuitry 2105 is pollution sensor circuitry 2125. In a similar manner to the sensor circuitry 2120, the pollution sensor circuitry 2125 is configured to capture and analyze pollutants in the habitat in which the sensing device 100a, 100b, 100c is located. However, differently to the sensor circuitry 2120, the pollution sensor circuitry 2125 captures and identifies pollutants such as NOx and CO and other such pollutants. The sensor circuitry 2120 and the pollution sensor circuitry 2125 may include specially designed or off-the-shelf electrochemical or similar components, such as MEMs based sensors. Embodiments of the sensor circuitry 2120 and the pollution sensor circuitry 2125 are described in more detail herein.

In addition, the sensing device 100a, 100b, 100c may include an environmental condition sensor 2130. The environmental condition sensor 2130 includes various instruments, such as thermometer, barometer, etc. which measure environmental conditions such as humidity and temperature of the surroundings.

FIG. 11 illustrates a schematic block diagram of an embodiment of user equipment 420. The user equipment (UE) 420 may include a smart phone, smart tablet, laptop, smart watch, desktop, TV, or other device. The UE 420 includes terminal control circuitry 1105. The terminal control circuitry 1105 includes a processing circuit having one or more processing devices, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions.

Connected to the terminal control circuitry 1105 is a display 1100. The display 1100 is an example of a user interface which allows the user to interact with the UE 420. The display 1100 may include a touchscreen, LED or other type of display. The display 1110 may be integrated in the UE 420 as is shown in FIG. 11 or may be separate to the UE 420. For example, the display 320 may be a computer monitor, television screen, or head mounted display. The display 1120 enables a user to view data and graphical user interfaces as described herein. The UE 420 may include or be operably coupled to one or more other user interfaces 1112 such as a mouse, keyboard, touchpad, voice recognition, or gesture recognition circuitry.

The UE 420 includes terminal storage 1125 that is connected to the terminal control circuitry 1105. The terminal storage 1125 may include one or more memory devices, such as a read-only memory, random access memory, volatile memory, non-volatile memory, static memory, dynamic memory, flash memory, cache memory, and/or any non-transitory memory device that stores digital information. In addition, the terminal storage 1125 may store one or more instructions or programs which when performed by the terminal control circuitry 1105 may control it to perform one or more functions described herein. The terminal storage 1125 stores a health care monitoring application 1150. For example, the health care monitoring application 1150 may instruct the terminal control circuitry 1105 to execute logic to direct the UE 420 to present one or more graphical user interfaces (GUI). The GUIs present data generated by sensing device 100 or server 400 as well as GUIs to input user commands to control the sensing device 100.

The UE 420 may further include one or more of a Bluetooth transceiver 1124, a WLAN (IEEE 802.11x compliant) transceiver 1122, or a global positioning satellite (GPS) module 1126. The UE 420 may also include an RF transceiver 1120 compliant with Universal Mobile Telecommunications System (UMTS) Terrestrial Radio Access Network (UTRAN), Long Term Evolution (LTE) Evolved UTRAN (E-UTRAN), LTE-Advanced (LTE-A) or other wireless network protocols. The UE 420 may further include a USB port/transceiver 1128, Ethernet Port 1130 or RFID tag 1132. The UE 420 may also include a battery module 1114. One or more internal communication buses (not shown) may communicatively couple one or more of the components of the UE 420.

Figure 22:
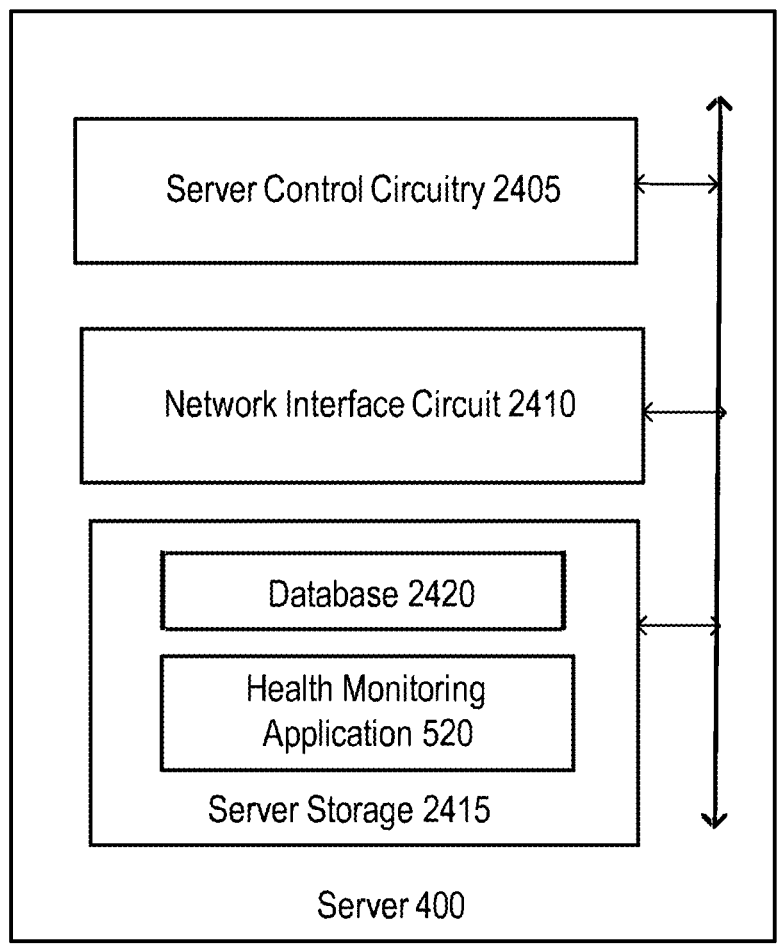
FIG. 22 illustrates a schematic block diagram of an embodiment of an exemplary server.

FIG. 22 illustrates a schematic block diagram of an embodiment of an exemplary server 400. The server 400 includes server control circuitry 2405 which includes a processing circuit having one or more processing devices, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The server includes server storage 2415 that is connected to the server control circuitry 2405. The server storage 2415 may include one or more memory devices, such as a read-only memory, random access memory, volatile memory, non-volatile memory, static memory, dynamic memory, flash memory, cache memory, and/or any non-transitory memory device that stores digital information. In addition, the server storage 2415 may store one or more instructions or programs which when performed by the server control circuitry 2405 may perform one or more functions described herein.

The server 400 includes a network interface circuit 2410 that includes an interface for wireless and/or wired network communications with one or more of the exemplary networks in the network 410. The network interface circuit 2410 may also include authentication capability that provides authentication prior to allowing access to some or all of the resources of the server 400. The network interface circuit 2410 may also include firewall, gateway, and proxy server functions.

Additionally provided within the storage 2415 is a database 2420. The database includes user specific profiles stored for each user of the health monitoring application 520. Additionally provided in the database 2420 is geolocation information associated with the output of the sensing devices 100. Further, various particulate (or particle) reference signatures are stored within the database 2420. These reference signatures may include bio-signatures, environmental signatures, or pollutant signatures. Finally, health advice, including medical or preventative advice, is stored in the database 2420. The health monitoring application 520 is configured to provide the health advice to a user via the UE 420 in response to output from the sensing devices 100 and/or user input. The database 2420 is described in more detail with reference to FIGS. 12A, 27A, 27 B.

Figure 23:
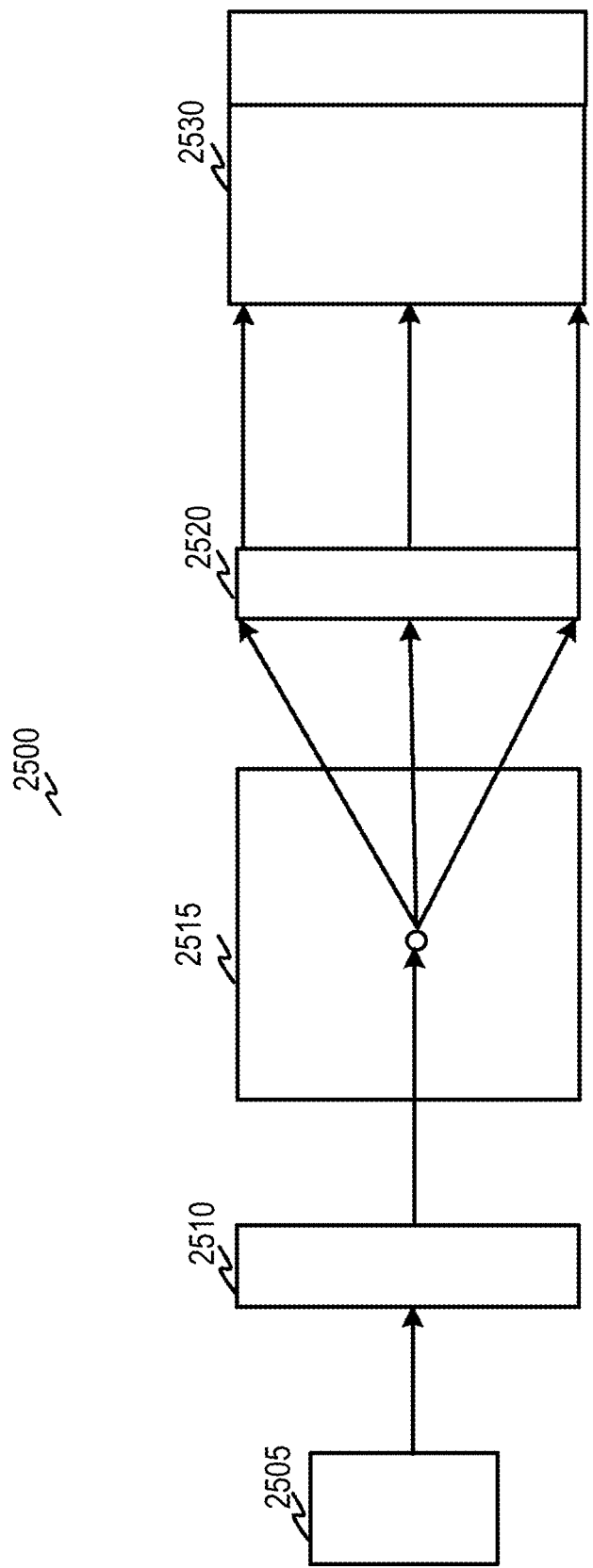
FIG. 23 illustrates a schematic block diagram of an embodiment of an exemplary sensor.

FIG. 23 illustrates a schematic block diagram of an embodiment of an exemplary sensor 2500. The sensor 2500 may be included as part of the sensor circuitry 2220 in the sensing device 100. The sensor 2500 is configured for identification of airborne particles. The sensor 2500 includes a light source 2505, a first optical filter 2510, a temporary particle trapping system 2515, a second optical filter and a detector.

In embodiments herein, the light source 2505 may be a laser or laser diode that illuminates a particle in the temporary particle trapping system 2515. The light source 2505 includes laser diodes or light emitting diodes (LEDs) that emit light at one or more specific wavelengths or over a range of wavelengths. For example, in one embodiment, the light source 2505 may emit light at one or more wavelengths in a range of 450 nm to 785 nm depending on a type of particle to be identified. The first optical filter 2510 may be embodied as a single line laser filter that filters all but one or more predetermined wavelengths or dichroic mirrors or Volume Bragg Grating.

The temporary particle trapping system 2515 is configured to immobilize a particle (e.g., the particle being represented by the black dot in FIG. 23) in an air sample. In some embodiments, the temporary particle trapping system 2515 is optional. For example, with slow or minimal airflow through the sensor 2500, it is possible to perform the analysis of a particle without immobilizing the particle within the particle trapping system 2515.

The second optical filter 2520 may be a notch filter having a notch corresponding to a same wavelength as the first optical filter 2510 or Rayleigh filtering. The detector 2530 obtains a spectral response of the reflected light and may include one or more types of spectrometers. The detector 2530 may be any suitable type of detector which is known to the skilled person, such as a spectrometer. The detector 2530 is configured to detect an intensity of light as a function of wavelength in a light range of interest which, in embodiments, is between the ultraviolet to the infrared range. The wavelength range depends on the type of particles and the particular spectral properties of the particles to be identified by the sensing device 100. The detector 2530 will be described further with reference to FIG. 24.

In operation in one or more embodiments herein, the sensor 2500 controls the light source 2505 to emit light at one or more wavelengths. The light impinges upon the first optical filter 2510. Assuming that the light is approximately spatially invariant over the area of the first optical filter 2510, the light passing through the first optical filter 2510 is reduced to a single wavelength of light. The light then interacts with an air sample in the optional temporary particle trapping system 2515. The biological, physical and chemical characteristics of a particle in the air sample affects the light. For example, the particle in the air sample interacts with the light and shifts the light to one or more different frequencies.

The light then impinges upon the second optical filter 2520 and the wavelength corresponding to the laser (or the first optical filter 2510 if present) is filtered and does not pass through the second optical filter 2520. The shifts in the wavelengths of the light due to the type of particle and their intensity are recorded by the detector 2530 as a spectral response. For example, the detector 2530 may be a spectrometer configured to detect an intensity of light in the UV and/or IR range. In this embodiment, the spectral response is recorded as a function of position (pixel number) on the detector 2530 and is correlated to an intensity at the wavelength of the light corresponding to that position. In some embodiments of the disclosure, an additional filter is placed next to the second optical filter 2520 and before detector 2530 in order to filter light which may lie outside the spectral range of interest. This additional filtering prevents unwanted light from reaching the detector 2530. The spectral response includes an intensity as a function of wavelength or frequency shifts. The spectral response detected depends on the type of particle. Thus, by comparing the detected spectral response to predetermined or stored spectral patterns or signatures of a particle, the type of particle in the air sample may be identified.

It will be understood that spectrometers according to other embodiments may be implemented in the sensor 2500. The choice of light source, detectors, and associated optics for use with a wide variety of spectroscopic techniques may be implemented in the sensor 2500. For example, Raman, fluorescents and infrared or ultraviolet reflectance spectroscopies may be implemented as well as Fourier Transform Infrared Spectroscopy. In an embodiment, the sensor 2500 may be configured to separate a Raman signal from a florescence signal, such that a same spectrometer may be used to detect both types of spectral responses.

In an embodiment, the sensing device 100 also measures the amount of a particular allergen in the environment. For example, a particle counter may be implemented to count the number of particles of a certain size. The particle counter, if provided, may be located in the sensor 2500 or in another location either within the sensing device 100 or in communication with the sensing device 100. However, one drawback with the particle counter is that some allergens can be of a similar size to other allergens or dust such as skin flakes shed by a human. The known particle counters do not distinguish between different types of allergen and non-allergens of a similar size; only the size of the particle is measured and not the composition of the particle. In this case, the particle counter may count other types of allergens or non-allergen particles as a same type of allergen particle and provide inaccurate readings.

In order to mitigate this problem, the sensor 2500 may be configured to determine the number of particles of a particular type of allergen. The sensor 2500 detects a number of readings of a particular allergen per hour and an airflow within the sensing device 100. From this information, the sensing device 100 may obtain a concentration of types of particles (such as parts per million PPM) with more accuracy. This information may also be provided to the server 400.

Figure 24:
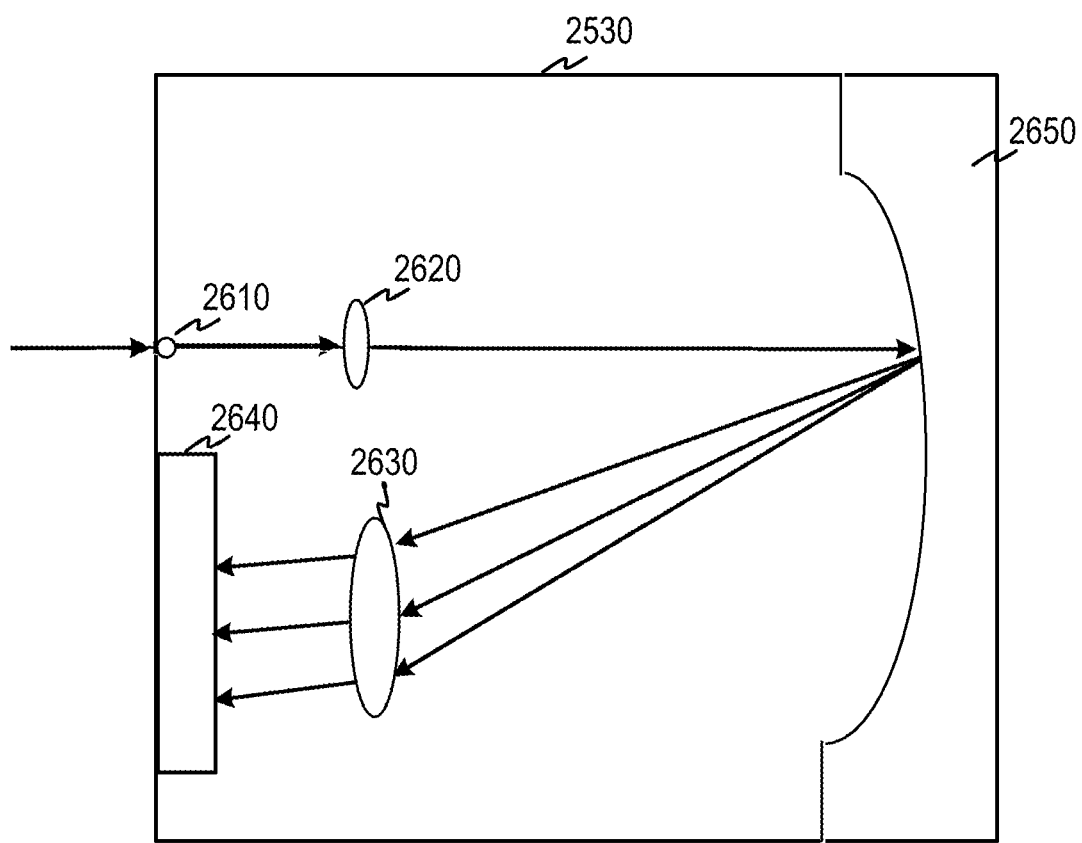
FIG. 24 illustrates a schematic block diagram of an embodiment of an exemplary detector.

FIG. 24 illustrates a schematic block diagram of an embodiment of an exemplary detector 2530. In an embodiment, the detector 2530 includes a spectrometer. The incident light passes through an input slit 2610 at a certain angle. A collimating lens 2620 collimates this slip transmitted light and guides it onto a grating 2650. The grating 2650 separates the incident light into different wavelengths and reflects the light at each wavelength at a different diffraction angle.

A focusing lens 2630 focuses an image of the light spatially dispersed into wavelengths by the grating onto linearly arranged pixels of an image sensor 2640. The image sensor 2640 converts the optical signals, which were dispersed into wavelengths by the grating 2650 and focused by the focusing lens 2630, into electrical signals. This provides a "count" of photons of light or intensity of light at each of the plurality of wavelengths to generate a spectral response or signature. These values of the intensity of light versus wavelength are then output. The output of the image sensor 2640 is described in more detail herein.

Figure 25A:
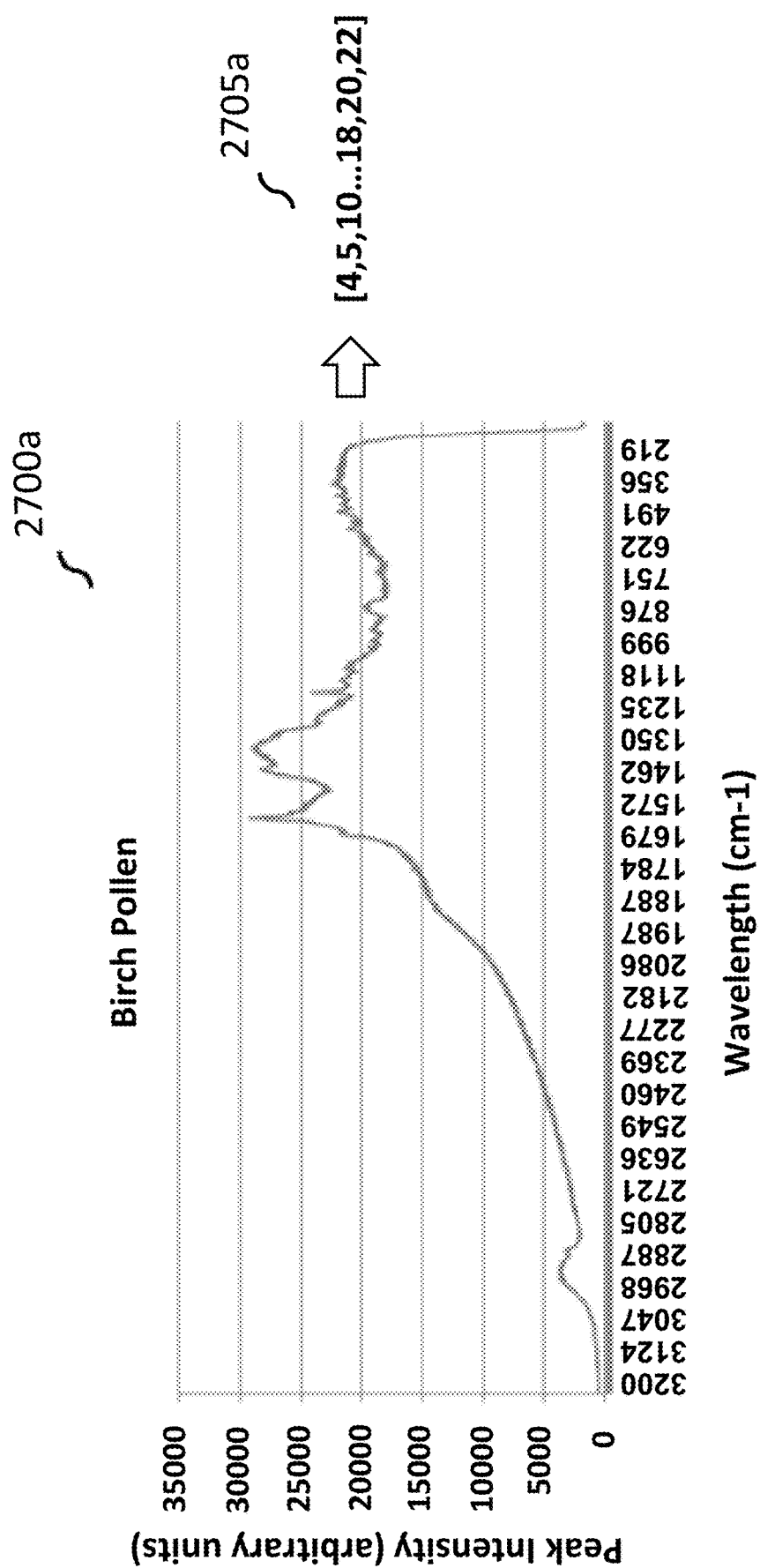
FIG. 25A illustrates a graphical diagram of an embodiment of an example reference signature for Birch pollen.

FIGS. 25A, 25B, 25C, and 25D illustrate graphical diagrams of embodiments of reference spectral signatures for various particles. Referring to FIG. 25A, a spectral signature for a birch pollen particle is shown in graph 2700a. On this graph, the intensity of the light (the count of photons) is plotted on the ordinate of graph 2700a and the wavelength of the photons is plotted on the abscissa of the graph 2700a.

Figure 25B:
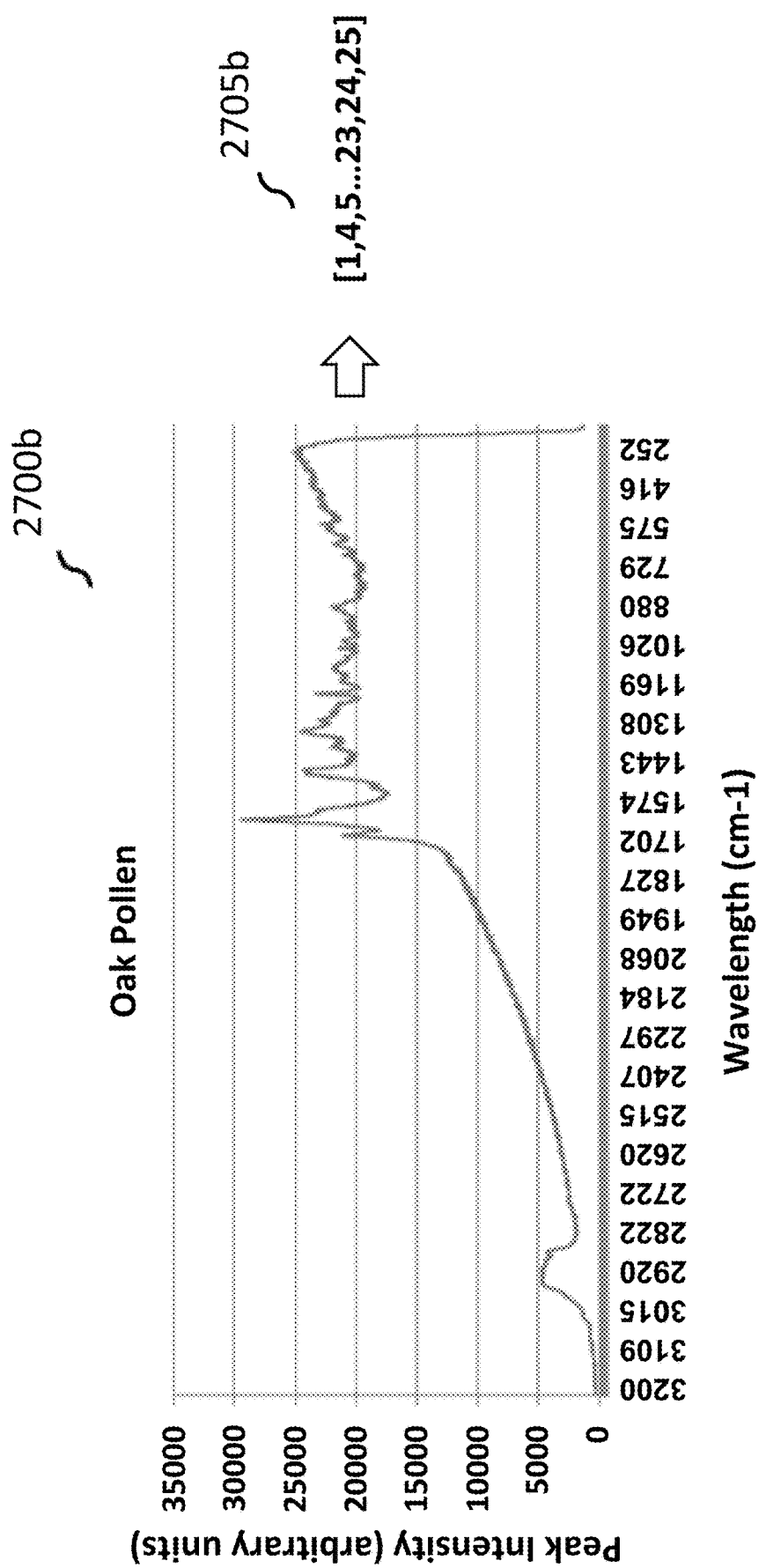
FIG. 25B illustrates a graphical diagram of an embodiment of an example reference signature for Oak pollen.

In other words, the graph 2700a shows the intensity of light at various wavelengths when a sample of birch pollen is tested using an embodiment of the sensor 2500, e.g., such as described with respect to FIG. 23 and FIG. 24. As will be apparent to the skilled person, the output graph 2700a is characteristic of a spectral response for a particle of an environmental allergen. In this case, the environmental allergen is a type of pollen and, specifically, birch pollen. FIG. 25B illustrates a second graph 2700b of the spectral signature or response of Oak pollen obtained by an embodiment of the sensor 2500 described with respect to FIG. 23 and FIG. 24.

In order to derive these reference spectral signatures, firstly, a sensor 2500 is calibrated by analyzing the laser light when no sample is included in the sensor of FIG. 23. This is termed the "dark mode" by a person skilled in the art. This produces an output which is then used to compensate the output when a sample particle is placed into the sensor of FIG. 23.

After the output from the "dark mode" is derived, a sample particle is processed by the sensor 2500 using an embodiment of a process, e.g., described with reference to FIGS. 23, 24 and 28. The output of the process with the sample is compensated by the dark mode output. This compensated result is the reference spectral signature for one sample of a particle, e.g., such as birch pollen.

In order to improve the accuracy of the reference spectral signature for a particle, different samples of the particle are subjected to the analysis by the sensor 500. Again, each output of the process is compensated by the dark mode output. The reference spectral signature is then derived from the spectral responses of the plurality of known samples of the particle. Typically, in excess of 10 sample signatures or a statistically significant number of sample signatures of a known particle, are obtained to derive a reference spectral signature. For example, the reference spectral signature may be selected as a median of the sample spectral signatures. By selecting a median sample signature, anomalies with a particular sample signature are mitigated. Of course, other mechanisms for mitigating such anomalies, such as using the mean or average of the intensity at each wavelength, may be implemented to determine the reference spectral signature for a particle.

After the reference spectral signature 2700a is derived for birch pollen, the intensity of light at predefined wavelengths is determined, e.g., spectral lines. The spectral lines may be represented and stored as a matrix or vector 2705a. In other words, for each wavelength value (for example every 10 nM), the intensity of the light at that wavelength is stored as a representative number in the vector 2705a. The wavelength value may be linearly divided across the entire range. For example, each number in the string may be the intensity at every 10 nM wavelength. However, the disclosure is not so limited, and the wavelength value may be logarithmically divided across the entire range. The reference spectral response 2700a may thus be numerically represented and stored.

An example vector for the birch pollen is shown at 2705a. In particular, the intensity values at predefined wavelength values in the reference signature graph 700a are obtained and represented as an array or vector or string of numbers. This vector may include a plurality of intensity values, e.g. 128 intensity values may be represented for 128 different wavelength values. Of course, any suitable number of values may be chosen. Also, although only the first three numbers and the last three numbers of the vector 2705a are illustrated in this example, the vector may include any number of intensity values over a range of predetermined wavelengths in the reference signature graph 2700a. As noted above, the predetermined wavelengths may be evenly spaced along the reference signature graph 2700a or in other embodiments, more intensity values may be selected around specific wavelengths or in a wavelength range with a high variability.

Referring now to FIG. 25B, similar features exist in the graph of the reference spectral signature of Oak pollen 2700b. The spectral signature 2700b may again be converted into a numerical representation, such as an array or vector 2705b. The array 2705b is illustrated in this example using just the first three and last three numbers for convenience. Again, this vector may include 128 values or may include more or less values. These reference spectral signatures 2700a and 2700b define unique particle characteristics of birch pollen and Oak pollen respectively. Therefore, any particle measured by the sensor 2500 having similar spectral characteristics may be identified as birch pollen or Oak pollen respectively. The reference spectral signatures for a plurality of particles, each defining unique characteristics, is stored in the database 2420 within server 400.

Figure 25C:
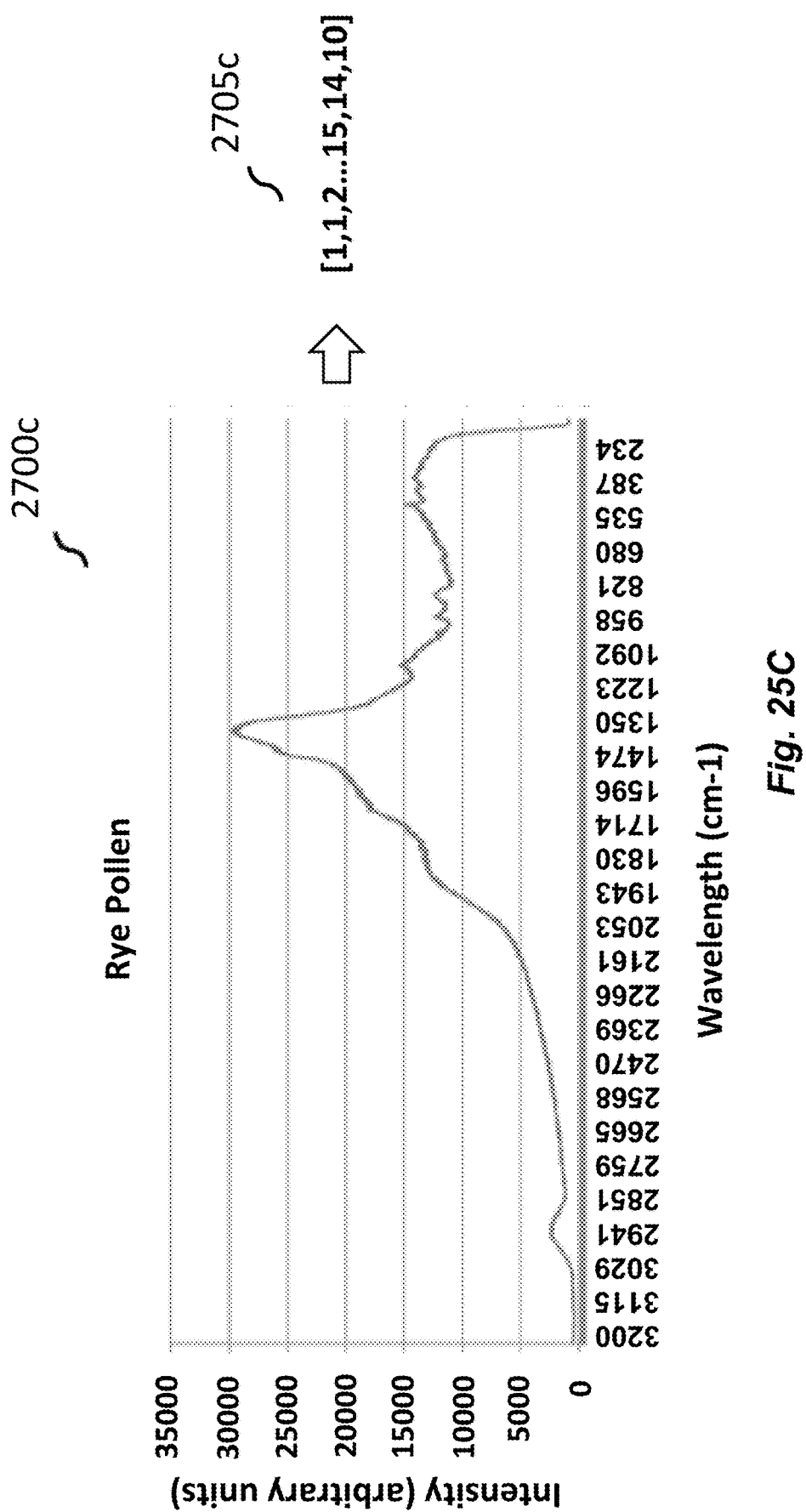
FIG. 25C illustrates a graphical diagram of an embodiment of an example reference signature for Rye pollen.

With reference to FIG. 25C, the spectral signature of Rye pollen defining its characteristics is shown in reference signature graph 700c. The reference signature graph 700c is represented as a vector 705c similar as described with reference to FIG. 25A and FIG. 25B.

Figure 25D:
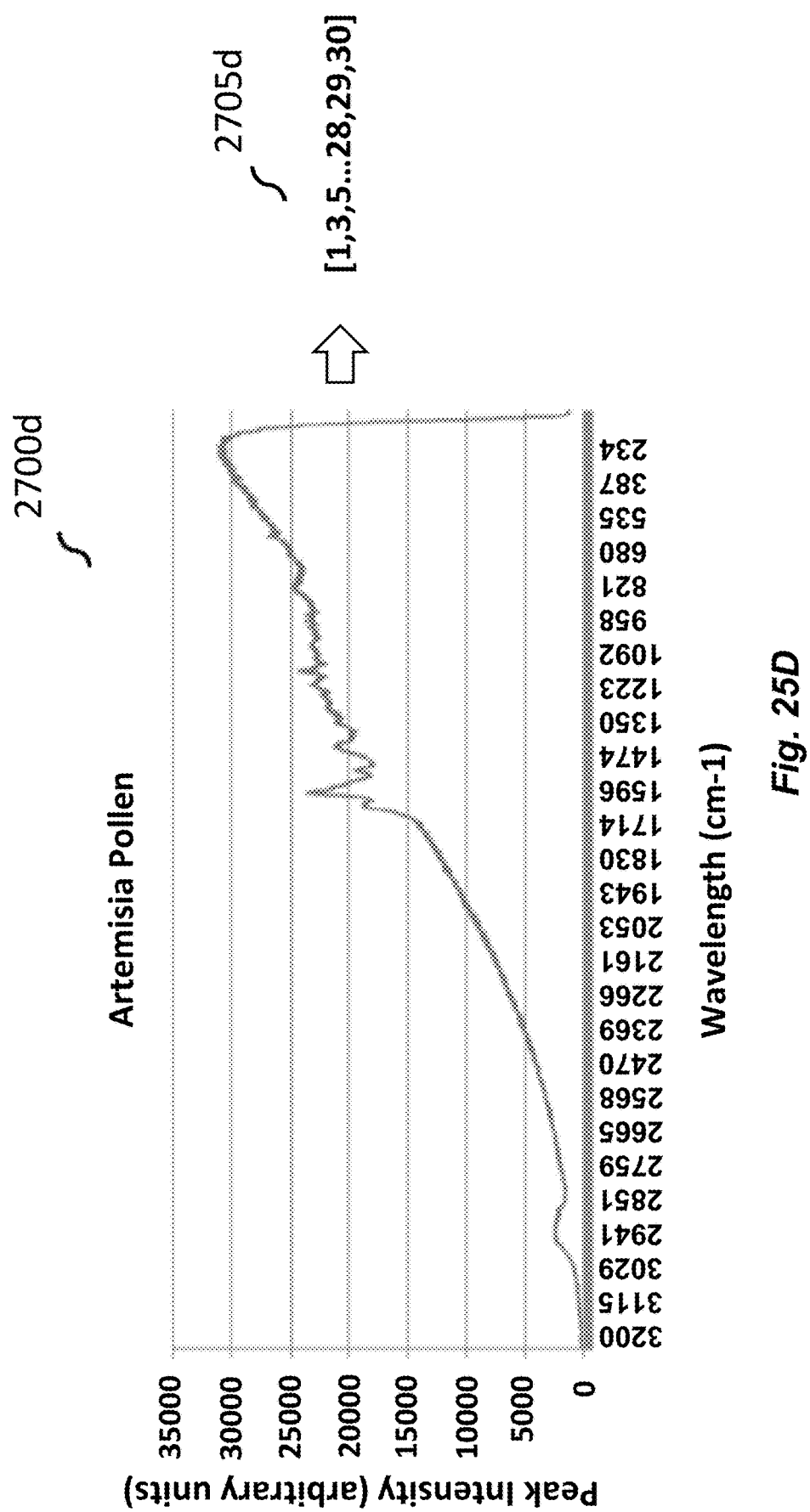
FIG. 25D illustrates a graphical diagram of an embodiment of an example reference signature for *Artemisia* pollen.

Similarly, with reference to FIG. 25D, a reference signature graph 700d illustrates an example of the spectral signature of *Artemisia* pollen. The reference signature graph 700d is represented as a vector 705d similar as described with reference to FIG. 25A. The reference spectral signatures of FIGS. 25A-25D may be obtained using the sensing device 100 according to embodiments described herein or by using a different device or method.

Figure 26A:
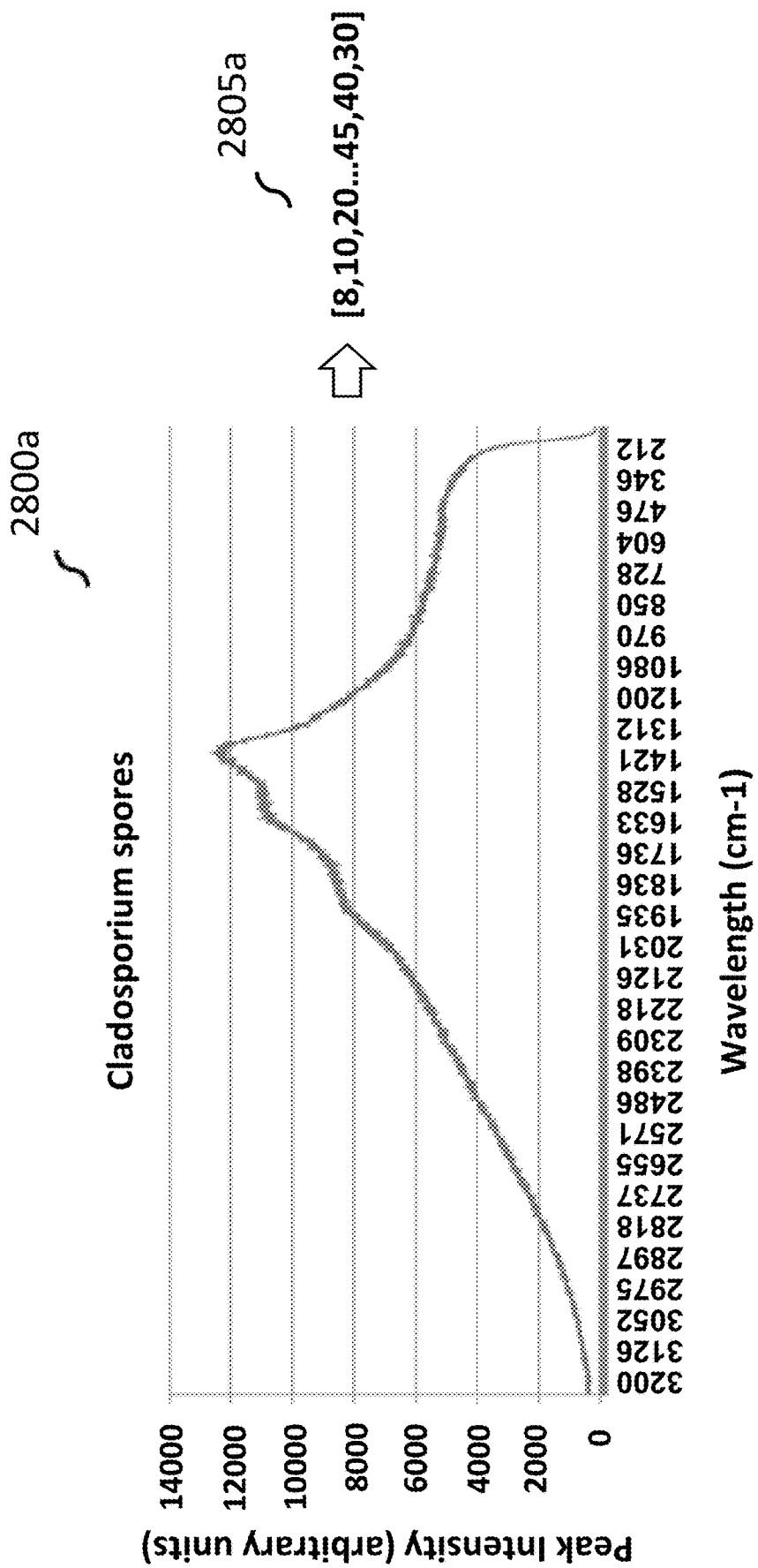
FIG. 26A illustrates a schematic block diagram of an embodiment of a signature for *Cladosporium* spores under test.
Figure 26B:
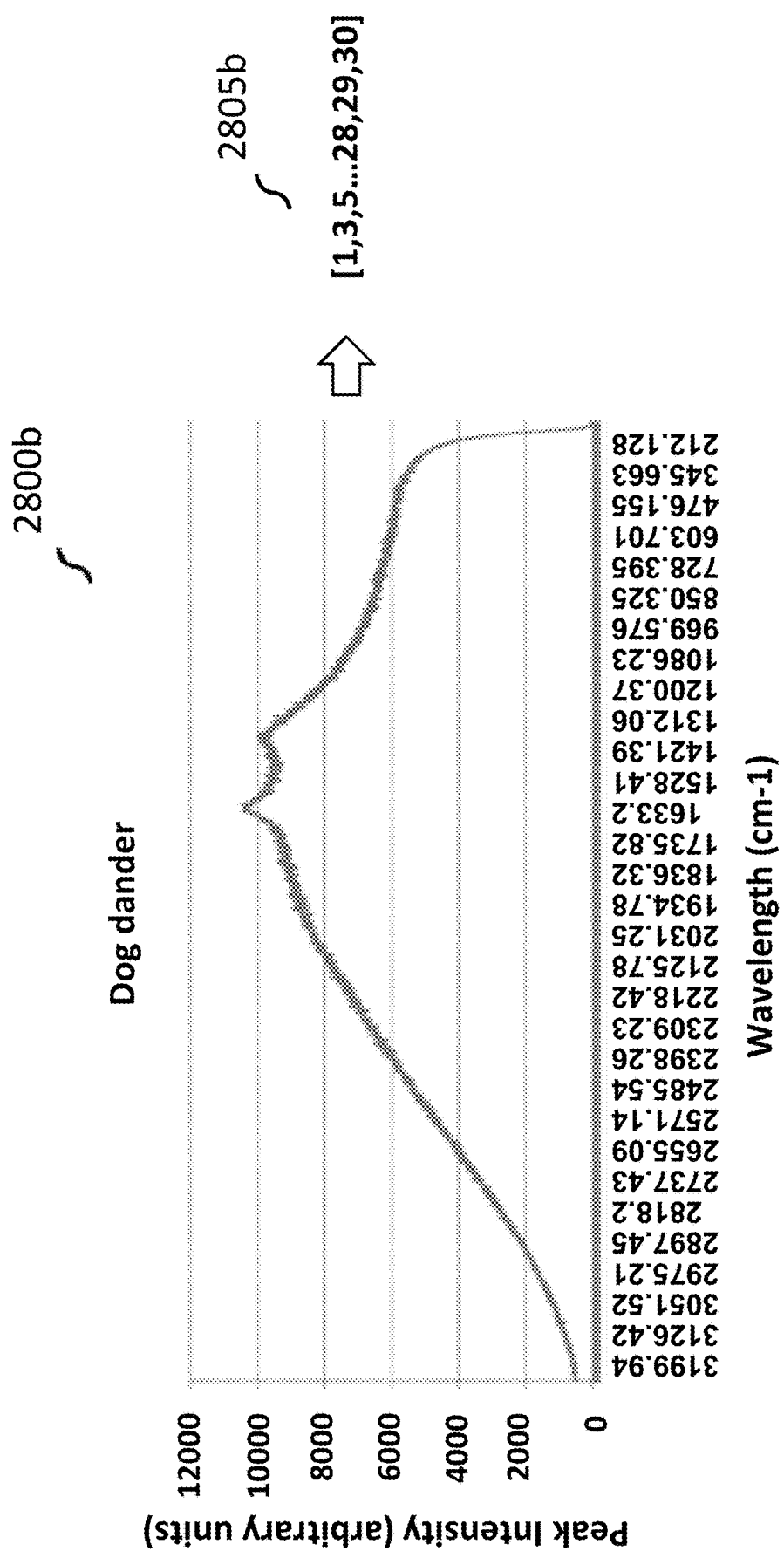
FIG. 26B illustrates a schematic block diagram of an embodiment of a signature for Dog dander under test.

FIG. 26A and FIG. 26B illustrate a schematic block diagram of an embodiment of exemplary spectral signatures for various other particles. The sensing device 100 located in a dwelling or business may analyze an air sample to identify a type of particle. During this sensing process, the spectral signature of the particle is obtained using the sensor 2500 within the sensing device 100. The sensing process may be initiated by a user or may be performed periodically or may be initiated by some other mechanism. For example, the sensing process may be performed periodically every 15 minutes or every hour, at the same times each day to monitor the presence of airborne particles.

Referring to FIG. 26A, it illustrates a schematic block diagram of an embodiment of a signature for *Cladosporium* spores under test. An example output of the sensor 2500 is shown in spectral signature graph 2800a for *Cladosporium* spores. The spectral signature graph 2800a from the sensor 2500 may be numerically represented by vector 2805a. The method for deriving the vector 2805a from the spectral signature graph 2800a is similar to that described above.

In an embodiment, the spectral signature graph 2800a and/or vector 2805a are transmitted to the server 400 over the network 410. The vector 2805a is compared with the reference spectral signatures stored within database 2420. The server control circuitry 2405 analyses the vector 2805a obtained from the sensing device 100 and compares this spectral signature with the vectors of the reference spectral signatures stored in database 2420.

Though vectors are described herein as numerically representing the spectral signatures, other representations may be derived. For example, an M×N matrix, a spectral pattern, or other representation may be used. Various techniques for comparing a measured spectral signature and reference spectral signatures may also be implemented, including, e.g., pattern recognition, matched filters, correlation filters, Gabor filters (with Gabor wavelets, log-Gabor wavelets), Fourier transforms or other algorithms may be used to compare the spectral signatures.

The server control circuitry 2405 then determines whether the received vector 805a corresponds to a stored reference signature vector. In the event that the received vector 805a does correspond to a stored reference signature vector, the identity of the particle is then returned to the sensing device 100 or UE 420 associated with the sensing device 100 or its location. In addition, health advice based on the identified particle may be provided to a user, wherein the health advice may reduce the impact of the identified particle on the user. This health advice may further be dependent upon an input of a severity of symptoms and type of symptoms suffered by the user.

Referring to FIG. 26B, it illustrates a schematic block diagram of an embodiment of a signature for Dog dander under test. The Dog dander spectral signature that is an output of the sensor 2500 is shown in the second graph 2800b. The second spectral signature graph 800b may be represented using vector 2805b. The vector 2805b is transmitted from the sensing device 100 to the server 400 over the network 450. The sever control circuitry 2405 then compares the received vector representative of the spectral response of the particle to the stored reference signatures. The server control circuitry 2405 determines whether the received vector 2805b corresponds to a stored reference signature. If the comparison is favorable, the identity of the particle is returned to the sensing device 100 and/or UE 420 and may also be used to generate health advice. Again, the health advice provided may also be dependent upon an input of the symptoms and severity of the symptoms suffered by the user.

In another embodiment, machine learning techniques are used to generate a training dataset for a reference spectral signature. The spectral signature is analyzed with a training algorithm to generate a vector or unique identifier. The training algorithm may include one or more of matched filters, correlation filters, Gabor filters (Gabor wavelets, log-Gabor wavelets) and/or Fourier transforms. A spectral response template for a particular type of particle is generated, e.g., that includes an array with intensity levels and wavelengths as coordinates.

A sever control circuitry 2405 compares a measured spectral response with the reference spectral response templates. Again, matched filters, correlation filters, Gabor filters (with Gabor wavelets, log-Gabor wavelets) and Fourier transforms can be used to perform the comparison between the spectral response vector and subset. Based on the comparison, the sever control circuitry 2405 generates a quality assessment value. In another embodiment, a multi-layered neural network can be implemented to process the spectral response and determine a type of particle.

Though the above embodiments describe the server control circuitry performing the comparison, the sensing device 100 may store reference spectral signatures and perform the comparison. The graphs and vectors are merely exemplary and other vectors or numerical representations may actually be implemented herein.

Referring to FIGS. 12A, 27 and 12B, various embodiments of a database 1220 stored within the server 400 or sensing devices 100 is shown. FIG. 12A illustrates a schematic block diagram of an embodiment of the database 1220 with a plurality of user profiles 1210a-n and a geolocation table 1221. The database 1220 stores one or more user profiles 1210a-n including information for users registered with the server 400. Typically, this registration occurs when a user buys a sensing device 100 and/or downloads an application program used to control the sensing device 100 to a UE 420. The user profile 1210a-n may include known allergies, age, gender, and other relevant medical history associated with that particular user. Additionally, the results of the output from the sensing device 100 are also stored within the user profile of database 2420. In particular, as seen in FIG. 12A, the date and time of each sensor measurement by the sensing device 100 is stored. Additionally, the location of the sensing device 100 when that sensor measurement took place is also stored. The location may include, as in this case, a borough of a larger town or, may be, geographical coordinates identifying the exact location of the sensing device 100. Also provided and stored in correspondence with this information is the sensor output from one or more sensors in the sensing device 100 at that location.

In addition, symptoms logged by the user of the UE 420 are also stored in correspondence with the sensor outputs. For example, in user profile 1210a, the symptoms logged by the user includes sore eyes and a runny nose. The user input also includes that the severity of these symptoms is a high severity. In other words, when the user is exposed to the particles analyzed by the sensor 2500, the user suffers these symptoms with a high severity. The symptoms may be due to allergies or asthma or other health conditions.

Additionally stored in the database 1220 is information pertaining to the particular geolocation. In this example, a borough of London (Westminster) is the geolocation. However, it is appreciated that any level of granularity is anticipated. For example, the geolocation may be instead geographical coordinates within a small range or area of a particular location or may be a very precise geographical location.

The date and time stamp of each sensor measurement at that location is stored in association with that location. Moreover, with each sensor measurement, the results from the sensor 2500 are stored in association with that particular sensor measurement. This allows for any location wherein sensing devices 100 are positioned to monitor the environmental and pollution particulates. The sensing device 100 may be configured to perform a measurement in accordance with one or more settings. For example, the sensing device 100 may be configured to perform a measurement periodically (for example every 15 minutes, 30 minutes, hour or the like). The sensing device 100 may be configured to perform a measurement at the same time every day (e.g., at 10 am, 11 am, 1 pm, 3 pm, etc.). The sensing device 100 may also be configured to perform a measurement every time a user logs symptoms with the UE 420 or upon request by a user of the UE 420.

The sensor 2500 is configured to determine the number of particles of a particular type of allergen. The sensor 2500 detects a number of readings of a particular allergen per hour and an airflow within the sensing device 100. From this information, the sensing device 100 may obtain a concentration of a particular allergen or pollutant or other particulate with more accuracy. This information may also be provided to the server 400 and stored in the geolocation table 1221. For example, a density of particles PI and P2 is recorded for Westminster associated with a first sensing device 100 for UserA. A density of particles P2 is recorded for Westminster associated with a second sensing device 100 for UserB.

The geolocation table 1221 may thus include a density of one or more types of particles detected at each location (density of particles PI, P2, P3, etc.) during a time period. This record enables trends for particular locations to be monitored and data collated for local authorities and government to monitor allergens, pollutants and other particulates that may have an impact on public health. This is particularly useful where high levels of a pollutant such as fine particulate matter are reported in a particular residential location where the impact on public health may be significant. Further, as this data is collected from the sensing devices 100 which are, in embodiments, located in a dwelling, the local authorities and government will have data from inside dwellings. This kind of data is not normally accessible to public bodies and is actually more representative of the allergens and irritants to which people are exposed on a daily basis.

In addition to this information, an identifier of the sensing device 100 reporting this information is stored in association with the sensor measurement. For example, in geolocation table 1221 shown in FIG. 12A, a first sensing device 100 reported an output of its environmental sensor circuitry 2220 (Sensor 1 output) and its pollution sensor circuitry 2225 (Sensor 2 Output) with respect to a report for UserA in Westminster. Another sensing device 100 also located in in Westminster associated with a UserB (e.g., another individual, entity, or a government agency) is noted as being in this locality. This second sensing device 100 also provides a report of sensor 1 output and sensor 2 output. The plurality of sensing devices 100 in a location allows councils and other local authorities to provide sensor measurement, from, for example street-side. In addition, this allows other user's sensing devices in this particular locality to provide crowd sourced information relating to pollutants and allergens within a user's home and locality. This collective information is very useful. For example, if a particle signature does not match a stored reference signature found at a particular locality and users complained of an allergic effect associated with this particle, the signature of that particle may be stored in the database 420 and health advice determined whilst the identity of the particle is established.

Figure 27A:
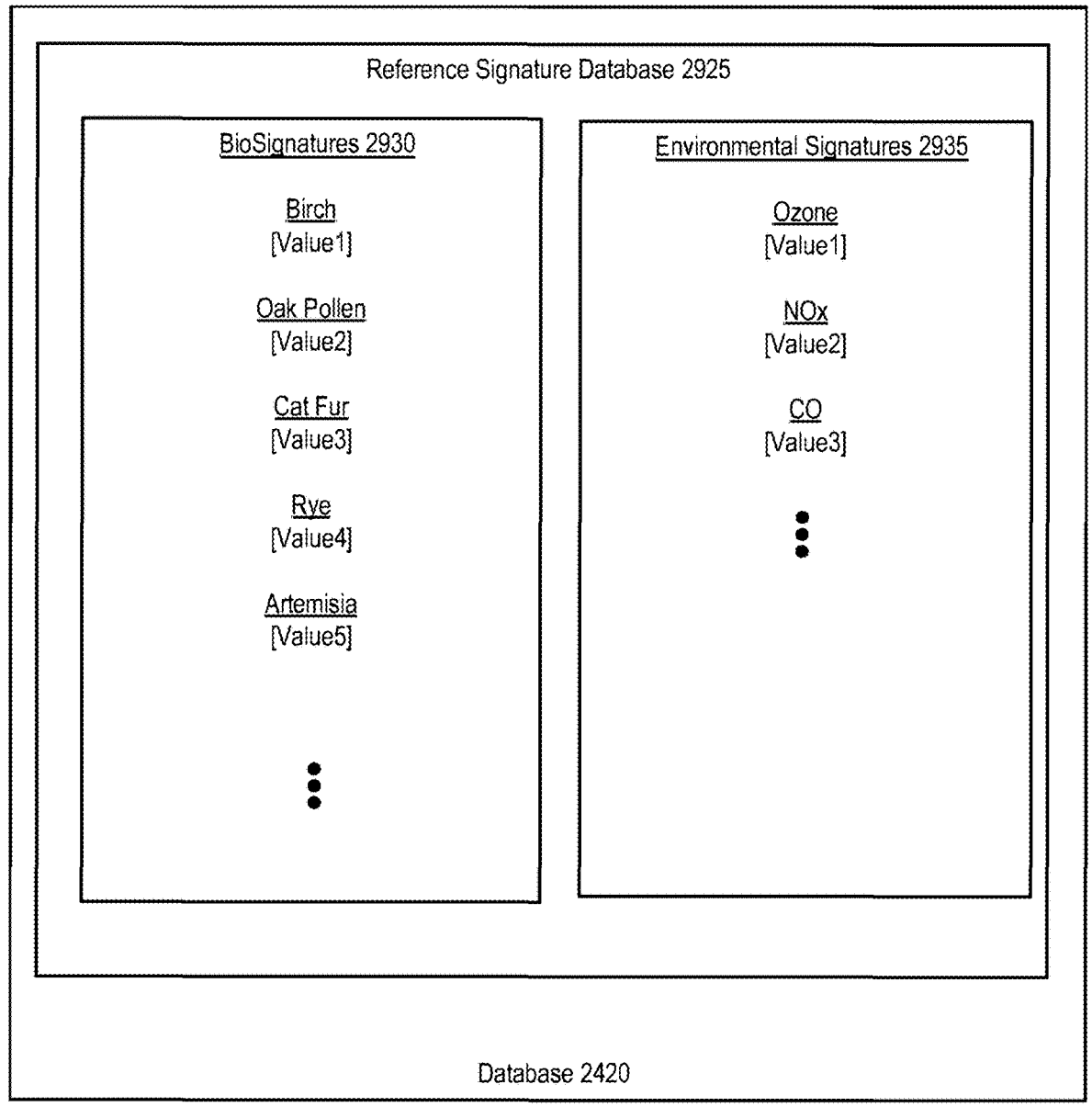
FIG. 27A illustrates schematic block diagrams of an embodiment of a database.

FIG. 27A illustrates a schematic block diagram of an embodiment of the database 2420 including a reference signature database 2925 for one or more types of particles. In particular, Biosignatures 930 stores reference signatures [Value 1, Value 2, Value 3, Value 4, Value 5, etc.] for one or more sample particles [e.g., birch, Oak pollen, cat fur, rye, *Artemisia*, etc.]. The reference signatures may be included as a numerical signature string or vector associated with each sample particle and its identity is stored. In other embodiments, the reference signatures may be patterns of the spectral signatures or other representations. In the example of FIG. 27A, the reference signature for birch, grass pollen, Rye pollen, *Artemisia* pollen and cat dander is stored. In addition, environmental signatures 2935 for pollutants such as nitrous oxide, carbon monoxide and ozone are also stored as part of the reference signature database 2925.

FIG. 27B illustrates a schematic block diagram of an embodiment of the database 2420 including a symptom table 2950. For example, the symptom table 2950 stores advice in response to detection of one or more types of particles. Typically, the advice is provided to a UE 420 associated with a user and displayed on a terminal display 1100.

In the non-limiting example, it is noted that the sensor 2500 identifies a particular type of allergen such as birch pollen. A user may input one or more symptoms and a severity of symptoms in a GUI of the health monitoring application 520 using either the sensing device 100 or the UE 420. The symptom table 2950 lists associated advice for the input symptoms, severity of symptoms and type of allergen or another particulate.

The health advice is pre-stored, e.g., based on medical assistance. For example, the health monitoring application 520 obtains an identification of various particles (allergens, pollutants or other types of particles) from a sensing device 100 and stores corresponding symptoms input by a user associated with those pollutants and allergens. Depending upon the severity of symptoms identified by the user, using either the UE 420 or the sensing device 100, appropriate advice to reduce the impact of the identified particle which is pre-stored in the database 2420 is returned to the UE 420.

In other instances, contact details for a medical practitioner (who specializes in the particular allergy and who is in the location of the user) are provided in addition to or instead of the advice. This may be appropriate, e.g., if the user is suffering severe allergic symptoms. Indeed, the user history and current symptoms and severity from the database 2420 may be simultaneously provided to the medical practitioner. This will alert the medical practitioner to the user's allergic reaction and the allergens present in their surroundings. This may assist in the medical treatment given to the user. In really severe cases, the emergency services may be automatically dispatched to the geolocation of the user.

The network of sensing devices also allows the system to compare levels of allergen and pollutants between an indoor area of the user and an outdoor area near a user. For example, the health advice may include a caution to limit outdoor activity when the outdoor levels of allergen and pollutants are higher than indoor levels based on such comparison. Users with asthma, COPD or other health conditions may then determine to limit outdoor activity.

Figure 28:
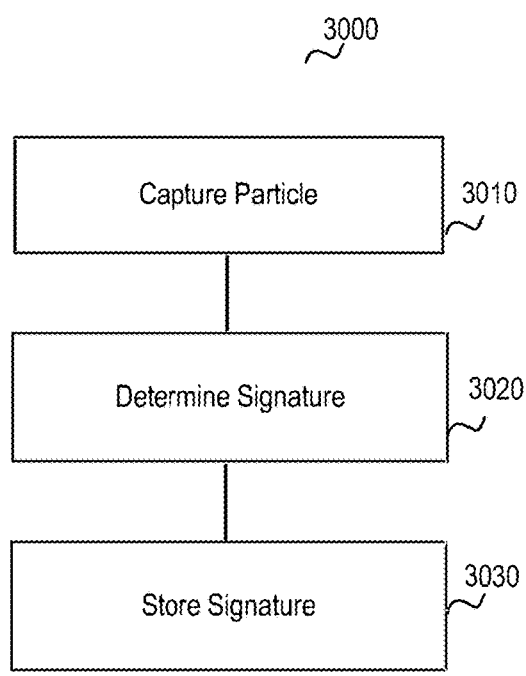
FIG. 28 illustrates a logical flow diagram of an embodiment of a method to obtain a reference signature of a particle.

FIG. 28 illustrates a logical flow diagram of an embodiment of a method 3000 to obtain a reference signature of a particle. A sample particle is captured in the sensor 2500 at 3010. The sensor 2500 determines a spectral signature at 3020 of the sample particle. A representation of the spectral signature, e.g., such as a vector or other numerical reference signature that characterizes the spectral signature of the particle, may be derived. As described previously in respect of FIG. 25A, a reference signature may be derived after a number of sample particles have been analyzed. In the example of FIG. 25A, the median sample value is taken as the reference signature and the numerical reference signature is derived. The numerical reference signature is stored in database 2420 at 3030.

Figure 29:
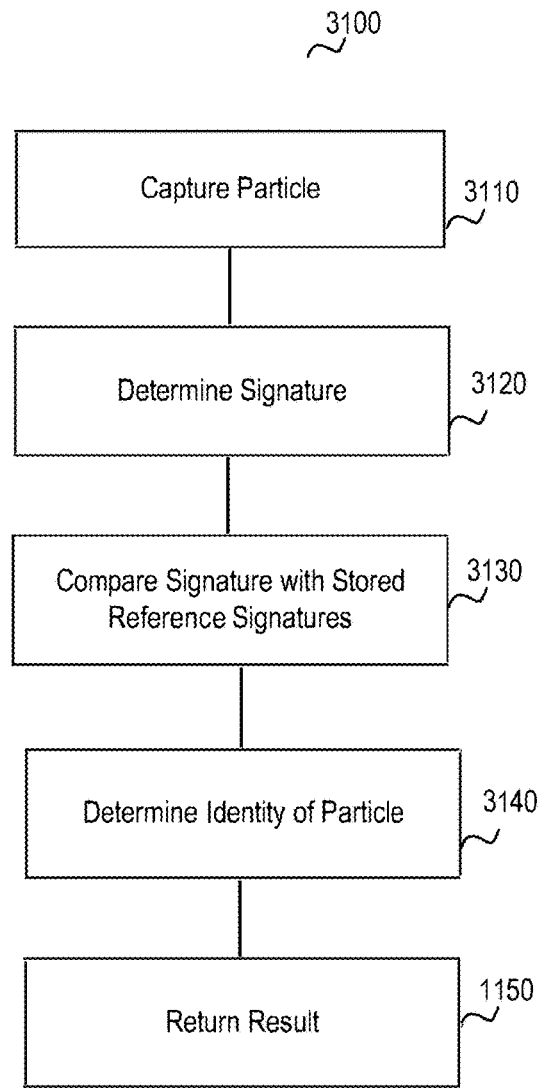
FIG. 29 illustrates a logical flow diagram of an embodiment of a method to apply to a particle under test.

FIG. 29 illustrates a logical flow diagram of an embodiment of a method 3100 to apply to a particle under test. The sensor 2500 captures a particle at 3110. The sensor 2500 processes the particle and determines a spectral signature of the particle at 3120. This spectral signature, as explained with reference to FIG. 26, may be represented as a numerical value such as a vector (which is a sequence) that is then provided to the server 400. This vector or other numerical representation of the spectral signature may be provided to the server 400 over the network 410 directly by the sensing device 100 or the UE 420.

The spectral signature is then compared with the reference spectral signatures stored in the database 2420 at 3130. On the basis of this comparison, the identity of the particle may be determined at 3140. Of course, if no particle match occurs, then a "no match" result is returned to the sensing device 100 or the UE 420. After the identity of the particle has been determined, the result is returned to the sensing device 100 and/or the UE 420 in step 3150. The result is then displayed to the user via the terminal display 1100.

Figure 30:
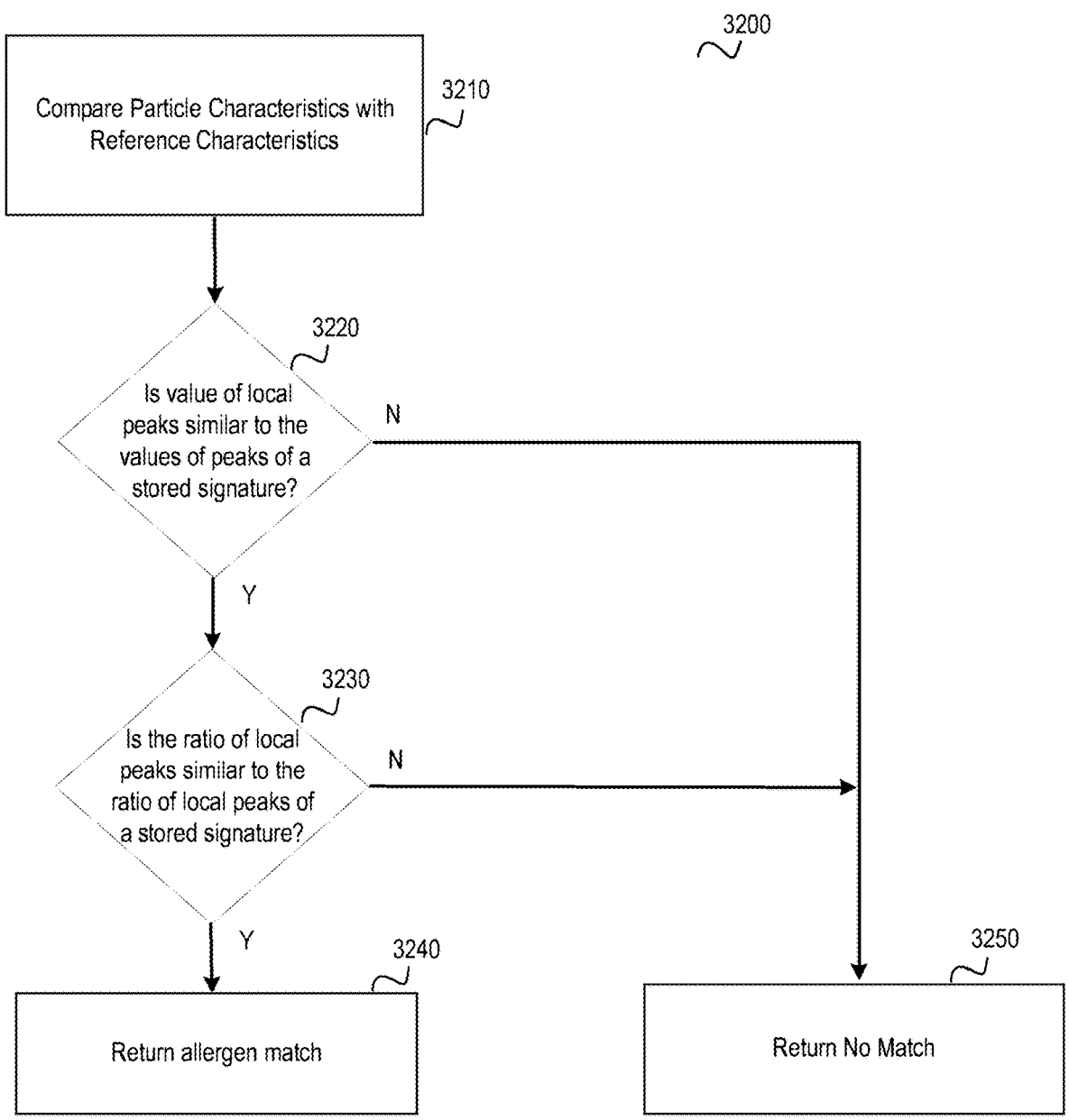
FIG. 30 illustrates a logic flow diagram of an embodiment of a method for determination of a type of particle.

FIG. 30 illustrates a logic flow diagram of an embodiment of a method 3200 for determination of a type of particle. The method 3200 for comparing a signature of a particle with stored reference signatures is described in more detail. The analyzed particle characteristics from the sensing device 100 are compared with the stored reference characteristics within the database 2420 at 3210. This comparison may be performed using one of several techniques. In this non-limiting embodiment, this comparison is carried out on a shape comparison basis using two steps.

In a first step, the values of local peaks in the spectral signature and reference spectral signatures are compared at 3220. For example, the wavelength and intensity of local minima and maxima are identified and these values (both the intensity and wavelength values) of the spectral signature under test and the reference spectral signatures are compared, e.g., on a peak-by-peak basis at a plurality of wavelengths. In this non-limiting instance, the peak intensity value at a plurality of wavelength values in the spectral signature under test is compared to the intensity value at a plurality of wavelength values in the reference spectral signatures.

In the event that the comparison of these values is within a predetermined threshold, the "yes" path is followed to step 3230. Alternatively, if the value of the local peak values is not within this threshold, the "no" path is followed to step 3250 wherein the process indicates that no match was found. In one non-limiting embodiment, the threshold is +1%, although other thresholds are envisaged.

In the event that the "yes" path is followed at 3220, the shape of the spectral signature of the particle under test is compared to the shape of the reference spectral signatures at 3230. For example, a ratio of the local peak values in the spectral signature of the particle under test is compared to the ratio of the local peak values in the reference spectral signatures. In other words, the relative heights (and associated wavelengths) of the local maxima and minima in the captured particle spectral characteristics are compared with the stored reference spectral characteristics.

In the event that the ratio of the local peaks of maxima and minima of the signature of the particle under test is not similar to the stored reference signatures, the "no" path is followed to step 3250 where the process ends. On the other hand, if the ratio of the local peaks of the maxima and minima is similar, the "yes" path is followed to step 3240 wherein the identity of the particle is returned to the sensing device 100 or the UE 420 as required.

One mechanism for determining whether the signature of the particle under test is similar to the reference signature is to represent the spectral signatures as vectors and perform the dot product between each reference spectral signature in the database and the spectral signature of the particle under test. The intensity at each data point of the signature of the particle under test is multiplied by the intensity at the equivalent data point in the reference signature from the database 2420. The more similar the two signatures are, the higher the value of the dot product, which is known as the score or the hit quality index. This calculation method is known as the correlation algorithm. The server control circuitry 2405 is configured to obtain the dot product between the signature of the particle under test and a plurality of reference signatures in the database 2405, and then report the first 50 hits, with the signatures listed in the order of decreasing value of the score. The server 400 then returns the signature with the highest value that is above a predetermined threshold.

FIG. 13A and FIG. 13B illustrate schematic block diagrams of embodiments of a graphical user interface 1300. The graphical user interface 1300 may be generated by a UE 420 or a sensing device 100 using a health care monitoring application 2350. Referring to FIG. 13A, a UE 420 having a display 1100 with a graphical user interface (GUI) 1300 is shown. Using this GUI 1300, a user may select the symptoms from which they are suffering. The display and GUI 1300 may be integrated into the sensing device 100.

In the example embodiment, the GUI 1300 includes a dropdown menu highlighting various symptoms associated with allergies 1310. Of course, other types of user interface are envisaged such as a keypad or radio buttons or the like. The GUI 1300 also includes a dropdown menu for selection of a severity of allergic symptoms 1320. In this example, the user has indicated that their symptoms include sneezing and coughing, and the symptoms are of a low severity.

The GUI 1300 further includes an initiate or "log" button 1350. The UE 420 then instructs the sensing device 100, and specifically, the sensing control circuitry 2205 via the sensing communication circuitry 2215 to perform a sensing measurement. The sensing device 100 captures particles and obtains an identity of one or more particles. The database 2420 is accessed and based on the identified one or more particles and the symptoms, advice is then returned to the UE 420. The advice appears in box 1330.

In the example of FIG. 13B, advice 1330 is displayed as noted in the database 2420. In this example, the advice 1330 includes that the user should close the window.

The above describes the user logging symptoms and the UE 420 or the sensing device 100 returning advice. The disclosure is not so limited. In embodiments, the UE 420 communicates with the server 400, and the server 400 links the environmental factors with patient symptoms. Thus, in embodiments, the interaction between different allergens and pollutants and the symptoms of one or more health problems, such as asthma and allergy, are correlated.

In this embodiment, the patient logs the symptoms from a list of the symptoms (using the drop-down menus of FIGS. 13A and 13B for example). These symptoms may be validated by a health professional before being provided in the drop-down menu. The user then provides the intensity of the symptoms and the impact on his or her daily activities. For example, the symptoms may impair sleep, restrict the ability of the user to work or play sport etc. In other words, the severity of the outbreak may be judged. When the user logs this information, the sensing device 100 measures the levels of one or more of pollution, allergen, and environmental factors (such as temperature, humidity, etc.) and communicates this information to the server 400.

This information from one or many users is then analyzed using a statistical tool, such as Principal Component Analysis, to determine one or more particulates that correlate with the logged symptoms. The server 400 may then determine which one or more particulates (pollution, allergen or other environmental factor) are likely causes of the symptoms. This information allows the user to be aware of the factor or allergen that is causing his or her symptoms. These symptoms may be stored in the database 2420 in association with the user and the associated one or more particulates. Accordingly, this information allows the user to identify the allergens that cause various symptoms for the user. This information is useful if the user is to attend a medical clinic as the clinician can review the symptoms experienced by the user and identify the allergen or factor present at the time of the symptom appearing and the time of day that the symptom appeared. This health monitoring application 520 may thus be used as an allergy diary and that known allergy diaries are no longer required. The health monitoring application 520 records the allergen and/or other factors and the symptoms for the user.

In addition, in embodiments, prediction of long-term allergy or asthma symptoms is performed by the health monitoring application 520. Specifically, once the allergen and other factors which trigger a user's symptoms are determined, future symptoms over the next few days, weeks and months can be predicted. In order to achieve this, long term weather and pollution forecasts are used, in conjunction with historical data, to predict the fluctuation in levels of pollution and allergen for a given geolocation. This information is used to indicate to a user (based at a geolocation) whether they will suffer allergic symptoms over the next few days, weeks, or months. Additionally, advice may be provided to the user in order to reduce the severity of the symptoms or even avoid the outbreak altogether by improving the air quality. In summary, the health monitoring application 520 may notify or warn the user of a possible long term allergen issue in advance. This warning allows preventative advice to be provided to the user.

In addition, during a periodic check of the environment, where the sensing device 100 detects a particular allergen or the amount of the particular allergen is above a certain level, the server 400 can push a warning to the user. The warning may include health advice about how to reduce the impact of the allergen or may include advice describing how to reduce the amount of the allergen in the atmosphere. This warning, therefore, allows the user to take preventative measures to avoid the symptoms associated with the allergen before those symptoms are exhibited.

In the above, the sensing device 100 communicates the spectral signature to the server 400. The server 400 may also communicate the database 2420 to the sensing device 100 for storage thereon. The sensing device 100 may then locally access the health advice or perform other functions described herein with respect to the server 400.

Although the above describes the provision of severity of symptoms, the disclosure is not so limited. The health advice provided in the database may not require the severity of symptoms or the symptoms themselves in order to return the health advice to the requesting device (the sensing device 100 or the UE 420). In particular, all that is necessary is that a signature (which define characteristics) of the particle under test is provided. The database 2420 (be it located in the server 400 or elsewhere) may then return the health advice associated with the identified particle.

Although the foregoing describes an allergy, the disclosure is not so limited and any kind of advice, warnings or data is envisaged.

FIG. 14 illustrates a schematic block diagram of an example of another GUI 1400 that may be generated using the health monitoring application 520. In this example, the health monitoring application 520 at the UE 420 and/or server 400 may provide data for and direct a UE 420 to display a graph 1405 including a presence/severity of symptoms and a concentration of a particulate. In this example graph 1405, the density of tree pollen over a period of one month is displayed. The severity or presence of symptoms logged by a selected user of the UE 420 is displayed. The graph 1405 may thus illustrate a correlation between density of a particulate and the presence and/or severity of symptoms of the selected user. The GUI 1400 may include a user selection for input of a time period for display, e.g., such as a weekly graph, a monthly graph or yearly graph. The GUI may also include a user selection for input of one or more allergens or pollutants or other particulates to be displayed in the graph 1405.

FIG. 15 illustrates a schematic block diagram of an example of another GUI 1500 that may be generated using the health monitoring application 520. The health monitoring application 520 on the UE 420 and/or server 400 correlates logged symptoms and severity of symptoms of a user with identified particulates. For example, the health monitoring application 520 may provide data for and direct a UE 420 to display a graph 1505 including concentration of particulates detected at times that a user logged having symptoms during a year. In the graph 1505, the density of particulates detected during symptomatic conditions during 2017 is displayed. The severity or presence of symptoms of a selected user of the UE 420 is correlated with the density of particulates detected over the year and a percentage of the particulates identified that may be causes of the symptoms over the period.

For example, the graph 1505 shows that a major cause of symptoms during 2017 may be grass pollen at 45% and then sulfur dioxide at 19% and tree pollen at 18%. The graph 1505 shows that a major cause of symptoms during a monthly period of July may be grass pollen at 25% and nitrogen dioxide at 25% and then other particulates at 20%. The health monitoring application 520 may thus determine and display data showing the correlation between various particulates and the presence and/or severity of symptoms logged by a user over a period of time. Again, the GUI 1400 may include a user selection for input of a time period for the display, e.g., such as a daily graph, weekly graph, a monthly graph or yearly graph.

FIG. 16 illustrates a schematic block diagram of an example of another GUI 1600 that may be generated using the health monitoring application 520 The health monitoring application 520 on the UE 420 and/or server 400 correlates logged symptoms and a minimal level of one or more types of particulates present when the symptoms are logged by a user. The symptoms of the user are thus correlated with a minimum concentration of identified particulates in which the logged symptoms were reported. The health monitoring application 520 may then provide data for and direct a UE 420 to display a GUI 1600 including a minimum concentration of a type of particulate detected when a user inputs having symptoms over a requested time period, such as a week, month or year.

For example, the graph 1605 includes a minimum concentration of a type of particulate matter (e.g., 3 PPM) detected when a user inputs having symptoms. The graph 1610 includes a minimum concentration of tree pollen (e.g., 6 PPM) detected when a user inputs or logs having symptoms. The graph 1605 and graph 1610 may thus help predict a minimal level of a particulate that may trigger symptoms in the future.

FIG. 17 illustrates a schematic block diagram of an example of another GUI 1700 that may be generated using the health monitoring application 520. The health monitoring application 520 on the UE 420 and/or server 400 correlates logged symptoms and resulting loss of productivity over a time period. The symptoms of a user are correlated with a typical loss of productivity due to such symptoms. Alternatively, or in addition thereto, a user may input loss of productivity due to symptoms. For example, the health monitoring application 520 may provide data for and direct a UE 420 to display a graph 1705 including loss of productivity over a period of time.

FIG. 18 illustrates a schematic block diagram of an example of another GUI 1800 that may be generated using the health monitoring application 520. The health monitoring application 520 on the UE 420 and/or server 400 stores and tracks a number of times a user logs intaking medication. The health monitoring application 520 may display a calendar 1805 correlated with a typical loss of productivity due to such symptoms. The user may input medication taken due to symptoms. For example, the health monitoring application 520 may provide data for and direct a UE 420 to display a calendar 1805 indicating days in which medication was logged as taken by a user. The calendar 1805 may thus help predict days in a month or year in symptoms are triggered in the future.

The health monitoring application 520 from the UE 420 or server 400 may transmit data to a healthcare provider 440. For example, one or more of the reports or data described herein may be transmitted to a healthcare provider 195. The healthcare provider 195 may provide health advice or medication using such data.

FIG. 31 illustrates a logical flow diagram of an embodiment of a method 2900 for determining a concentration or density of a particle in the air at a geolocation. For example, the concentration of a particle may be provided as a count of how much particulate is in the air. This particulate count represents the concentration of the particulate (e.g., pollen, ragweed, etc.) in the air in a certain geolocation at a specific time. The particulate count may be expressed, e.g., in grains of particulate per cubic meter over a 24-hour period.

First, the sensing device 100 identifies a type of particle, such as pollen, ragweed, etc. at 2905. The sensing device 100 is then configured to determine a number of that type of particle that is identified over a predetermined time period at 2910. For example, the sensing device 100 may take measurements every 10 minutes and provide a count of the number of that type of particle identified over a 24-hour period.

The sensing device 100 also detects airflow at the geolocation during the predetermined time period at 2915. For example, the sensing device 100 determines the speed of the airflow including the type of particle. From this information, the sensing device 100 may obtain a concentration of a particular type of particle for the predetermined time period at 2920.

This information may also be provided to a health monitoring application 520 at the server 400 or UE 420 at 2925. For example, a user may request current particulate counts from an associated sensing device 100 located, e.g., at their home or office. The health monitoring application 520 on a UE 420 transmits a request to the associated sensing device 100. The sensing device 100 then communicates the concentration of identified particles to the UE 420. A user may thus have a current, on demand report of concentration of identified particles, such as allergens, pollutants, or other particulates, from an associated sensing device 100 at their home or office.

In another example, the particulate count for a type of particle may also be provided to the server 400 and stored in the geolocation table 1221. For example, a concentration of particle type PI and P2 is recorded for Westminster associated with a first sensing device 100. A density of particles P2 is recorded for Westminster associated with a second sensing device 100. Sensing devices 100 located at other geolocations may also provide concentration of particle types that are recorded in the geolocation table 1221. The geolocation table 1221 may thus include a concentration of one or more types of particles detected by a sensing device 100 at different geolocations (density of particles PI, P2, P3, etc.) during a time period. This record enables trends for particular locations to be monitored and data collated for users, local authorities or government to monitor allergens, pollutants and other particulates that may have an impact on public health.

FIG. 32 illustrates a logical flow diagram of an embodiment of a method 3300 for providing a current concentration of particles in the air at a geolocation. For example, a user who is traveling to a different city or country may request a current update on concentrations of any potential allergens in the city or country. The user may thus prepare with medications or other remedies for any known allergens. The user inputs the request using the health monitoring application 520 on a UE 420 for a report on current particulate concentrations for a geolocation. The request may be for one type of particle (e.g. pollen, ragweed, or mold) or a general report on the types of particulates identified in the geolocation. The UE 420 transmits the request to the server 400. The server 400 receives the request at 3305 and obtains a current report for the geolocation, e.g., based on readings from one or more sensing devices 100 in the geolocation over the past minutes, hours, or 24 hours. In one embodiment, the server 400 requests current measurements from sensing devices in the requested geolocation at 3310. The sensing devices 100 may perform measurements upon receiving the request and provide the current measurements of particulate concentrations to the server 400 at 3315.

Additionally, or alternatively, the server 400 may access the geolocation table 1221 to obtain current measurements for the geolocation at 3320. For example, the server 400 may determine from time stamp that measurements have been received from sensing devices in the geolocation within a predetermined time period (e.g., within one minute or one hour). Since the measurements are current within an acceptable predetermined time period, the server 400 may then provide a report based on measurements from the database 2420. The server 400 may use a combination of both methods. For example, the server 400 may determine that certain sensing devices 100 in the geolocation have current measurements (e.g., within the hour) but that other sensing devices 100 in the geolocation have not reported current measurements. The server 400 may request current measurements only from these sensing devices 100.

The server 400 thus obtains current measurements from one or more sensing devices 100 in the geolocation. The server 400 may average or mean the measurements from each of the sensing devices 100 to provide a report on current particulate concentrations for the geolocation. The server 400 may provide a range of the particulate concentrations based on the current measurements from one or more sensing devices 100 in the geolocation to the requesting UE 420.

In addition, the server 400 may provide a report on current particulate concentrations for different locations within a same city or country. For example, the server 400 may provide a map illustrating different concentration levels of a particulate outside a building, street, in different regions of a city or a country.

FIG. 20 illustrates a logical flow diagram of an embodiment of a method 2000 for providing a forecast of particle levels in the air at a geolocation. A forecast may be provided for a specific site of a sensing device 100, e.g., inside a dwelling or business or for an outside location of a sensing device 100. In another embodiment, a forecast may be provided for a geolocation over a location of a plurality of sensing devices 100. The forecast may be determined by a sensing device 100 using its sensor outputs or by the server 400 using the sensor outputs of one or more of the plurality of sensing devices 100. The forecast predicts the particle concentration levels for a predetermined future time period. The particle concentration levels may include pollutant levels or allergen levels, such as pollen levels, ozone levels, etc. The future time period may include, e.g., a one day forecast, two day forecast or three day forecast.

To determine the forecast, concentration levels for a predetermined time period are obtained at 2002. For example, the current and past particle concentration levels for one or more days or weeks are obtained. The past concentration levels for the same days or weeks in one or more past years may also be obtained. The concentration levels are graphed versus time, and particle level signals generated for the predetermined time periods.

Patterns in the particle level signals are obtained. For example, trends, noise or periodicity of the particle level signals are determined at 2004. Based on past patterns, particle levels for a predetermined future time period are predicted at 2006. Forecasts for one to three days are generally more accurate than forecasts for longer time periods. An accuracy prediction for the forecast may also be determined.

The forecast of one or more particle levels for the predetermined future time period are provided to users at 2008. The health monitoring application 520 may display the forecasts on the GUI of UE 420 upon request or may push automatically for display on UE 420.

Statement of the Certain Embodiments of the Invention

1. In a first embodiment, a sensing device comprises: a storage device configured to store a database, wherein the database includes reference spectral signatures for a plurality of types of particles and health advice associated with each of the plurality of types of particles; a sensor configured to obtain a spectral signature of at least one particle in an airflow; and sensor control circuitry configured to: compare the spectral signature of the at least one particle in the airflow with the reference spectral signatures for the plurality of types of particles; identify a first type of particle corresponding to the at least one particle in the airflow; and access the database to obtain health advice associated with the identified first type of particle.

2. The sensing device of embodiment 1, further comprises a communication circuitry configured to: communicate over a network to a remote server; and receive from the remote server the reference spectral signatures for the plurality of types of particles and the health advice associated with each of the plurality of types of particles.

3. The sensing device of embodiment 2 wherein the sensor control circuitry is further configured to: store in the database the identified first type of particle and location information identifying a geographical location of the sensing device; and communicate the identified first type of particle and location information identifying a geographical location of the sensing device to the remote server.

4. The sensing device of embodiment 1 wherein the sensor control circuitry is configured to compare the spectral signature of the at least one particle in the airflow with the reference spectral signatures for the plurality of types of particles by: determining local maxima and minima points in the spectral signature of the at least one particle in the airflow; and comparing the local maxima and minima points in the spectral signature of the at least one particle in the airflow with local maxima and minima points in the reference spectral signatures for the plurality of types of particles.

5. The sensing device of embodiment 1, wherein the sensor control circuitry is further configured to: receive logged symptoms of a user; and access the database to obtain health advice associated with the identified first type of particle and the logged symptoms of the user.

6. The sensing device of embodiment 5, wherein the sensor control circuitry is further configured to: receive a logged severity of symptoms by a user; and access the database to obtain health advice associated with the identified first type of particle, the logged symptoms of the user and the logged severity of symptoms by the user.

7. The sensing device of embodiment 1, wherein the sensor control circuitry is further configured to: communicate the health advice associated with the identified first type of particle to a user device.

8. The sensing device of embodiment 1, wherein the sensor control circuitry is further configured to: receive the logged symptoms of the user and the logged severity of symptoms by the user from the user device.

9. The sensing device of embodiment 1, wherein the identified first type of particle includes at least one of: an allergen, pollutant or other type of airborne particulate.

10. In another embodiment, a method for monitoring airborne particles comprises: obtaining a spectral signature of at least one particle in an airflow; comparing the spectral signature of the at least one particle in the airflow with reference spectral signatures for a plurality of types of particles; identifying a first type of particle corresponding to the at least one particle in the airflow from the comparison; accessing a database to obtain health advice associated with the identified first type of particle; and providing the health advice to a user device for display.

11. The method of embodiment 10 wherein comparing the spectral signature of the at least one particle in the airflow with the reference spectral signatures for the plurality of types of particles comprises: determining local maxima and minima points in the spectral signature of the at least one particle in the airflow; and comparing the local maxima and minima points in the spectral signature of the at least one particle in the airflow with local maxima and minima points in the reference spectral signatures for the plurality of types of particles.

12. The method of embodiment 10, further comprising: receiving logged symptoms from the user device; and accessing the database to obtain health advice associated with the identified first type of particle and the logged symptoms of the user.

13. The method of embodiment 12, further comprising: receiving a logged severity of symptoms from the user device; and accessing the database to obtain health advice associated with the identified first type of particle, the logged symptoms of the user and the logged severity of symptoms by the user.

14. The method of embodiment 13, wherein the identified first type of particle includes at least one of: an allergen, pollutant or other type of airborne particulate.

15. The method of embodiment 14, further comprising: determining a number of the first type of particle in the air flow during a predetermined time period; determining an air flow speed during the predetermined time period; and obtain a concentration of the first type of particle during the predetermined time period.

16. The method of embodiment 15, further comprising: determining the logged severity of symptoms by the user over a requested time period and a concentration of at least the first type of particle over the requested time period.

17. The method of embodiment 16, further comprising: generating a report for display on the user device, wherein the report includes the concentration of the first type of particle over the requested time period and the logged severity of symptoms by the user over the requested time period.

18. The method of embodiment 15, further comprising: determining the logged symptoms by the user over a requested time period and a minimum concentration of at least the first type of particle in which the logged symptoms were reported over the requested time period.

19. The method of embodiment 18, further comprising: generating a report for display on the user device, wherein the report includes the minimum concentration of at least the first type of particle in which the logged symptoms were reported over the requested time period.

20. The method of embodiment 15, further comprising: determining the logged severity of symptoms by the user over a requested time period and loss of productivity over the requested time period; and generating a report for display on the user device, wherein the report includes the loss of productivity over the requested time period.

21. The method of embodiment 10, further comprising: obtain past particle level signals for a predetermined time period; determine signal patterns in the past particle level signals; and predict a particle concentration for a predetermined future time period using the signal patterns in the past particle level signals.

22. Another embodiment is a sample identification device comprising: a database storing characteristics of a reference sample in association with advice for a user corresponding to a health issue associated with the sample, and control circuitry configured to compare the characteristics of a sample under test with the stored characteristics and determine the identity of the sample in accordance with the comparison and return the associated advice to the user, wherein the database associates the advice with symptoms experienced by a user and, the control circuitry is further configured to return the advice associated with the identified sample and the symptoms.

23. The device of embodiment 22, further comprising communication circuitry configured to be connected to a network and to receive the characteristics of the sample under test.

24. The device of embodiment 22, wherein the characteristics are wavelength characteristics and the comparison is performed on the values of the local maxima and minima of the wavelength characteristics.

25. The device of embodiment 22, wherein the symptoms include severity information pertaining to the severity of the symptoms experienced by the user and an impact on quality of life of the user.

26. The device of embodiment 22, wherein the control circuitry is further configured to store the identity of the sample under test in association with location information identifying the geographical location of the sample under test.

27. The device of embodiment 22, wherein the sample is any of a particle, an allergen, pollution or environmental factors.

28. Another embodiment is a mobile terminal configured to receive advice from the device according to embodiment 22.

29. The mobile terminal of embodiment 7, further configured to provide the symptoms to the device.

30. The device of embodiment 22 wherein the advice further comprises environment recommendations.

31. Another embodiment is a sample identification method comprising storing characteristics of a reference sample in association with advice for a user corresponding to a health issue associated with the sample, comparing the characteristics of a sample under test with the stored characteristics; determining the identity of the sample in accordance with the comparison and return the associated advice to the user and associating the advice with symptoms experienced by a user and returning the advice associated with the identified sample and the symptoms.

32. The method of embodiment 31, further comprising receiving the characteristics of the sample under test.

33. The method of embodiment 31, wherein the comparison is performed on the values of the local maxima and minima of the characteristics.

34. The method of embodiment 31, wherein the symptoms include severity information pertaining to the severity of the symptoms experienced by the user.

35. The method of embodiment 31, comprising storing the identity of the sample under test in association with location information identifying the geographical location of the sample under test.

36. The method of embodiment 31, wherein the sample is any of a particle, an allergen, pollution or environmental factors.

37. A computer program comprising computer readable instructions which, when loaded onto a computer, configure the computer to perform a method according to embodiment 31.

38. A sample identification device comprising:
a database storing characteristics of a plurality of reference samples comprising airborne particles, in association with advice for a user corresponding to a health issue associated with the reference samples, and control circuitry configured to compare the characteristics of a sample under test with the stored characteristics; determine the identity of the airborne particles in the reference samples in accordance with the comparison and return an identification of the airborne particle in the samples, a level of airborne particles in the samples, and the associated advice to the user, wherein the database associates the advice with symptoms experienced by a user and, the control circuitry is further configured to return the advice associated with the identified sample and the symptoms.

39. A sample identification method comprising storing, in a database, characteristics of a reference sample in association with advice for a user corresponding to a health issue associated with the sample; comparing the characteristics of a sample under test with the stored characteristics of the reference sample; and determining the identity of the sample in accordance with the comparison and returning the associated advice to the user; and associating the advice with symptoms experienced by a user and returning each of the advice associated with the identified sample and the symptoms to the user.

40. A sample identification device comprising a database storing characteristics of a plurality of reference samples, each of the plurality of references samples comprising an airborne particle; a control circuitry or a cloud based network configured to compare the characteristics of a sample under test with the stored characteristics and determine an identity of the sample under test in accordance with the comparison, and return the associated identification of the airborne particle in the sample under test and an amount of the airborne particle in the sample under test to the user, wherein the database associates the identification and the amount with symptoms experienced by a user and, the control circuitry or the cloud based network is further configured to return a symptom diagnostic to the user based on the identification and the amount of the airborne particles detected and symptoms log.

41. A sample identification method comprising storing, in a database, characteristics of a plurality of reference samples, each of the plurality of reference samples comprising an airborne particle, each of the plurality of reference samples in association with advice for a user corresponding to a health issue associated with each of the plurality of reference samples; using control circuitry or a cloud-based network configured to compare the characteristics of a sample under test with the stored characteristics of the reference sample; determining the identity of the airborne particles in the sample according to the comparison and returning to the user the identity of the airborne particle in the sample under test and an amount of the airborne particle in the sample under test; and returning to the user a symptom diagnostic based on the identification and the amount of the airborne particles detected and symptoms log.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

All publications, patents, and patent documents are incorporated by reference herein, as though individually incorporated by reference. No limitations inconsistent with this disclosure are to be understood therefrom. In particular, International Publication Nos. WO2018167569 (Tamraz), WO2020198388 (Tamraz), U.S. Publication No. 20180266933 (Tamraz), and GB Publication No. 2560542 (Najjar), are each incorporated herein by reference in their entirety. The invention has been described with reference to various specific and preferred embodiments and techniques. However, it should be understood that many variations and modifications may be made while remaining within the spirit and scope of the invention.

The invention claimed is:

1. A sensing device, comprising:
a collection plate;
a fan configured to generate air flow through a receptacle of the sensing device, wherein the air flow guides particles in the air flow towards the collection plate;
an imaging device configured to capture images of the particles situated on the collection plate; and
a control device configured to control a speed of the fan to generate the air flow, wherein the speed of fan is determined using a location of the sensing device, and wherein the sensing device is further configured to control the speed of the fan for cleaning of the collection plate.

2. The sensing device of claim 1, further comprising a transceiver configured to:
communicate over one or more networks to a central server; and
process a command from the central server to control the speed of the fan, wherein the speed of the fan is determined and set by the central server using the location of the sensing device.

3. The sensing device of claim 1, wherein the speed of the fan is set to generate the air flow to approximate particle inhalation of a user in response to a residential location of the sensing device.

4. The sensing device of claim 1, wherein the speed of the fan is set to generate the air flow at approximately 7-9 liters per minute in response to a residential location of the sensing device.

5. The sensing device of claim 1, wherein the speed of the fan is set to generate the air flow at greater than 9 liters per minute in response to an industrial location of the sensing device.

6. The sensing device of claim 1, wherein the speed of the fan is set to generate the air flow at less than 7 liters per minute in response to an outside location of the sensing device.

7. The sensing device of claim 1, wherein the speed of the fan is lowered from its current speed setting in response to a rapid increase of particle density on the collection plate.

8. The sensing device of claim 1, wherein the speed of the fan is increased from its current setting in response to a slow increase of particle density on the collection plate.

9. A system for tracking airborne particles comprising the sensing device of claim 1 and a central server, the central server comprising:
a network interface circuit configured to communicate over one or more networks to the sensing device; at least one processing device configured to:
obtain a current image of a plurality of particles from the sensing device;
determine a location of a first particle using the current image;
compare the location of the first particle to locations of other particles in prior images from the sensing device;
determine the location of the first particle is substantially same as a location of one of the other particles in prior images from the sensing device;
discard a portion of the current image including the first particle;
locate at least a second particle in the current image; and
obtain a particle identification of the second particle in the current image.

10. The system of claim 9, comprising:
a health monitoring module configured to:
receive logged symptoms of a user; and
access a database to obtain health advice and environment recommendations associated with the logged symptoms of the user and the particle identification.

11. The system of claim 10, wherein the environment recommendations include recommendations for controlling one or more devices at a user location to help lower a particle level.

12. The system of claim 11, wherein the at least one processing device is further configured to communicate the health advice and environment recommendations to a user device.

13. The system of claim 11, wherein the at least one processing device is further configured to automatically control one or more devices at a user location based on the environment recommendations.

14. The system of claim 11, wherein the one or more devices at the user location include one or more of: a thermoset, humidifier, dehumidifier, lighting, vent, window, ventilation system, automated vacuum or fan.

15. The system of claim 9, wherein the identified second particle includes at least one of: an allergen, pollutant or other type of airborne particulate.

* * * * *